United States Patent
Ichimura et al.

(10) Patent No.: US 8,357,821 B2
(45) Date of Patent: Jan. 22, 2013

(54) AROMATIC AMINE COMPOUND, ORGANIC ELECTROLUMINESCENT ELEMENT INCLUDING THE SAME, AND DISPLAY DEVICE INCLUDING ORGANIC ELECTROLUMINESCENT ELEMENT

(75) Inventors: Mari Ichimura, Kanagawa (JP); Yoshihisa Miyabayashi, Aichi (JP)

(73) Assignee: Sony Corporation, Tokyo (JP)

( * ) Notice: Subject to any disclaimer, the term of this patent is extended or adjusted under 35 U.S.C. 154(b) by 150 days.

(21) Appl. No.: 12/613,331

(22) Filed: Nov. 5, 2009

(65) Prior Publication Data

US 2010/0109555 A1    May 6, 2010

(30) Foreign Application Priority Data

Nov. 6, 2008    (JP) .................. 2008-285438

(51) Int. Cl.
*C07C 211/54* (2006.01)
*H01L 51/54* (2006.01)

(52) U.S. Cl. ........ 564/308; 428/690; 428/917; 313/504; 313/506; 252/301.16

(58) Field of Classification Search .................. None
See application file for complete search history.

(56) References Cited

U.S. PATENT DOCUMENTS

2005/0260442 A1   11/2005   Yu et al.

FOREIGN PATENT DOCUMENTS

| JP | 2000-012229 | 1/2000 |
| JP | 2002-012861 | 1/2002 |
| JP | 2002-175883 | 6/2002 |
| JP | 20041-083513 | 3/2004 |
| JP | 2005-015419 | 1/2005 |
| JP | 2005-116247 | 4/2005 |
| JP | 2006-199595 | 8/2006 |
| JP | 2007-204425 | 8/2007 |

OTHER PUBLICATIONS

Database CAPLUS on STN, Acc. No. 1940:2707, Morton et al., Journal of the American Chemical Society (1939), 61, p. 2902-2905 (abstract).*
Japanese Office Action issued on Oct. 26, 2010, for corresponding Japanese Patent Application No. 2008-285438.

* cited by examiner

*Primary Examiner* — Brian J Davis
(74) *Attorney, Agent, or Firm* — K&L Gates LLP

(57) ABSTRACT

An aromatic amine compound is represented by general formula [I]:

General formula [I]:

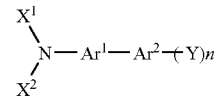

wherein $X^1$ and $X^2$ each represent a group selected from an alkyl group, an aryl group, an allyl group, an alkoxy group, and an aryloxy group, $X^1$ and $X^2$ may be the same or different, $Ar^1$ and $Ar^2$ each represent an arylene group, $n \geq 1$, at least one of substituents Y is a substituent selected from a trifluoromethyl group, a cyano group, and a halogen group, and other substituents Y are groups each selected from a hydro group, an alkyl group, an aryl group, an allyl group, an alkoxy group, and an aryloxy group.

10 Claims, 35 Drawing Sheets

AROMATIC AMINE COMPOUND, ORGANIC ELECTROLUMINESCENT ELEMENT INCLUDING THE SAME, AND DISPLAY DEVICE INCLUDING ORGANIC ELECTROLUMINESCENT ELEMENT

CROSS REFERENCES TO RELATED APPLICATIONS

The present application claims priority to Japanese Priority Patent Application JP 2008-285438 filed in the Japan Patent Office on Nov. 6, 2008, the entire content of which is hereby incorporated by reference.

BACKGROUND

The present disclosure relates to an aromatic amine compound useful for an electron transport material, a hole transport material, or a luminescent material of an organic electroluminescent element, an organic electroluminescent element including the aromatic amine compound, and a display device including the organic electroluminescent element.

Recently, organic electroluminescent elements (EL elements) have attracted attention as one of flat panel displays that are self-luminous, that have a high response speed, and that do not have angle-dependent visibility, and thus interests in organic materials constituting such organic electroluminescent elements have been increasing. In particular, among such organic materials, there are few materials that can form a stable blue-light-emitting layer, which is an important problem to be solved in order to realize a full-color organic electroluminescent element.

In order to realize a high luminance and a high efficiency of an organic electroluminescent element, a doping method has been employed in which a light-emitting layer is constituted by a host compound and a guest compound (dopant). By selecting a host compound having a high energy transfer efficiency from the host compound to the dopant compound, the luminous efficiency of the organic electroluminescent element can be increased. For example, it is known that 9,10-diphenylanthracene compounds can be used as an electron-transporting host or a hole-transporting host.

Aromatic amines have been actively studied as a photosensitive material for electrophotography. Subsequently, it has been reported that aromatic amines exhibit excellent characteristics as a hole transport material of an organic electroluminescent element. Consequently, a large number of such compounds have been reported. Recently, the use of an aromatic amine as a light-emitting layer has also been proposed.

An organic layer constituting an organic electroluminescent element is formed by using various organic materials as described below.

Japanese Patent No. 3506281 (paragraphs 0006 to 0010, 0079, and 0085) titled "organic electroluminescence element" discloses an organic electroluminescent element including an organic compound layer having at least a recombination region where a hole and an electron are recombined and a light-emitting region that emits light in response to the recombination, and a pair of electrodes sandwiching the organic compound layer, in which the recombination region and/or the light-emitting region contains an aromatic amine as a fluorescent dopant and a distyryl arylene compound as a luminescent material (host material). According to the organic electroluminescent element described in Japanese Patent No. 3506281, at least one of the recombination region where a hole and an electron are recombined and the light-emitting region that emits light in response to the recombination contains a fluorescent dopant having a specific structure. For example, the luminescent color is not significantly changed even after this organic electroluminescent element is driven for a long time, and thus the organic electroluminescent element has a long life time. In addition, the organic electroluminescent element has a high luminous efficiency. Accordingly, the organic electroluminescent element is suitably used as, for example, a display of a device used in the information industry.

Japanese Patent No. 3104223 (paragraphs 0006 to 0008 and 0123) titled "organic electroluminescent element" describes that when a perylene compound is used as a mixture with an aromatic amine compound, aromatic diamine compound, or aromatic triamine compound having a specific aromatic hydrocarbon or aromatic heterocyclic ring as a substituent, a red-light-emitting organic EL element having particularly good characteristics can be obtained.

Japanese Patent No. 3011165 (paragraphs 0008 to 0010 and 0196) titled "organic electroluminescent element" describes that when a 5-cyanopyrromethene-$BF_2$ complex is used as a mixture with an aromatic amine compound, aromatic diamine compound, or aromatic triamine compound having a specific aromatic hydrocarbon or aromatic heterocyclic ring as a substituent, a red-light-emitting organic EL element having particularly good characteristics can be obtained.

Japanese Patent No. 3092584 (paragraphs 0008 to 0010 and 0142) titled "organic electroluminescence element" describes that bis-2,5-(2-benzazoyl)hydroquinone compound is used as a mixture with an aromatic amine compound, aromatic diamine compound, or aromatic triamine compound having a specific aromatic hydrocarbon or aromatic heterocyclic ring as a substituent, a red-light-emitting organic EL element having particularly good characteristics can be obtained.

Japanese Unexamined Patent Application Publication No. 2001-257074 (paragraphs 0004 to 0006 and 0017) titled "hydrocarbon compound and organic electroluminescent element" discloses an organic electroluminescent element including a pair of electrodes and at least one layer containing at least one 9,10-di(3'-fluoranthenyl)anthracene derivative and disposed between the electrodes.

Japanese Unexamined Patent Application Publication No. 2002-69044 (paragraphs 0004 and 0011) titled "organic electroluminescence element" describes that by adding a novel hydrocarbon compound in which an aryl structure is bonded to a fluoranthene structure to an organic compound film, heat resistance of an organic electroluminescence element is improved, and furthermore, a hole-transporting property and an electron-transporting property are improved to realize a high luminous efficiency.

Japanese Unexamined Patent Application Publication No. 2000-182776 (paragraphs 0008 to 0013) titled "organic multilayer electroluminescence element" discloses an anthracene derivative as a typical example of a material of a hole-transporting layer.

Japanese Patent No. 3838816 (paragraphs 0009 to 0012) titled "compound for organic EL element" discloses a phenylanthracene derivative used as a compound for an organic EL element.

Japanese Unexamined Patent Application Publication No. 2001-335516 (paragraphs 0004 to 0014) titled "organic electroluminescence element" discloses a compound having a diphenylanthracene structure in the center thereof and a specific structure substituted with aryl groups in the terminals thereof.

Japanese Unexamined Patent Application Publication No. 2002-260861 (paragraphs 0004, 0005, and 0013) titled "organic light-emitting device" discloses benzenoid compounds which include a polycyclic aromatic hydrocarbon (PAH) and a combination of two or more PAHs (including benzene, naphthalene, and anthracene) and which are suitable for a host component of a light-emitting layer of an organic light-emitting device.

Furthermore, Japanese Patent No. 4041816 (paragraphs 0004 to 0006, and 0021) titled "organic electroluminescence element and anthracene derivative" discloses an anthracene derivative for realizing an organic EL element.

In Japanese Patent No. 3092584, red-light emission is realized by forming a light-emitting layer composed of a mixed layer of bis-2,5-(2-benzazoyl)hydroquinone compound and an aromatic amine compound. In Japanese Patent No. 3011165, red-light emission is realized by forming a light-emitting layer composed of a mixed layer of 5-cyanopyrromethene-$BF_2$ complex and an aromatic amine compound. In Japanese Patent No. 3104223, red-light emission is realized by forming a light-emitting layer composed of a mixed layer of a perylene compound and an aromatic amine compound. However, the emission luminance obtained by these techniques is low, and thus the red-light emission is not sufficient for practical use.

In the development of an organic electroluminescent element, selection of a light-emitting material is the most important factor for ensuring the reliability of the element. Among materials that can be used as a red-light-emitting material, there are few materials which have good color purity and a high fluorescence quantum efficiency, and which can be formed into a stable amorphous thin film. Furthermore, the realization of a red-light-emitting element that has a high luminance, that is stable, and that has high color purity has been desired.

It is desirable to provide an aromatic amine compound that can be suitably used for forming an organic layer constituting an organic electroluminescent element and that can emit red light with a high fluorescence quantum efficiency, an organic electroluminescent element including the aromatic amine compound, and a display device including the organic electroluminescent element.

SUMMARY

The present embodiments provide an organic electroluminescent element including a light-emitting layer composed of an aromatic amine compound having a specific structure and a material that can efficiently transfer energy to the aromatic amine compound, and reached the present invention, which provides a highly reliable red-light-emitting element having a high luminance.

Specifically, according to an embodiment, an aromatic amine compound is represented by general formula [I] below.

General formula [I]:

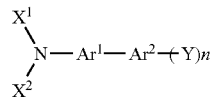

(In general formula [I], $X^1$ and $X^2$ each represent a group selected from an alkyl group, an aryl group, an allyl group, an alkoxy group, and an aryloxy group, $X^1$ and $X^2$ may be the same or different, $Ar^1$ and $Ar^2$ each represent an arylene group, $n \geqq 1$, at least one of substituents Y, which are substituents of $Ar^2$, is a substituent selected from a trifluoromethyl group, a cyano group, and a halogen group, and other substituents Y are groups each selected from a hydro group, an alkyl group, an aryl group, an allyl group, an alkoxy group, and an aryloxy group.

According to an embodiment, an organic electroluminescent element includes an anode, a cathode, and an organic layer disposed between the anode and the cathode, in which at least one layer constituting the organic layer is an amine-compound-containing layer containing, as a dopant material, at least one of the above aromatic amine compounds.

According to an embodiment, a display device includes a pixel portion in which a plurality of pixels each including the above organic electroluminescent element are arranged, and a control unit configured to control on and off of a voltage applied to each of the pixels of the pixel portion.

According to an embodiment, there is provided an aromatic amine compound which can be used as a preferable guest material that can be suitably combined with a host material composed of a compound having an anthracene skeleton and which emits red light with a high fluorescence quantum efficiency when an organic electroluminescent element is produced.

According to an embodiment, there is provided an organic electroluminescent element that emits red light with a high fluorescence quantum efficiency by suitably combining the above aromatic amine compound with a host material composed of a compound having an anthracene skeleton.

Furthermore, according to an embodiment, there is provided a display device that emits red light with a high fluorescence quantum efficiency and that can realize a full-color display.

Additional features and advantages are described herein, and will be apparent from the following Detailed Description and the figures.

DETAILED DESCRIPTION

Figure 1:
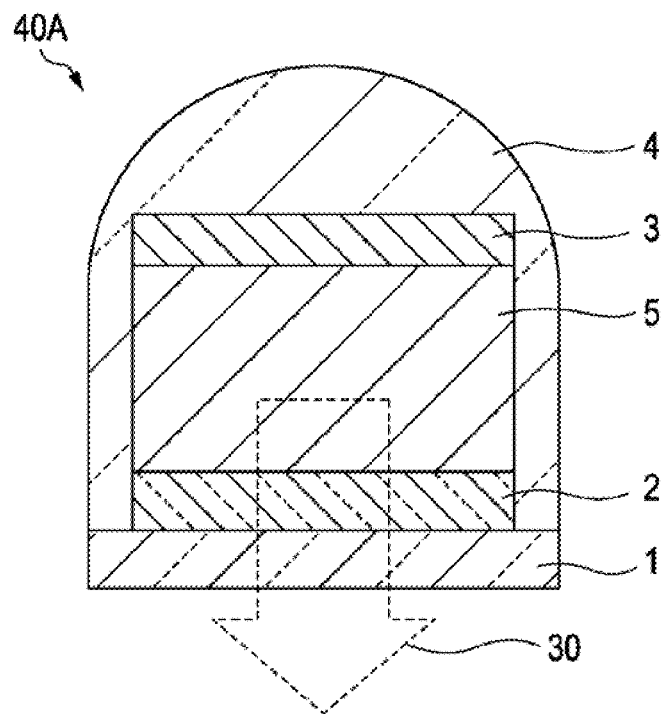
FIG. 1 is a schematic cross-sectional view of a relevant part illustrating an example of a transmission-type organic electroluminescent element according to an embodiment.

According to the aromatic amine compound according to an embodiment, in $X^1$ and $X^2$, the alkyl group may have 1 to 12 carbon atoms when the alkyl group does not have a substituent, and the alkyl group may have a substituent; the aryl group may have 6 to 25 carbon atoms when the aryl group does not have a substituent, and the aryl group may have a substituent; the allyl group may have a substituent; the alkoxy group may have 1 to 12 carbon atoms when the alkoxy group does not have a substituent, and the alkoxy group may have a substituent; the aryloxy group may have 6 to 25 carbon atoms when the aryloxy group does not have a substituent, and the aryloxy group may have a substituent. In addition, $Ar^1$ may have 6 to 25 carbon atoms when $Ar^1$ does not have a substituent, and $Ar^1$ may have a substituent; and $Ar^2$ may have 6 to 25 carbon atoms when $Ar^2$ does not have a substituent. In Y, which is a substituent of $Ar^2$, the alkyl group may have 1 to 12 carbon atoms when the alkyl group does not have a substituent, and the alkyl group may have a substituent; the aryl group may have 6 to 25 carbon atoms when the aryl group does not have a substituent, and the aryl group may have a substituent; the allyl group may have a substituent; the alkoxy group may have 1 to 12 carbon atoms when the alkoxy group does not have a substituent, and the alkoxy group may have a substituent; the aryloxy group may have 6 to 25 carbon atoms when the aryloxy group does not have a substituent, and the aryloxy group may have a substituent. According to this configuration, the aromatic amine compound can be relatively easily synthesized from commercially available reagents in the synthesis, and the molecular weight of the aromatic amine compound can be controlled within an appropriate range. Accordingly, purification in the synthesis can be easily performed.

In general formula [I] above, $X^1$ and $X^2$ may be the same aryl group or different aryl groups and each of $X^1$ and $X^2$ may have a substituent selected from a methyl group, an ethyl group, a n-propyl group, an iso-propyl group, a n-butyl group, an iso-butyl group, a tert-butyl group, a cyclohexyl group, a phenyl group which may have a substituent, a naphthyl group which may have a substituent, an anthranyl group which may have a substituent, and an allyl group which may have a substituent. In addition, preferably, $Ar^1$ is a group selected from general formulae (1) to (44) below. A group represented by general formula [a] below is a group selected from general formulae (45) to (69), and at least one selected from $R^m$s (wherein m is an integer in the range of 456 to 732) of the selected group is a substituent selected from a trifluoromethyl group, a cyano group, and a halogen group. Each of other $R^m$s (wherein m is an integer in the range of 456 to 732) and $R^k$s (wherein k is an integer in the range of 1 to 453) of the selected $Ar^1$ is a group selected from a hydro group, a methyl group, an ethyl group, a n-propyl group, an iso-propyl group, a n-butyl group, an iso-butyl group, a tert-butyl group, a cyclohexyl group, a phenyl group which may have a substituent, a naphthyl group which may have a substituent, an anthranyl group which may have a substituent, an allyl group which may have a substituent, a methoxy group, an ethoxy group, a n-propoxy group, an iso-propoxy group, a n-butoxy group, an iso-butoxy group, a tert-butoxy group, a cyclohexyloxy group, a phenoxy group which may have a substituent, a naphthoxy group which may have a substituent, and an anthranyloxy group which may have a substituent. According to this configuration, since the bulkiness of the molecules is appropriate, the degree of the interaction between molecules is not too strong or too weak. Accordingly, even when a film containing such a compound is formed by vacuum evaporation, spin coating, or the like, concentration quenching by the molecules can be suppressed to increase the efficiency of energy transferred from a host molecule. Therefore, this configuration is advantageous in that the molecules readily sublime when an organic electroluminescent element is produced by vacuum evaporation.

General formula [a]:

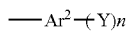

General Formula (1) to (11):

(1)
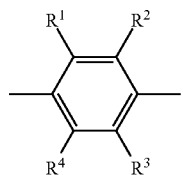

(2)
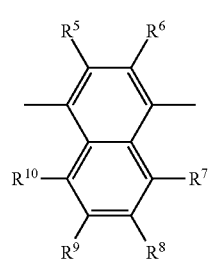

(3)
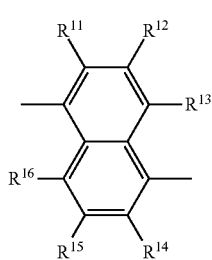

(4)
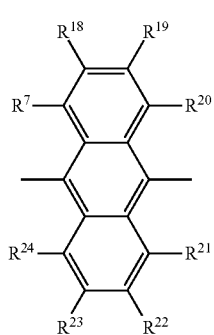

(5)
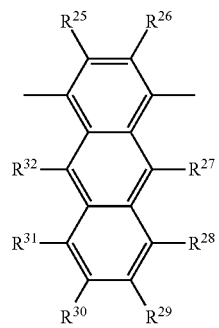

(6)
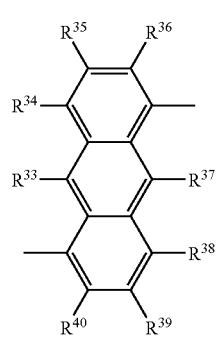

(7)
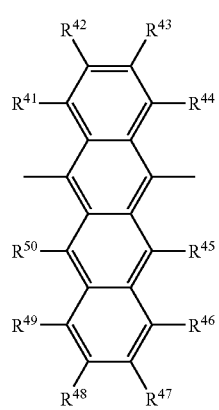

(8)
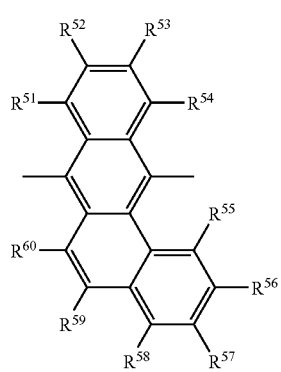

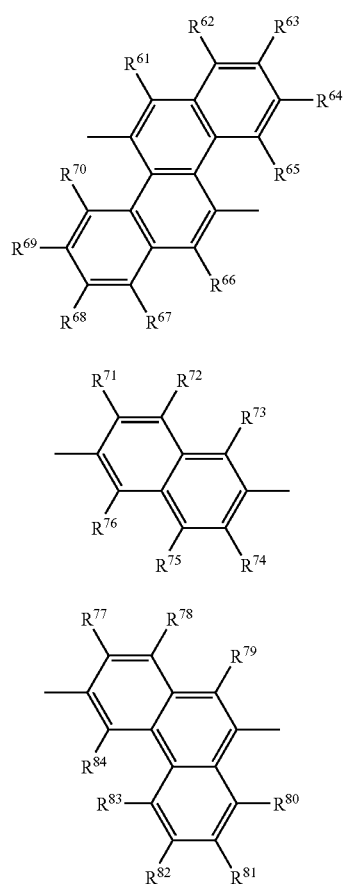
(9)
(10)
(11)
General Formula (12) to (21)
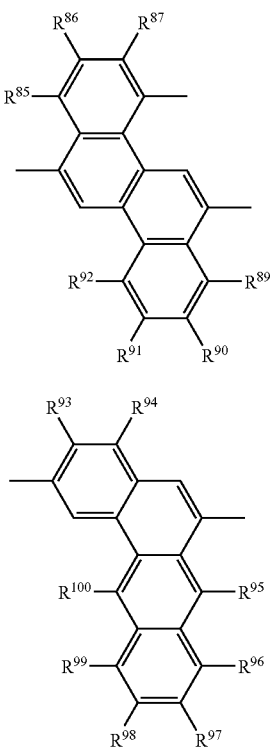
(12)
(13)
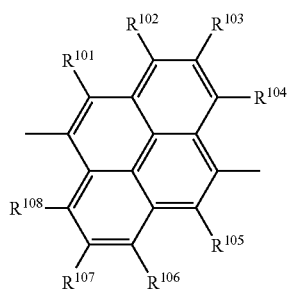
(14)
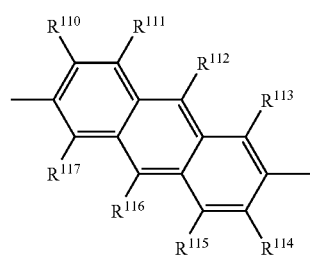
(15)
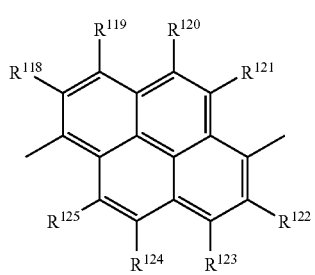
(16)
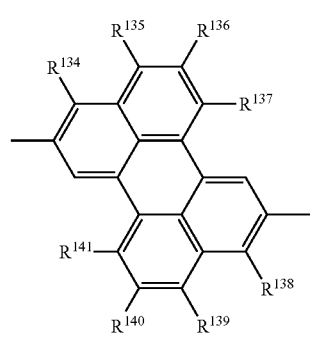
(17)
(18)
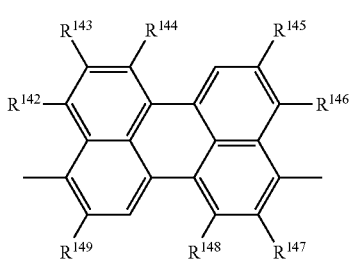
(19)

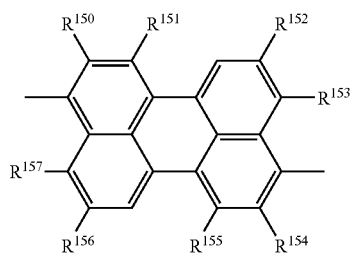
(20)
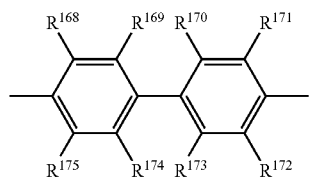
(21)
General Formula (23) to (29)
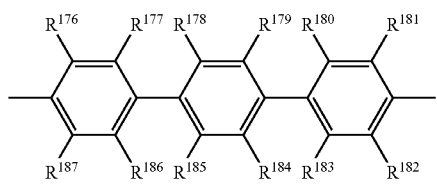
(22)
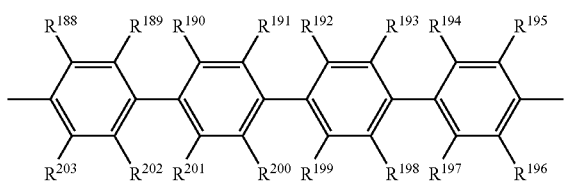
(23)
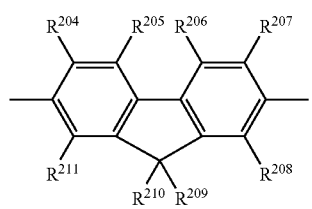
(24)
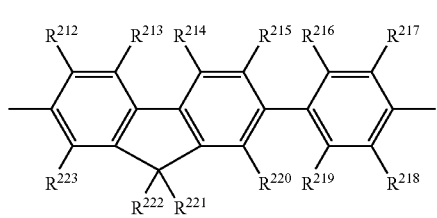
(25)
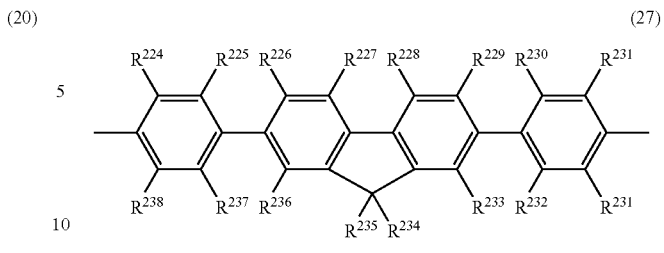
(26)
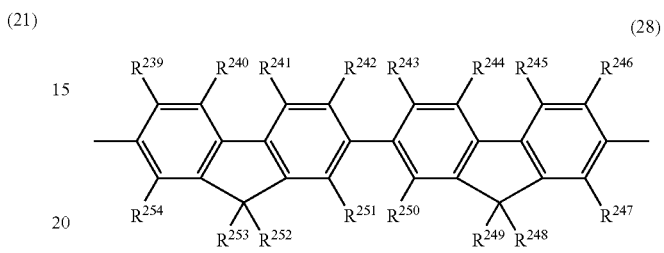
(27)
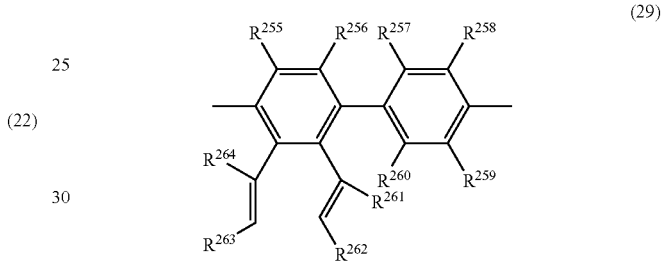
(28)
General Formula (30) to (39)
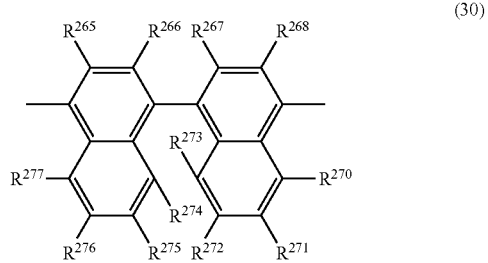
(29)
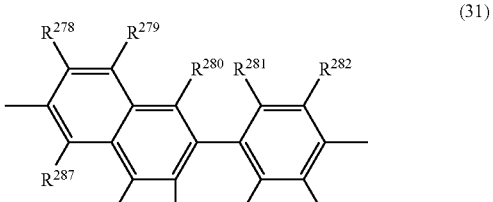
(30)
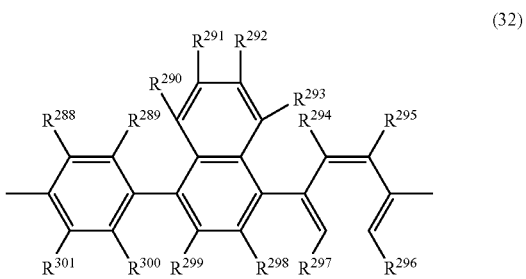
(31)
(32)

(33)
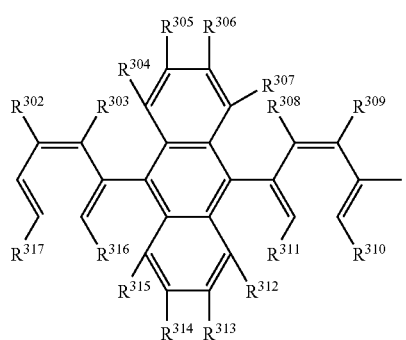
(34)
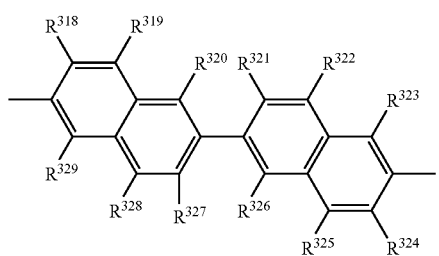
(35)
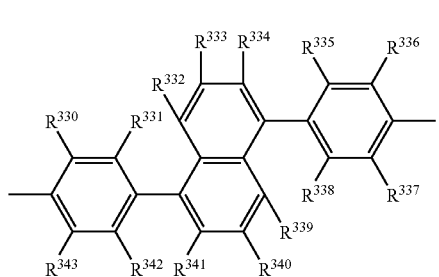
(36)
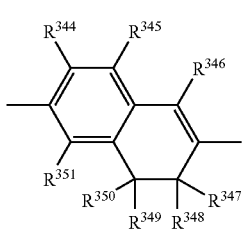
(37)
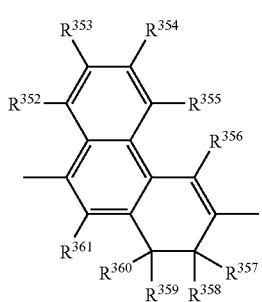
General Formula (38) to (47)
(38)
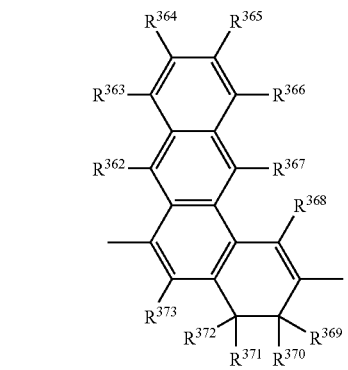
(39)
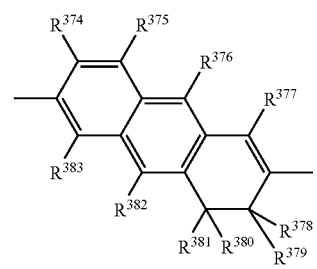
(40)
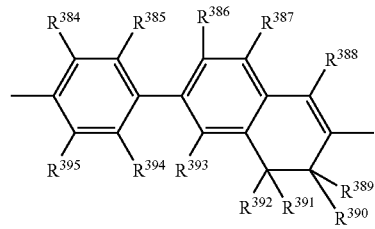
(41)
(42)
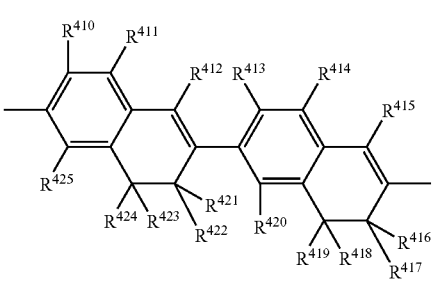

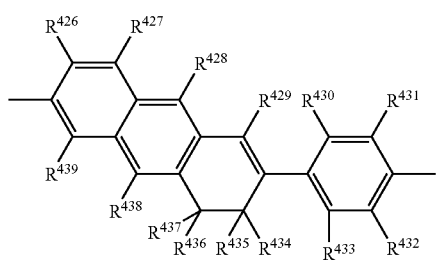
(43)
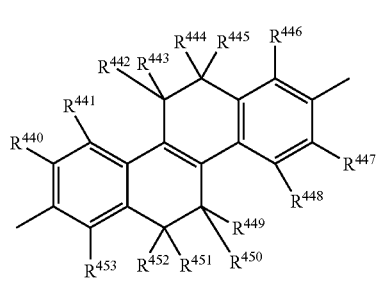
(44)
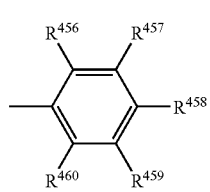
(45)
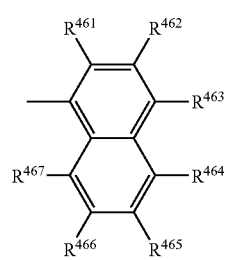
(46)
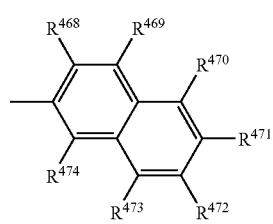
(47)
General Formula (48) to (55)
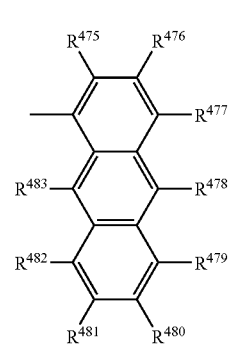
(48)
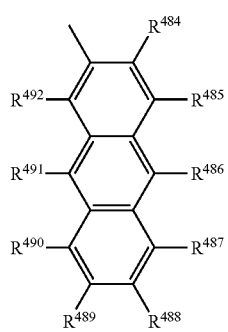
(49)
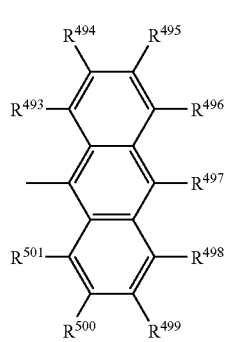
(50)
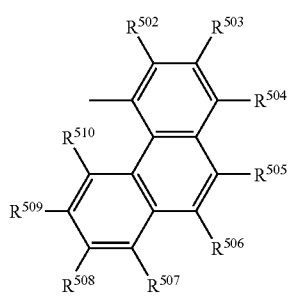
(51)
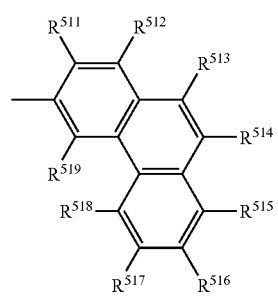
(52)
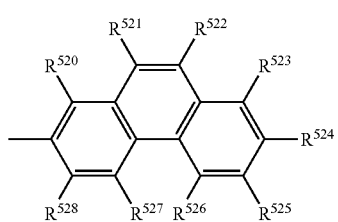
(53)

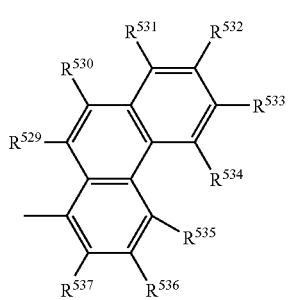
(54)
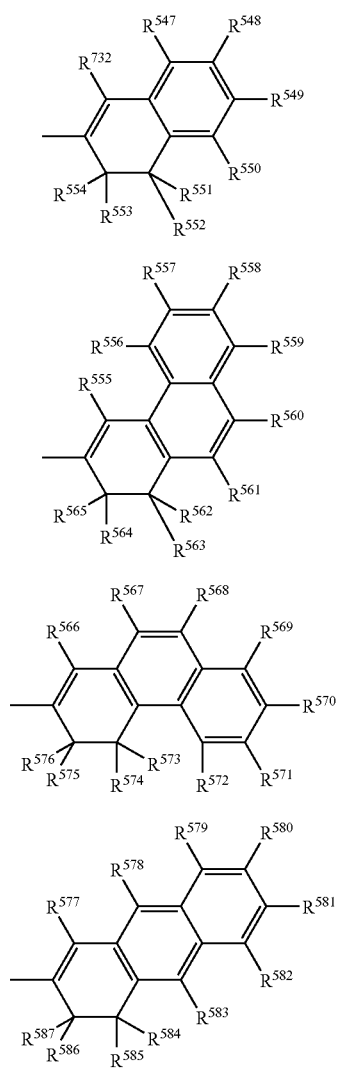
General Formula (56) to (64)
(55)
(56)
(57)
(58)
(59)
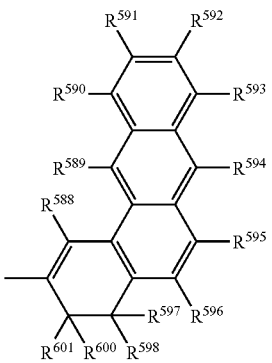
(60)
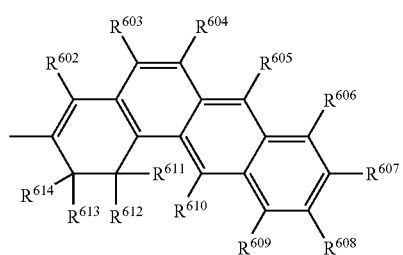
(61)
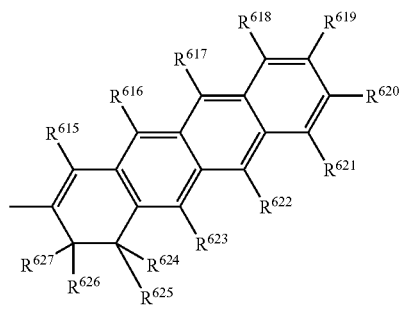
(62)
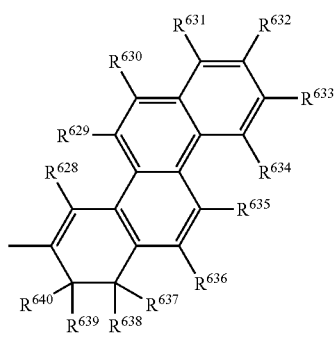
(63)
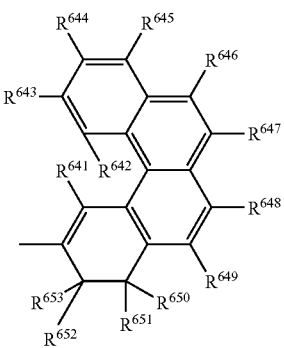
(64)

General Formula (65) to (69)

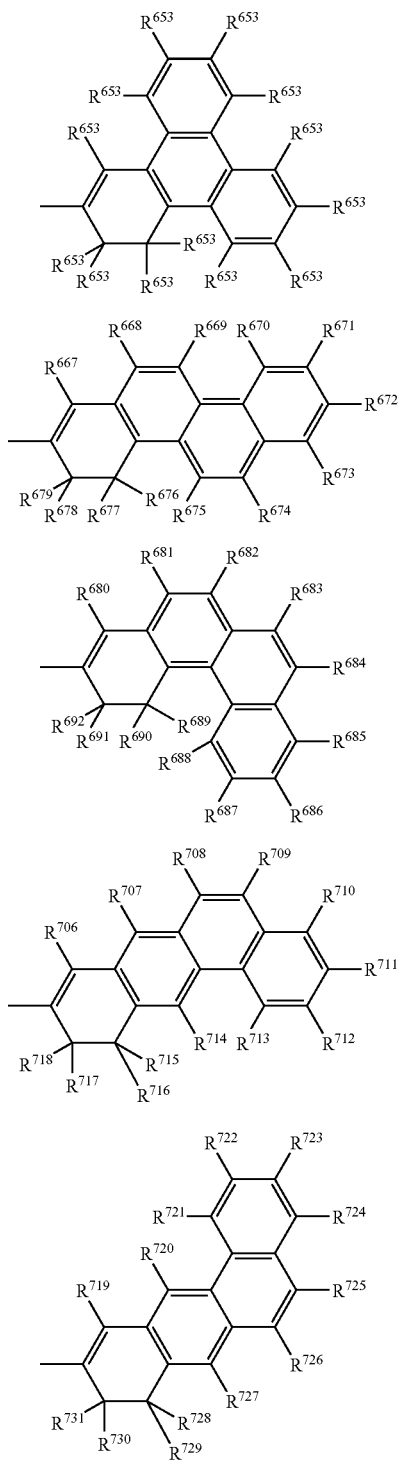

(65)
(66)
(67)
(68)
(69)

In addition, each of $R^k$s (wherein k is an integer in the range of 1 to 453) of $Ar^1$ is preferably a hydro group, and two of $R^m$s (wherein m is an integer in the range of 456 to 732) of the group represented by general formula [a] are each preferably a group selected from a trifluoromethyl group, a cyano group, and a halogen group. According to this configuration, an electron-withdrawing property of the group represented by general formula [a] is increased, and thus the group represented by general formula [a] has an acceptor property. Consequently, an electron transfer from the amine moiety having a donor property to the group represented by general formula [a] occurs, thereby easily forming a charge transfer state in which the polarizability of the molecule is large. The charge transfer state of the compound represented by general formula [I] is a fluorescent exciplex. The wavelength of fluorescence from the exciplex is longer than that of fluorescence from the individual donor moiety or acceptor moiety, which is a constituent of the compound. That is, by adjusting the donor property of the amine moiety or the acceptor property of the group represented by general formula [a], fluorescence of the compound represented by general formula [I] can be shifted to red.

In general formula [I], $X^1$ is preferably a phenyl group, $X^2$ is preferably a 2-naphthyl group, $Ar^1$ is preferably a 2,6-naphthylene group, and a group represented by general formula [a] below is preferably a 3-phenanthryl group having cyano groups at the 9-position and the 10-position and a methyl group at the 6-position. Specifically, the aromatic amine compound represented by general formula [I] is preferably a tertiary amine compound represented by formula [Ia] below. According to this configuration, a material having a fluorescence maximum in the range of 580 to 650 nm, which is the most suitable for a red-light-emitting material, can be obtained on the basis of the above-described principle.

General formula [a]:

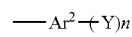

Formula [Ia]:

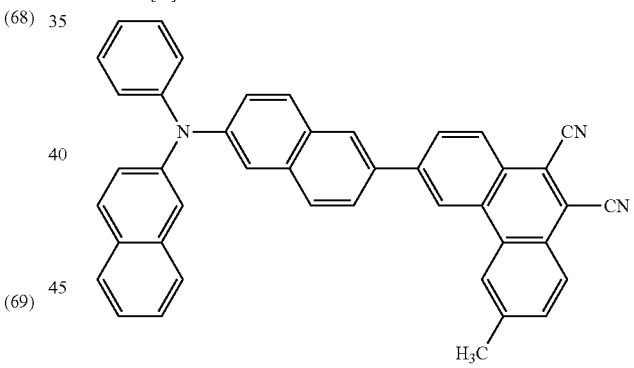

Alternatively, in general formula [I], $X^1$ is preferably a phenyl group, $X^2$ is preferably a 1-naphthyl group, $Ar^1$ is preferably a 2,6-naphthylene group, and a group represented by general formula [a] below is preferably a 2-anthryl group having cyano groups at the 9-position and the 10-position. Specifically, the aromatic amine compound represented by general formula [I] is preferably a tertiary amine compound represented by formula [Ib] below. According to this configuration, a material having a fluorescence maximum in the range of 630 to 700 nm, which is the most suitable for a red-light-emitting material, can be obtained on the basis of the above-described principle.

General formula [a]:

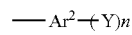

Formula [Ib]:

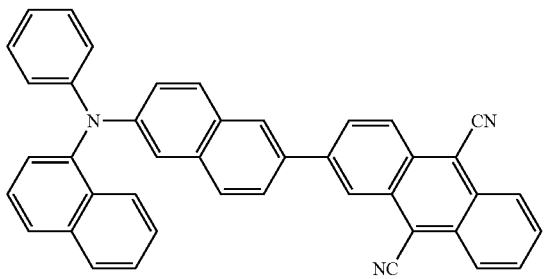

In the organic electroluminescent element according to an embodiment, the organic layer preferably has a structure in which a hole-transporting layer and an electron-transporting layer are stacked. According to this configuration, injection barriers of holes and electrons can be decreased.

At least the hole-transporting layer is preferably the amine-compound-containing layer. According to this configuration, the injection barrier of holes from a hole transport material layer to the amine-compound-containing layer can be minimized.

At least the electron-transporting layer is preferably the amine-compound-containing layer. According to this configuration, the injection barrier of electrons from an electron transport material layer to the amine-compound-containing layer can be minimized.

Alternatively, the organic layer preferably has a structure in which a hole-transporting layer, a light-emitting layer, and an electron-transporting layer are stacked. According to this configuration, holes from the hole-transporting layer and electrons from the electron-transporting layer are confined in the light-emitting layer, and recombination of the holes and the electrons efficiently occurs. Consequently, the luminous efficiency can be maximized.

At least the light-emitting layer is preferably the amine-compound-containing layer. According to this configuration, both the hole mobility and the electron mobility in the light-emitting layer are high, and thus a resistance component of the light-emitting layer can be minimized.

The light-emitting layer is preferably the amine-compound-containing layer containing the dopant material and a host material, and the host material is preferably a compound having an anthracene skeleton. According to this configuration, recombination occurs in the anthracene host molecules in which the recombination probability of holes from the hole-transporting layer and electrons from the electron-transporting layer is high, and energy of the recombination is transferred to dopant molecules. Accordingly, instead of blue fluorescence of the anthracene host material, a red-light emission due to the dopant material can be obtained with a high efficiency.

The content of the dopant material contained in the amine-compound-containing layer is preferably 50% or less. According to this configuration, concentration quenching by the dopant material can be suppressed.

In the display device according to an embodiment, the control unit preferably includes a switching element. According to this configuration, the display device can be used as a display device configured to display moving images.

An embodiment relates to an organic electroluminescent element A including an anode, a cathode, and an organic layer disposed between the anode and the cathode, in which at least one layer constituting the organic layer is a mixed layer containing at least one of the above-mentioned aromatic amine compounds and at least one of anthracene derivative compounds represented by formula [IIa] to formula [IIe]. This embodiment can provide a highly reliable organic electroluminescent element that emits bright red light with a high efficiency and low power consumption.

Formula [IIa]:

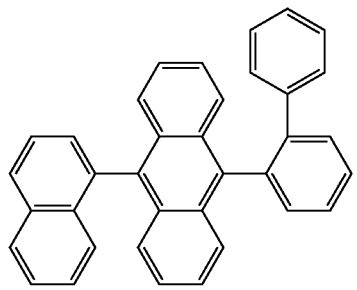

Formula [IIb]: 9,10-Di(3-fluoranthenyl)anthracene

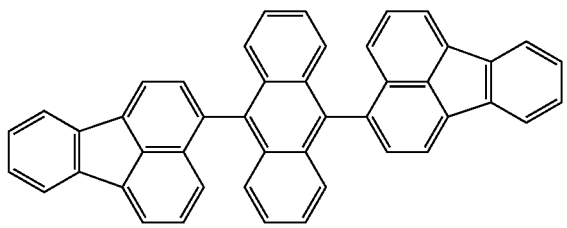

Formula [IIc]: 9,10-Di(2-naphthyl)anthracene

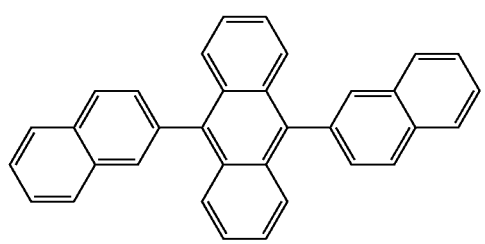

Formula [IId]:

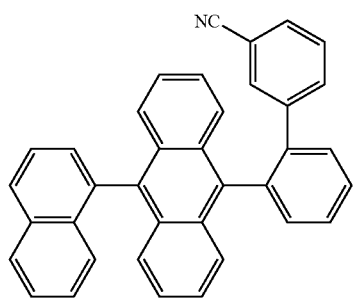

Formula [IIe]:

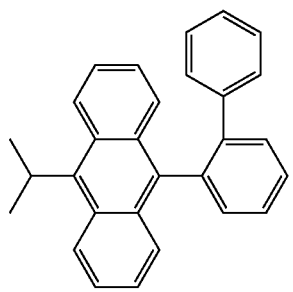

In the organic electroluminescent element A, the organic layer preferably has a structure in which a hole-transporting layer and an electron-transporting layer are stacked. This configuration is referred to as "configuration (a)". According to this configuration, injection barriers of holes and electrons can be decreased.

In configuration (a), at least the hole-transporting layer is preferably composed of the mixed layer. According to this configuration, the injection bather of holes from a hole transport material layer to the amine compound layer can be minimized.

In configuration (a), at least the electron-transporting layer is preferably composed of the mixed layer. According to this configuration, the injection bather of electrons from an electron transport material layer to the amine compound layer can be minimized.

In the organic electroluminescent element A, the organic layer preferably has a structure in which a hole-transporting layer, a light-emitting layer, and an electron-transporting layer are stacked. This configuration is referred to as "configuration (b)". According to this configuration, holes from the hole-transporting layer and electrons from the electron-transporting layer are confined in the light-emitting layer, and recombination of the holes and the electrons efficiently occurs. Consequently, the luminous efficiency can be maximized.

In configuration (b), the light-emitting layer is preferably composed of the mixed layer. According to this configuration, both the hole mobility and the electron mobility in the light-emitting layer are high, and thus a resistance component of the light-emitting layer can be minimized.

The light-emitting layer is preferably composed of a host material and a dopant material, and the aromatic amine compound is preferably contained as the dopant material. According to this configuration, recombination occurs in the host molecules in which the recombination probability of holes from the hole-transporting layer and electrons from the electron-transporting layer is high, and energy of the recombination is transferred to dopant molecules. Accordingly, instead of fluorescence of the host material, red-shifted light emission due to the dopant material can be obtained with a high efficiency.

In the anthracene derivative compounds represented by formula [IIa] to formula [IIe], the hydrogen atom at the 9-position of an anthracene ring thereof is substituted with any of a 1-naphthyl group, a 3-fluoranthenyl group, a 2-naphthyl group, and an isopropyl group. The hydrogen atom at the 10-position of the anthracene ring is substituted with any of a phenyl group, a 3-fluoranthenyl group, and a 2-naphthyl group.

Each of hydrogen atoms at the 1-position to the 8-position of the anthracene ring of the anthracene derivative compounds represented by formula [IIa] to formula [IIe] may be substituted with a group selected from a trifluoromethyl group; a cyano group; a halogen group; an alkyl group which has 1 to 12 carbon atoms and which may have a substituent; an aryl group which has 5 to 25 carbon atoms, which may have a substituent, and which may contain a heteroatom as a constituent of the ring; an allyl group which may have a substituent; an alkoxy group which has 1 to 12 carbon atoms and which may have a substituent; and an aryloxy group which has 6 to 25 carbon atoms and which may have a substituent.

Each of hydrogen atoms of a first phenyl group bonded to the 10-position of the anthracene ring and each of hydrogen atoms of a second phenyl group bonded by substituting a hydrogen atom of the first phenyl group may be substituted with a group selected from a trifluoromethyl group; a cyano group; a halogen atom; an alkyl group which has 1 to 12 carbon atoms and which may have a substituent; an aryl group which has 6 to 25 carbon atoms, which may have a substituent, and which may contain a heteroatom as a constituent of the ring; an allyl group which may have a substituent; an alkoxy group which has 1 to 12 carbon atoms and which may have a substituent; and an aryloxy group which has 6 to 25 carbon atoms and which may have a substituent. In such a case, adjacent groups may be combined to form a ring.

Furthermore, each of hydrogen atoms of the fluoranthenyl groups and the naphthyl groups bonded to the anthracene ring may be substituted with a substituent.

Aromatic amine compounds according to embodiments and anthracene derivative compounds (host compounds) used by mixing with the aromatic amine compounds will now be described.

[Structure of Aromatic Amine Compound]

An aromatic amine compound according to an embodiment is represented by general formula [I] above and is a compound obtained by bonding a divalent group $Ar^1$ selected from general formulae (1) to (44) above and a monovalent group represented by general formula [a] above and selected from general formulae (45) to (69) above.

In this specification, an aryl group refers to a group formed by abstracting one hydrogen atom from an aromatic hydrocarbon, and an arylene group refers to a group formed by abstracting one hydrogen atom from an aryl group. Aromatic hydrocarbons (arenes) refer to monocyclic or polycyclic hydrocarbons that exhibit aromaticity, and some of a plurality of hydrogen atoms thereof may be substituted. That is, the aromatic hydrocarbons (arenes) refer to aromatic compounds having a single aromatic ring or a plurality of aromatic rings. The plurality of rings that exhibit aromaticity may constitute an acene or polyacene in which a plurality of monocycles are linearly bonded without condensation, or a fused ring in which two or more rings are bonded by sharing two or more carbon atoms. The aryl group also includes groups produced by abstracting one hydrogen atom from a heterocyclic compound (compound containing, in addition to carbon atoms (C), heteroatoms such as an oxygen atom (O), a nitrogen atom (N), and a sulfur atom (S) as atoms constituting a ring) that is constituted by a single ring or a plurality of rings and that exhibits aromaticity.

In the aromatic amine compound (represented by general formula [I] above) according to an embodiment of the present invention, $X^1$ and $X^2$ are the same group or different groups and each of $Ar^1$ and $Ar^2$ is an arylene group. $Ar^1$ may be substituted with a group selected from an alkyl group ($-C_nH_{2n+1}$), an aryl group, an allyl group ($-CH_2CH=CH_2$), an alkoxy group ($-OC_nH_{2n+1}$), and an aryloxy group ($-OAr$ wherein Ar represents an aryl group). $Ar^2$ has at least one or more substituents Y, and at least one of the substituents Y is a group selected from a trifluoromethyl group ($-CF_3$), a cyano group ($-CN$), and a halogen group (halo group such as $-F$, $-Cl$, $-Br$, and $-I$), and other substituents Y are groups each selected from a hydro group ($-H$), an alkyl group ($-C_nH_{2n+1}$), an aryl group, an allyl group ($-CH_2CH=CH_2$), an alkoxy group ($-OC_nH_{2n+1}$), and an aryloxy group ($-OAr$ wherein Ar represents an aryl group).

Each of $X^1$ and $X^2$ is selected from a hydro group, an alkyl group, an aryl group, an allyl group, an alkoxy group, and an aryloxy group. Each of $Ar^1$ and $Ar^2$ is an arylene group which has 6 to 25 carbon atoms when $Ar^1$ and $Ar^2$ do not have a substituent, and which may have a substituent.

Each of $Ar^1$ and $Ar^2$ is an arylene group selected from, for example, a phenylene group, ($-C_6H_4-$), a naphthylene group (—$C_{10}H_6$—), an anthrylene group (—$C_{14}H_8$—), and a phenanthrylene group (—$C_{14}H_8$—).

$Ar^2$ has at least one substituent Y selected from a trifluoromethyl group (—$CF_3$), a cyano group (—CN), and a halogen group (halo group such as —F, —Cl, —Br, and —I). Furthermore, $Ar^2$ may have a substituent Y selected from an alkyl group, an aryl group, an allyl group, an alkoxy group, and an aryloxy group.

$Ar^1$ and $X^1$ and/or $Ar^2$ and $X^2$ may be combined to form a ring. Alternatively, $Ar^1$ and $Ar^2$ may be combined to form a ring.

In $X^1$ and $X^2$, the alkyl group and the alkoxy group have 1 to 12 carbon atoms when the alkyl group and the alkoxy group do not have a substituent, and the aryl group and the aryloxy group have 6 to 25 carbon atoms when the aryl group and the aryloxy group do not have a substituent. Each of the alkyl group, the aryl group, the allyl group, the alkoxy group, and the aryloxy group may have a substituent.

$X^1$ and $X^2$ may be the same aryl group or different aryl groups and may have a substituent selected from a methyl group (—$CH_3$), an ethyl group (—$CH_2CH_3$), a n-propyl group (—$(CH_2)_2CH_3$), an iso-propyl group (—$CH(CH_3)_2$), a n-butyl group (—$(CH_2)_3CH_3$), an iso-butyl group (—$CH_2CH(CH_3)_2$), a tert-butyl group (—$(CH_3)_3$), a sec-butyl group (—$CH(CH_3)CH_2CH_3$), a cyclohexyl group (—$C_6H_{11}$), a phenyl group (—$C_6H_5$), a naphthyl group (—$C_{10}H_7$), an anthranyl (anthryl) group (—$C_{14}H_9$), a phenanthryl group (—$C_{14}H_9$), and an allyl group.

The phenyl group, the naphthyl group, the anthranyl group, the phenanthryl group, and the allyl group may have a substituent.

In the monovalent group represented by general formula [a] above, $Ar^2$ has 6 to 25 carbon atoms when $Ar^2$ does not have a substituent and has at least one or more substituents Y. At least one of the substituents Y is a substituent selected from a trifluoromethyl group, a cyano group, and a halogen group, and other substituents Y are groups each selected from a hydro group, an alkyl group, an aryl group, an allyl group, an alkoxy group, and an aryloxy group. The alkyl group and the alkoxy group have 1 to 12 carbon atoms when the alkyl group and the alkoxy group do not have a substituent, and the aryl group and the aryloxy group have 6 to 25 carbon atoms when the aryl group and the aryloxy group do not have a substituent. Each of the alkyl group, the aryl group, the allyl group, the alkoxy group, and the aryloxy group may have a substituent.

[Divalent Group (—$Ar^1$—) in Aromatic Amine Compound]

$Ar^1$ is a group selected from general formulae (1) to (44) above, and the monovalent group represented by general formula [a] above is a group selected from general formulae (45) to (69) above.

Each of the substituents Y of $Ar^2$ is one selected from $R'''$s (wherein m is an integer in the range of 456 to 732) of the monovalent group selected from general formulae (45) to (69) and represented by general formula [a].

The divalent group $Ar^1$ represented by any of general formulae (1) to (44) is a divalent group formed by abstracting two hydrogen atoms from a parent compound which is selected from aromatic compounds (including a plurality of isomeric structures) and derivatives thereof. Note that a plurality of divalent groups having different isomeric structures are present as the divalent group (—$Ar^1$—) depending on the positions of the hydrogen atoms abstracted from the parent compound.

Examples of aromatic hydrocarbons serving as the parent compound include benzene ($C_6H_6$), naphthalene ($C_{10}H_8$), anthracene ($C_{14}H_{10}$), phenanthrene ($C_{14}H_{10}$), tetracene (naphthacene) ($C_{18}H_{12}$), tetraphene (naphthoanthracene) ($C_{18}H_{12}$), chrysene ($C_{18}H_{12}$), pyrene ($C_{16}H_{10}$), perylene ($C_{20}H_{12}$), biphenyl ($C_{12}H_{10}$), terphenyl ($C_{18}H_{14}$), quaterphenyl ($C_{24}H_{18}$), 9H-fluorene ($C_{13}H_{10}$), phenyl-9H-fluorene ($C_{19}H_{14}$), diphenyl-9H-fluorene ($C_{25}H_{18}$), bi-[9H-fluorene] ($C_{26}H_{18}$), phenylnaphthalene ($C_{16}H_{12}$), diphenylnaphthalene ($C_{22}H_{16}$), diphenylanthracene ($C_{26}H_{18}$), binaphthalene ($C_{20}H_{14}$), and bianthracene ($C_{28}H_{18}$).

Next, general formulae (1) to (44) will be described using unsubstituted divalent aromatic hydrocarbon groups (—$Ar^1$—) as examples.

(1): a p-phenylene group, (2): a 1,4-naphthylene group, (3): a 1,5-naphthylene group, (4): a 9,10-anthrylene group, (5): a 1,4-anthrylene group, (6): a 1,5-anthrylene group, (7): a 6,11-naphthacenylene group, (8): a group formed by abstracting hydrogen atoms at the 7-position and the 2-position of benz[a]anthracene ($C_{18}H_{12}$), (9): a 5,11-chrysenylene group, (10): a 2,6-naphthylene group, (11): a 6,10-phenanthrylene group, (12): a 6,12-chrysenylene group, (13): a group formed by abstracting hydrogen atoms at the 2-position and the 6-position of benz[a]anthracene, (14): a 4,9-pyrenylene group, (15): a 2,6-anthrylene group, (16): a 1,6-pyrenylene group, (17): a 2,7-phenanthrylene group, (18): a 5,11-perylenylene group, (19): a 1,6-perylenylene group, (20): a 1,7-perylenylene group, (21): a group formed by abstracting hydrogen atoms at the 5-position and the 10-position of benz[a]anthracene, (22): a 4,4'-biphenylene group, (23): a 4,4'-terphenylene group, (24): a 4,4'-quaterphenylene group, (25): a 2,7-fluorenylene group, (26): a group formed by abstracting hydrogen atoms at the 7-position of 9H-fluorene and the 4-position of a phenyl group of 2-phenyl-9H-fluorene ($C_{19}H_{14}$), (27): a group formed by abstracting hydrogen atoms at the 4-positions of two phenyl groups of 2,7-diphenyl-9H-fluorene ($C_{25}H_{18}$), (28): a group formed by abstracting hydrogen atoms at the 7-position and the 7'-position of 2,2'-bi[9H-fluorene] ($C_{26}H_{18}$), (29): a group formed by abstracting hydrogen atoms at the 4-position of naphthalene and the 4-position of a phenyl group of 1-phenylnaphthalene ($C_{16}H_{12}$), (30): a group formed by abstracting hydrogen atoms at the 4-position and the 4'-position of 1,1'-binaphthalene ($C_{20}H_{14}$), (31): a group formed by abstracting hydrogen atoms at the 6-position of naphthalene and the 4-position of a phenyl group of 2-phenylnaphthalene ($C_{16}H_{12}$), (32): a group formed by abstracting hydrogen atoms at the 4-positions of two phenyl groups of 1,4-diphenylnaphthalene ($C_{22}H_{16}$), (33) a group formed by abstracting hydrogen atoms at the 4-positions of two phenyl groups of 9,10-diphenylanthracene ($C_{26}H_{18}$), (34): a group formed by abstracting hydrogen atoms at the 6-position and the 6'-position of 2,2'-binaphthalene ($C_{20}H_{14}$), (35): a group formed by abstracting hydrogen atoms at the 4-positions of two phenyl groups of 1,5-diphenylnaphthalene ($C_{22}H_{16}$), (36): a group formed by abstracting hydrogen atoms at the 3-position and the 7-position of 1,2-dihydronaphthalene ($C_{10}H_{10}$), (37): a group formed by abstracting hydrogen atoms at the 3-position and the 9-position of 1,2-dihydrophenanthrene ($C_{14}H_{12}$), (38): a group formed by abstracting hydrogen atoms at the 2-position and the 6-position of 3,4-dihydrobenz[a]anthracene ($C_{18}H_{14}$), (39): a group formed by abstracting hydrogen atoms at the 3-position and the 7-position of 1,2-dihydroanthracene ($C_{14}H_{12}$) (40) a group formed by abstracting hydrogen atoms at the 3-position of naphthalene and the 4-position of a phenyl group of 7-phenyl-1,2-dihydronaphthalene ($C_{16}H_{14}$), (41): a group formed by abstracting hydrogen atoms at the 6-position of a naphthyl group and the 7-position of dihydronaphthalene of 3-(2-naphthyl)-1,2-dihydronaphthalene ($C_{20}H_{16}$), (42): a group formed by abstracting hydrogen atoms at the 7-position of a dihydronaphthyl group and the 3-position of dihydronaphthalene of 3-(1,2-dihydronaphthyl)-1,2-dihydronaphthalene ($C_{20}H_{18}$), (43): a group formed by abstracting hydrogen atoms at the 4-position of a phenyl group and the 7-position of dihydroanthracene of 3-phenyl-1,2-dihydroanthracene ($C_{20}H_{16}$), and (44): 5,6,11,12-tetrahydrorochrysene ($C_{18}H_{16}$).

The above-described (1) to (44) are unsubstituted divalent aromatic hydrocarbon groups (—$Ar^1$—) in general formulae (1) to (44). Groups in which hydro groups (—H) in the divalent aromatic hydrocarbon groups described in (1) to (44) above are substituted with substituents Rs are the groups represented by general formulae (1) to (44).

[Monovalent Group Represented by General Formula [a] in Aromatic Amine Compound]

A group represented by general formula [a] above is a group selected from general formulae (45) to (69) above. At least one selected from $R^m$s (wherein m is an integer in the range of 456 to 732) of the selected group is a substituent selected from a trifluoromethyl group, a cyano group, and a halogen group. Each of other $R^m$s (wherein m is an integer in the range of 456 to 732) is a group selected from a hydro group, a methyl group, an ethyl group, a n-propyl group, an iso-propyl group, a n-butyl group, an iso-butyl group, a tert-butyl group, a cyclohexyl group, a phenyl group which may have a substituent, a naphthyl group which may have a substituent, an anthranyl group which may have a substituent, an allyl group which may have a substituent, a methoxy group, an ethoxy group, a n-propoxy group, an iso-propoxy group, a n-butoxy group, an iso-butoxy group, a tert-butoxy group, a cyclohexyloxy group, a phenoxy group which may have a substituent, a naphthoxy group which may have a substituent, and an anthranyloxy group which may have a substituent.

The group represented by general formula [a] is a group formed by abstracting one hydrogen atom from a parent compound which is selected from aromatic compounds (including a plurality of isomeric structures) and derivatives thereof. Note that a plurality of groups having different isomeric structures are present as the monovalent group depending on the position of the hydrogen atom abstracted from the parent compound.

Examples of aromatic hydrocarbons serving as the parent compound include benzene ($C_6H_6$), naphthalene ($C_{10}H_8$), anthracene ($C_{14}H_{10}$), phenanthrene ($C_{14}H_{10}$), tetracene (naphthacene) ($C_{18}H_{12}$), tetraphene (naphthoanthracene) ($C_{18}H_{12}$), chrysene ($C_{18}H_{12}$), 3,4-bennzophenanthrene ($C_{18}H_{12}$), and triphenylene (9,10-benzophenanthrene, $C_{18}H_{12}$).

Next, monovalent groups represented by general formula [a] and represented by general formulae (45) to (69) will be described using unsubstituted monovalent aromatic hydrocarbon groups as examples.

(45): a phenyl group, (46): a 1-naphthyl group, (47): a 2-naphthyl group, (48): a 1-anthryl group, (49): a 2-anthryl group, (50): a 9-anthryl group, (51): a 4-phenanthry group, (52): a 3-phenanthry group, (53): a 2-phenanthry group, (54): a 1-phenanthry group, (55): a 9-phenanthry group, (56): a group formed by abstracting a hydrogen atom at the 3-position of 1,2-dihydronaphthalene ($C_{10}H_{10}$), (57): a group formed by abstracting a hydrogen atom at the 3-position of 1,2-dihydrophenanthrene ($C_{14}H_{12}$), (58): a group formed by abstracting a hydrogen atom at the 2-position of 3,4-dihydrophenanthrene ($C_{14}H_{12}$), (59): a group formed by abstracting a hydrogen atom at the 3-position of 1,2-dihydroanthracene ($C_{14}H_{12}$), (60): a group formed by abstracting a hydrogen atom at the 2-position of 3,4-dihydrobenz[a]anthracene ($C_{18}H_{14}$), (61): a group formed by abstracting a hydrogen atom at the 3-position of 1,2-dihydrobenz[a]anthracene ($C_{18}H_{14}$), (62): a group formed by abstracting a hydrogen atom at the 3-position of 1,2-dihydronaphthacene ($C_{18}H_{14}$), (63): a group formed by abstracting a hydrogen atom at the 3-position of 1,2-dihydrochrysene ($C_{18}H_{14}$), (64): a group formed by abstracting a hydrogen atom at the 5-position of 3,4-dihydrobenz[c]anthracene ($C_{18}H_{14}$), (65): a group formed by abstracting a hydrogen atom at the 3-position of 1,2-dihydrotriphenylene ($C_{18}H_{14}$), (66): a group formed by abstracting a hydrogen atom at the 2-position of 3,4-dihydrochrysene ($C_{18}H_{14}$), (67): a group formed by abstracting a hydrogen atom at the 4-position of 5,6-dihydrobenz[c]anthracene ($C_{18}H_{14}$) (68): a group formed by abstracting a hydrogen atom at the 9-position of 10,11-dihydrobenz[a]anthracene ($C_{18}H_{14}$), and (69): a group formed by abstracting a hydrogen atom at the 10-position of 8,9-dihydrobenz[a]anthracene ($C_{18}H_{14}$).

The above-described (45) to (69) are unsubstituted monovalent aromatic hydrocarbon groups in general formulae (45) to (69) above. Groups in which hydro groups (—H) in the monovalent aromatic hydrocarbon groups described in (45) to (69) above are substituted with substituents R are the groups represented by general formulae (45) to (69).

Each of the divalent group (—$Ar^1$—) and the monovalent group (the group represented by general formula [a]) may be a group formed by abstracting one hydrogen atom or two hydrogen atoms from a parent compound other than the parent compounds described above. For example, each of the groups may be a group (including groups having a plurality of isomeric structures) formed by abstracting one hydrogen atom or two hydrogen atoms from any of the following parent compounds.

Examples of the parent compounds include pentalene ($C_8H_6$), benzocyclobutene ($C_8H_6$), 1H-indene ($C_9H_8$), azulene ($C_{10}H_8$), acenaphthylene ($C_{12}H_8$), indacene ($C_{12}H_8$), biphenylene ($C_{12}H_8$), heptalene ($C_{12}H_{10}$), phenalene (peri-benzonaphthalene), ($C_{13}H_{10}$), aceanthrylene ($C_{16}H_{10}$), phenylnaphthalene ($C_{16}H_{12}$), acephenanthrylene ($C_{16}H_{10}$), pentacene ($C_{22}H_{14}$), benznaphthacene ($C_{22}H_{14}$), picene ($C_{22}H_{14}$), benzochrysene ($C_{22}H_{14}$), dibenzanthracene ($C_{22}H_{14}$), dibenzphenanthrene ($C_{22}H_{14}$), dibenzopyrene ($C_{24}H_{12}$), ternaphthalene ($C_{30}H_{20}$), quaternaphthalene ($C_{40}H_{26}$), teranthracene ($C_{42}H_{26}$), and quateranthracene ($C_{56}H_{34}$).

[Substituent R]

Each of $R^k$s (wherein k is an integer in the range of 1 to 453) of $Ar^1$ selected from general formulae (1) to (44), $R^m$s (wherein m is an integer in the range of 456 to 732) of a monovalent group selected from general formulae (45) to (69), and the substituents Y of $Ar^2$ is a group selected from the following groups. Note that at least one of the substituents Y of $Ar^2$ is a group selected from a trifluoromethyl group, a cyano group, and a halogen group.

Specifically, each of the above groups is selected from a hydro group, a methyl group, an ethyl group, a n-propyl group, an iso-propyl group, a n-butyl group, an iso-butyl group, a tert-butyl group, a sec-butyl group, a cyclohexyl group, a phenyl group, a naphthyl group, an anthranyl group, a phenanthryl group, an allyl group, a methoxy group (—$OCH_3$), an ethoxy group (—$OCH_2CH_3$), a n-propoxy group (—$O(CH_2)_2CH_3$), an iso-propoxy group (—$OCH(CH_3)_2$), a n-butoxy group (—$O(CH_2)_3CH_3$), an iso-butoxy group (—$OCH_2CH(CH_3)_2$), a tert-butoxy group (—$OC(CH_3)_3$), a sec-butoxy group (—$OCH(CH_3)CH_2CH_3$), a cyclohexyloxy group (—$OC_6H_{11}$), a phenoxy group (—$OC_6H_5$), a naphthoxy group (—$OC_{10}H_7$), an anthranyloxy (anthryloxy) group, (—$OC_{14}H_9$), and a phenanthryloxy group (—$OC_{14}H_9$).

Here, the phenyl group, the naphthyl group, the anthranyl group, the phenanthryl group, the allyl group, the phenoxy group, the naphthoxy group, the anthranyloxy group, and the phenanthryloxy group may have a substituent.

All the $R^k$s (wherein k is an integer in the range of 1 to 453) of $Ar^1$ selected from general formulae (1) to (44) may be hydro groups. At least one or two of $R^m$s (wherein m is an integer in the range of 456 to 732) of a monovalent group selected from general formulae (45) to (69) are each a group selected from a trifluoromethyl group, a cyano group, and a halogen group (halo group).

An aromatic amine compound according to an embodiment of the present invention is preferably a tertiary amine compound (a) or (b) described below.

(a) A tertiary amine compound represented by formula [Ia] above in which, in general formula [I] above, $X^1$ is a phenyl group (—$C_6H_5$), $X^2$ is a 2-naphthyl group (—$C_{10}H_7$), $Ar^1$ is a 2,6-naphthylene group (—$C_{10}H_6$—), and $Ar^2$ is a 3-phenanthryl group having cyano groups (—CN) at the 9-position and the 10-position and a methyl group (—$CH_3$) at the 6-position.

This tertiary amine compound is an aromatic tertiary amine compound in which an unsubstituted phenyl group, an unsubstituted 2-naphthyl group, and a 2,6-naphthylene group are bonded to an amine nitrogen (N). This 3-phenanthryl group is a group (—$C_{14}H_6CH_3(CN)_2$) having substituents of cyano groups (—CN) at the 9-position and the 10-position and a methyl group at the 6-position.

(b) A tertiary amine compound represented by formula [Ib] above in which, in general formula [I] above, $X^1$ is a phenyl group, $X^2$ is a 1-naphthyl group, $Ar^1$ is a 2,6-naphthylene group, and $Ar^2$ is a 2-anthryl group having cyano groups at the 9-position and the 10-position.

This tertiary amine compound is an aromatic tertiary amine compound in which an unsubstituted phenyl group, an unsubstituted 1-naphthyl group, and a 2,6-naphthylene group are bonded to an amine nitrogen (N). This 2-anthryl group is a group (—$C_{14}H_7(CN)_2$) having substituents of cyano groups (—CN) at the 9-position and the 10-position.

When both $X^1$ and $X^2$ are hydro groups, the aromatic amine compound according to an embodiment of the present invention is a primary amine compound. When one of $X^1$ and $X^2$ is a hydro group and the other is an aryl group, the aromatic amine compound is a secondary amine compound. When both $X^1$ and $X^2$ are aryl groups, the aromatic amine compound is a tertiary amine compound.

The aromatic amine compounds according to an embodiment of the present invention can be suitably used for preparing an organic electroluminescent element having good characteristics. An organic electroluminescent element can be constituted by incorporating a plurality types of aromatic amine compound having the structure represented by general formula [I] in an organic layer having a light-emitting region.

Examples of materials that can be used for forming a layer containing a compound according to an embodiment of the present invention include, in addition to compounds according to an embodiment of the present invention, hole transport material (e.g., aromatic amines), electron transport material (e.g., $Alq_3$ and pyrazolines), a series of compounds that are generally used as a dopant for red-light emission (e.g., DCM and analogues thereof, porphyrins, phthalocyanines, perylene compounds, Nile Red, and squarylium compounds), and electrically conductive polymers (e.g., polyfluorene, polyvinyl carbazole, and polyphenylenevinylene).

[Anthracene Derivative Compound (Host Compound) Used Together with Aromatic Amine Compound]

An organic electroluminescent element according to an embodiment of the present invention includes an anode, a cathode, and an organic layer disposed between the anode and the cathode, in which at least one layer constituting the organic layer is a mixed layer containing at least one aromatic amine compound represented by general formula [I] and at least one anthracene derivative compound.

In this organic electroluminescent element, the organic layer has a structure in which a hole-transporting layer, a light-emitting layer, and an electron-transporting layer are stacked; the light-emitting layer is composed of the mixed layer; the light-emitting layer is composed of a host material and a dopant material; and the aromatic amine compound represented by general formula [I] is contained as the dopant material.

Specifically, the light-emitting layer is composed of a mixed layer containing the aromatic amine compound represented by general formula [I] and an anthracene derivative compound. The compounds represented by formula [IIa] to formula [IIe] can be used as the anthracene derivative compound. When the light-emitting layer is composed of such a mixed layer containing a host material and a dopant material, the emission intensity (fluorescence intensity) can be markedly increased and heat resistance can be improved as compared with the case where the light-emitting layer is composed of only an aromatic amine compound.

Formula [IIa]:

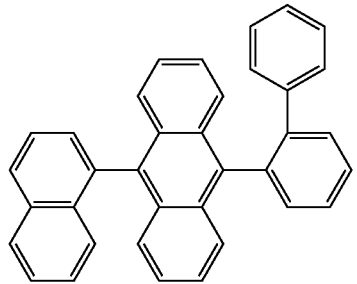

The compound represented by formula [IIa] is an aromatic compound composed of an anthracene derivative. The compound represented by formula [IIa] is anthracene having a 1-naphthyl group (—$C_{10}H_7$) at the 9-position and an o-biphenyl group (—$C_6H_4C_6H_5$) at the 10-position, that is, a compound in which a hydrogen atom at the 10-position of 9-(biphenyl-2-yl)anthracene ($C_{26}H_{18}$) is substituted with a 1-naphthyl group (—$C_{10}H_7$).

Formula [IIb]:

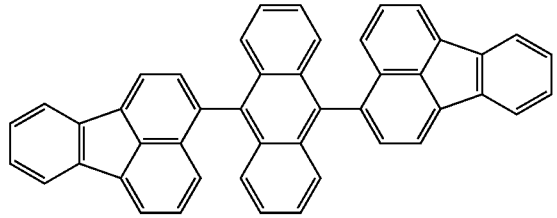

The compound represented by formula [IIb] is an aromatic compound in which fluoranthene ($C_{16}H_{10}$) is bonded to anthracene ($C_{14}H_{10}$) and has a structure in which a fluoranthenyl (—$C_{16}H_9$) group is bonded to each of the 9-position and the 10-position of anthracene.

Formula [IIc]:

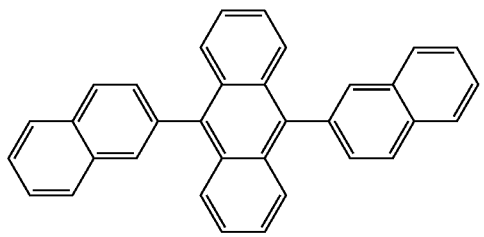

The compound represented by formula [IIc] is an aromatic compound in which naphthalene is bonded to anthracene and has a structure in which a 2-naphthyl group (—$C_{10}H_7$) is bonded to each of the 9-position and the 10-position of anthracene.

Formula [IId]:

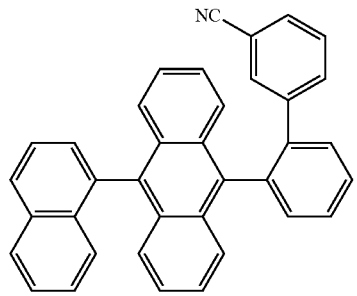

The compound represented by formula [IId] has a structure in which a 1-naphthyl group (—$C_{10}H_7$) and a first phenyl group (—$C_6H_5$) are bonded to the 9-position and the 10-position of anthracene, and the first phenyl group has a second phenyl group (—$C_6H_4(CN)$) having a cyano group (—CN) as a substituent.

Formula [IIe]:

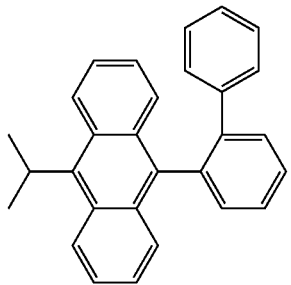

The compound represented by formula [IIe] has a structure in which an isopropyl group (—$C_3H_6$) and a first phenyl group (—$C_6H_5$) are bonded to the 9-position and the 10-position of anthracene, and the first phenyl group has a second phenyl group (—$C_6H_5$) as a substituent.

According to the aromatic amine compound according to an embodiment, —$X^1$, —$X^2$, and —$Ar^1$— are bonded to an amine nitrogen (N), and the group represented by general formula [a] above is bonded to —$Ar^1$—. $X^1$ and $X^2$ each represent a group selected from a hydro group, an alkyl group, an aryl group, an allyl group, an alkoxy group, and an aryloxy group, and $X^1$ and $X^2$ may be the same or different. $Ar^1$ and $Ar^2$ each represent an arylene group, and Y represents a substituent of $Ar_2$. At least one of substituents Y is a substituent selected from a trifluoromethyl group, a cyano group, and a halogen group, and other substituents Y are groups each selected from a hydro group, an alkyl group, an aryl group, an allyl group, an alkoxy group, and an aryloxy group.

The aromatic amine compound according to an embodiment can be suitably used as a material constituting an electron-transporting layer, a hole-transporting layer, or a light-emitting layer of an organic electroluminescent element, and stably emits red light with a high luminance at an optimum wavelength.

An organic electroluminescent element including the aromatic amine compound according to an embodiment can be suitably used in a display device, a lighting device, and the like.

Embodiments will now be described in detail with reference to the drawings.

First, examples of organic electroluminescent elements according to embodiments will be described.

Embodiments

[Example of Transmission-Type Organic Electroluminescent Element]

FIG. 1 is a schematic cross-sectional view of a relevant part illustrating an example of a transmission-type organic electroluminescent element 40A according to an embodiment.

In a bottom-emission organic electroluminescent element shown in FIG. 1, a transparent anode 2, an organic layer (light-emitting layer) 5, and a cathode 3 are sequentially stacked on a substrate 1, and these stacked layers are protected by a protective film 4. A voltage is applied between the transparent anode 2 and the cathode 3, and thus light 30 is emitted from the organic layer 5. This light 30 includes light reflected at the cathode 3 due to the transmission-type structure in which light is transmitted through the anode 2. The light 30 is transmitted through the transparent anode 2, emitted to the outside, and observed from the transparent substrate 1 side.

[Example of Reflection-Type Organic Electroluminescent Element]

Figure 2:
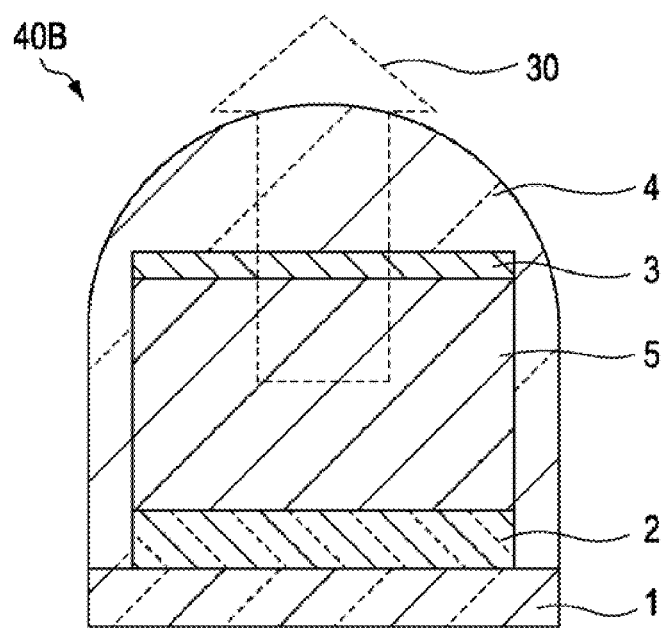
FIG. 2 is a schematic cross-sectional view of a relevant part illustrating an example of a reflection-type organic electroluminescent element according to an embodiment.

FIG. 2 is a schematic cross-sectional view of a relevant part illustrating an example of a reflection-type organic electroluminescent element 40B according to an embodiment.

In a top-emission organic electroluminescent element shown in FIG. 2, an anode 2, an organic layer (light-emitting layer) 5, and a thin cathode 3 are sequentially stacked on a substrate 1, and these stacked layers are protected by a protective film 4. A voltage is applied between the anode 2 and the cathode 3, and thus light 30 is emitted from the organic layer 5. This light 30 includes light reflected at the anode 2 due to the reflection-type structure in which light is reflected at the anode 2. The light 30 is transmitted through the thin cathode 3, emitted to the outside, and observed from the cathode 3 side.

In FIGS. 1 and 2, glass, a plastic, or another suitable material can be used as the substrate 1. When the organic electroluminescent element is used in combination with another light-emitting element, the organic electroluminescent element and the other light-emitting element can share a substrate.

As the anode 2, for example, indium tin oxide (ITO) or $SnO_2$ can be used. As the electrode material constituting the cathode 3, an alloy of an active metal such as Li, Mg, or Ca and a metal such as Ag, Al, or In or a stacked structure including a film composed of such an active metal and a film composed of such a metal can be used.

In addition, by controlling the thickness of the cathode 3, a light reflectivity suitable for the application can be obtained in the transmission-type organic electroluminescent element 40A, and a light transmittance suitable for the application can be obtained in the reflection-type organic electroluminescent element 40B. As the protective film 4 that covers and seals the whole organic electroluminescent element to protect the organic electroluminescent element, various types of material can be used as long as the material is transparent, has moisture resistance, low water permeability, and ultraviolet resistance, and can maintain air-tightness.

The organic layer (light-emitting layer) 5 contains the above-described aromatic amine compound as a luminescent material. As for the light-emitting layer, various configurations in the related art can be used as a layer structure for obtaining the light 30 emitted by the organic electroluminescence. As described below, for example, when a material constituting either a hole-transporting layer and an electron-transporting layer has a light-emitting property, a structure in which these thin layers are stacked can be used as the light-emitting layer.

Furthermore, in order to increase a charge transfer performance, at least one of the hole-transporting layer and the electron-transporting layer may have a structure in which thin films composed of a plurality of materials are stacked or may include thin films composed of a composition in which a plurality of materials are mixed.

In order to increase the light-emitting performance, a thin film composed of at least one fluorescent material may be provided between a hole-transporting layer and an electron-transporting layer. Alternatively, at least one fluorescent material may be incorporated in at least one of the hole-transporting layer and the electron-transporting layer. In such a case, in order to improve the luminous efficiency, a thin film for controlling transport of holes or electrons may be included in the layer structure.

The aromatic amine compound represented by general formula [I] above has both an electron-transporting performance and a hole-transporting performance. Accordingly, the aromatic amine compound can be used as a mixed light-emitting layer with an electron transport material or a mixed light-emitting layer with a hole transport material in the element structure. Alternatively, a mixed layer containing this aromatic amine compound may be provided between an electron-transporting layer and a hole-transporting layer, and the resulting stacked structure may be used as a luminescent material.

The organic layer 5 can be formed by a method such as vacuum evaporation, spin coating, ink jetting, screen printing, flexographic printing, offset printing, gravure printing, laser transfer, thermal transfer, or electrospray deposition.

In the organic electroluminescent element according to an embodiment of the present invention, the organic layer may have an organic stacked structure in which a hole-transporting layer and an electron-transporting layer are stacked (i.e., single heterostructure), and a mixed layer containing the above-described aromatic amine compound may be used as a material for forming the hole-transporting layer or an electron-transporting layer.

Alternatively, the organic layer may have an organic stacked structure in which a hole-transporting layer, a light-emitting layer, and an electron-transporting layer are sequentially stacked (i.e., double heterostructure), and a mixed layer containing the above-described aromatic amine compound may be used as a material for forming the light-emitting layer. Next, examples of organic electroluminescent elements having such organic stacked structures will be described.

[Example of Single Hetero-Type Organic Electroluminescent Element]

Figure 3:
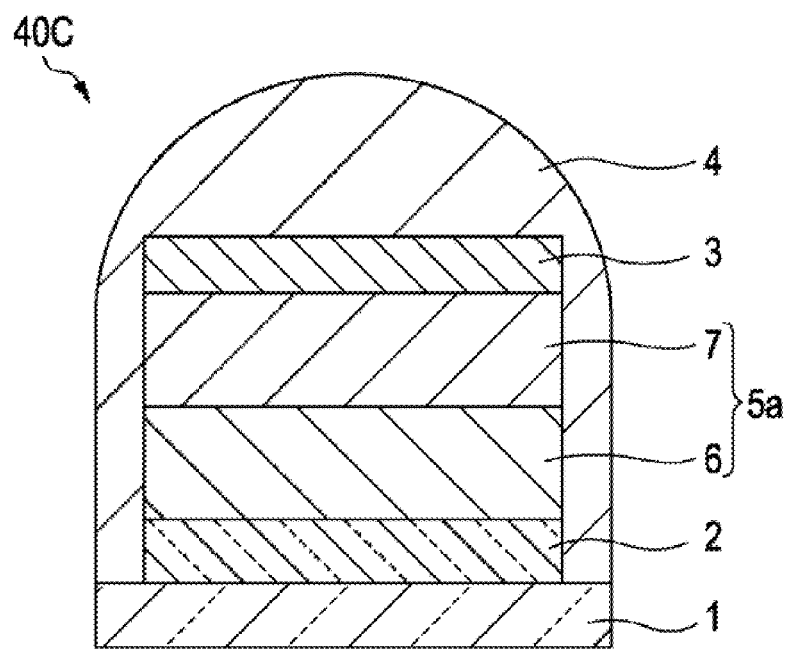
FIG. 3 is a schematic cross-sectional view of a relevant part illustrating an example of a single hetero-type organic electroluminescent element according to an embodiment.

FIG. 3 is a schematic cross-sectional view of a relevant part illustrating an example of a single hetero-type organic electroluminescent element 40C according to an embodiment.

In a bottom-emission organic electroluminescent element shown in FIG. 3, an anode 2, an organic layer 5a including a hole-transporting layer 6 and an electron-transporting layer 7, and a cathode 3 are sequentially stacked on a substrate 1, and these stacked layers are protected by a protective film 4. A voltage is applied between the anode 2 and the cathode 3, and thus light 30 is emitted from the organic layer 5a.

In the element shown in FIG. 3, the element having a layer structure in which a light-emitting layer is omitted, the light 30 having a predetermined wavelength and generated from an interface between the hole-transporting layer 6 and the electron-transporting layer 7 is emitted to the outside by means of a transmission-type structure in which the light 30 is transmitted through the anode 2 or a reflection-type structure in which the light 30 is reflected at the anode 2. In the transmission-type structure, the light 30 includes light reflected at the cathode 3, is transmitted through the transparent anode 2 and emitted, and is observed from the transparent substrate 1 side. In the reflection-type structure, the light 30 includes light reflected at the anode 2, is transmitted through the thin cathode 3 and emitted, and is observed from the cathode 3 side.

[Example of Double Hetero-Type Organic Electroluminescent Element]

Figure 4:
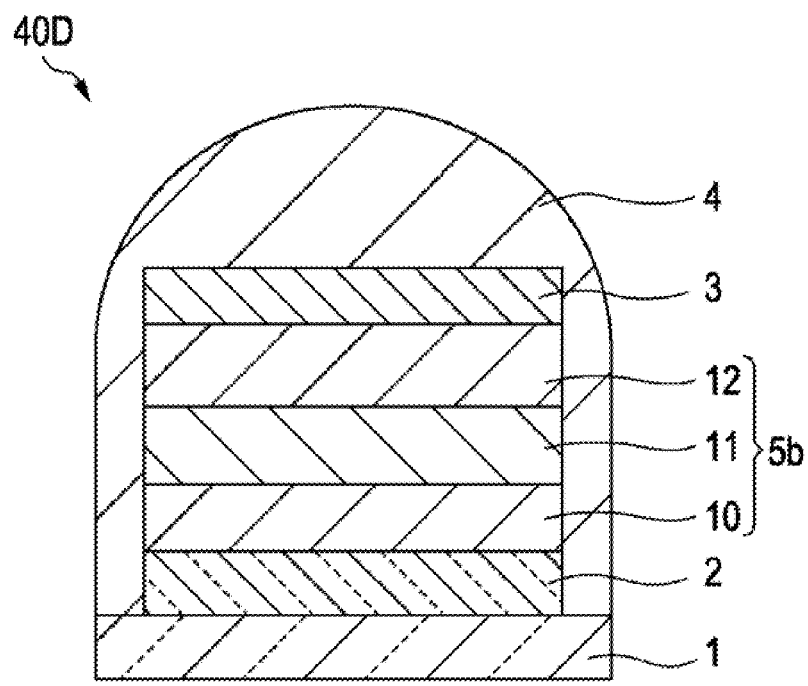
FIG. 4 is a schematic cross-sectional view of a relevant part illustrating an example of a double hetero-type organic electroluminescent element according to an embodiment.

FIG. 4 is a schematic cross-sectional view of a relevant part illustrating an example of a double hetero-type organic electroluminescent element 40D according to an embodiment of the present invention.

A top-emission organic electroluminescent element 40D shown in FIG. 4 is an organic electroluminescent element having a double heterostructure. Specifically, in the organic electroluminescent element 40D, an anode 2, an organic layer 5b including a hole-transporting layer 10, a light-emitting layer 11, and an electron-transporting layer 12, and a cathode 3 are sequentially stacked on a substrate 1, and these stacked layers are protected by a protective film 4. A voltage is applied between the anode 2 and the cathode 3, and thus light 30 is emitted from the organic layer 5b.

In the element having the layer structure shown in FIG. 4, by applying a direct-current voltage between the anode 2 and the cathode 3, holes injected from the anode 2 reach the light-emitting layer 11 through the hole-transporting layer 10, and electrons injected from the cathode 3 reach the light-emitting layer 11 through the electron-transporting layer 12. As a result, recombination of an electron and a hole is generated in the light-emitting layer 11 to produce a singlet exciton, and the light 30 having a predetermined wavelength is emitted from the singlet exciton.

In the element having the layer structure shown in FIG. 4, the light 30 having a predetermined wavelength and generated from the light-emitting layer 11 is emitted to the outside by means of a transmission-type structure in which the light 30 is transmitted through the anode 2 or a reflection-type structure in which the light 30 is reflected at the anode 2. In the transmission-type structure, the light 30 includes light reflected at the cathode 3, is transmitted through the transparent anode 2 and emitted, and is observed from the transparent substrate 1 side. In the reflection-type structure, the light 30 includes light reflected at the anode 2, is transmitted through the thin cathode 3 and emitted, and is observed from the cathode 3 side.

In the organic electroluminescent elements shown in FIGS. 3 and 4, for example, a light-transmissive material such as glass or a plastic can be suitably used as the substrate 1. When the element shown in FIG. 3 or 4 is used in combination with another light-emitting element or when the stacked structures of the element shown in FIG. 3 or 4 are arranged in a matrix, this substrate may be shared. As described above, each of the elements shown in FIGS. 3 and 4 can have either a transmission-type structure or a reflection-type structure.

As the anode 2, for example, ITO or $SnO_2$ can be used. In order to improve the charge injection efficiency, a thin film composed of an organic substance or an organometallic compound may be provided between the anode 2 and the hole-transporting layer 6 (or the hole-transporting layer 10). When the protective film 4 is composed of an electrically conductive material such as a metal, an insulating film may be provided on the side faces of the anode 2.

As the material constituting the cathode 3, an alloy of an active metal such as Li, Mg, Ca, or Cs and a metal such as Ag, Al, or In can be used. Alternatively, the cathode 3 may have a structure in which a layer composed such an active metal and a layer composed of such a metal are stacked. By appropriately selecting the thickness or material of the cathode, an organic electroluminescent element which has a transmission-type structure or a reflection-type structure and which is suitable for the application can be produced.

The protective film 4 functions as a sealing film. By covering the whole organic electroluminescent element with the protective film 4, the charge injection efficiency and the luminous efficiency can be improved. It is sufficient that air-tightness of the protective film 4 can be maintained. The material of the protective film 4 can be appropriately selected from metal elements such as aluminum, gold, and chromium, alloys thereof, organic resins, inorganic resins etc.

The organic layer 5a in the single hetero-structured organic electroluminescent element 40C shown in FIG. 3 is an organic layer in which the hole-transporting layer 6 and the electron-transporting layer 7 are stacked. At least one of the hole-transporting layer 6 and the electron-transporting layer 7 includes a mixed layer containing the above-described aromatic amine compound, and thus a luminous hole-transporting layer 6 or a luminous electron-transporting layer 7 may be formed.

In the organic electroluminescent element 40C, a light-emitting layer may be the electron-transporting light-emitting layer 7. However, light may be emitted from the hole-transporting layer 6 or the interface thereof depending on the voltage applied from a power supply.

The organic layer 5b in the double hetero-structured organic electroluminescent element 40D shown in FIG. 4 is an organic layer in which the hole-transporting layer 10, the light-emitting layer 11 including a mixed layer containing the above-described aromatic amine compound, and the electron-transporting layer 12 are stacked. Alternatively, the organic layer 5b may have other various stacked structures. For example, either the hole-transporting layer 10 or the electron-transporting layer 12 or both the hole-transporting layer 10 and the electron-transporting layer 12 may emit light.

In order to improve a hole transport performance, a hole-transporting layer in which a plurality of hole transport materials are stacked may be formed as the hole-transporting layer 10.

In the organic electroluminescent element 40D, a light-emitting layer is not limited to the light-emitting layer 11. Alternatively, the electron-transporting layer 12 or the hole-transporting layer 10 may function as a light-emitting layer. In order to improve the light-emitting performance, a light-emitting layer 11 containing at least one fluorescent material is preferably provided between the hole-transporting layer 10 and the electron-transporting layer 12. Alternatively, this fluorescent material may be incorporated in either the hole-transporting layer 10 or the electron-transporting layer 12, or both the hole-transporting layer 10 and the electron-transporting layer 12. In such a case, in order to improve the luminous efficiency, the layer structure may include a thin film (such as a hole-blocking layer or an exciton-generating layer) for controlling transport of holes or electrons.

A current applied to each of the organic electroluminescent elements 40A, 40B, 40C, and 40D described above is generally a direct current. Alternatively, a pulse current or an alternating current may be used. The values of current and voltage are not particularly limited as long as the element is not broken within the ranges of the values. However, considering the power consumption and the lifetime of the organic electroluminescent element, it is desirable to efficiently emit light with as low electrical energy as possible.

Next, an example of a display device including organic electroluminescent elements according to an embodiment will now be described.

[Example of Full-Color Flat Display Including Organic Electroluminescent Elements]

Figure 5:
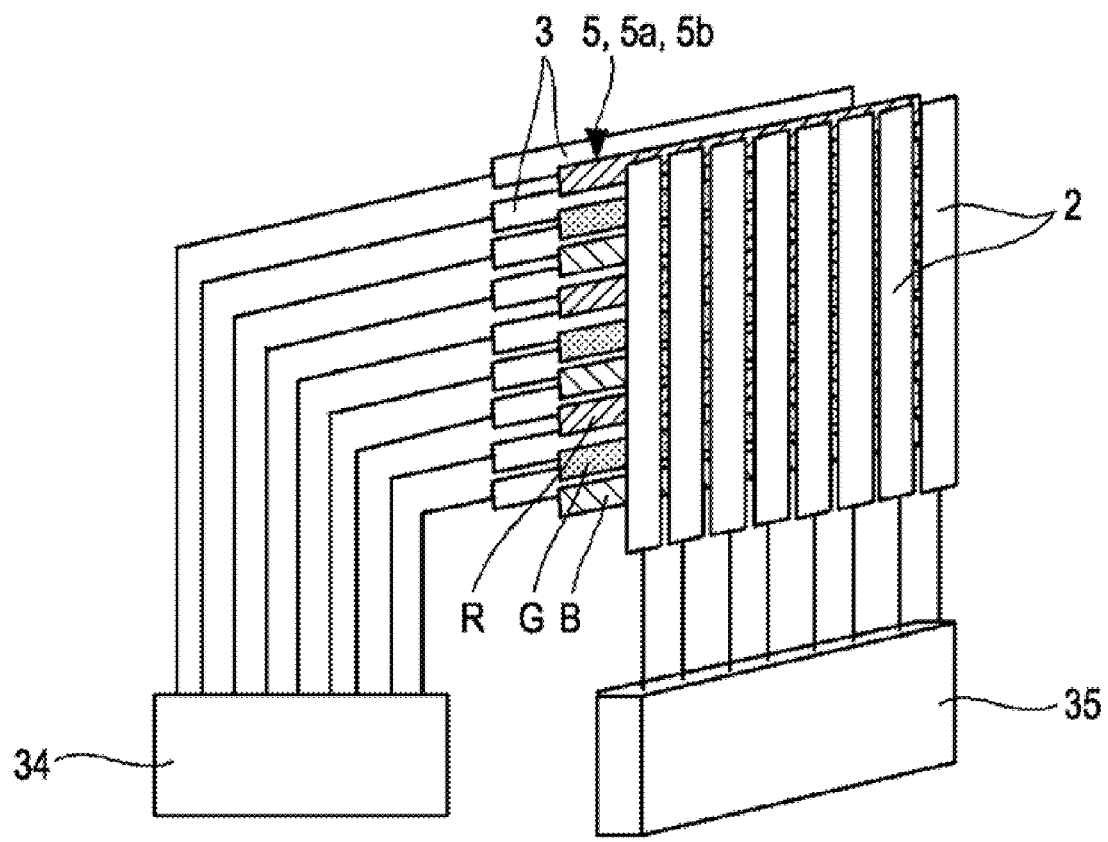
FIG. 5 is a view illustrating an example of a flat display including organic electroluminescent elements according to an embodiment.

FIG. 5 is a view illustrating an example of a full-color flat display including organic electroluminescent elements according to an embodiment of the present invention.

As shown in FIG. 5, an organic layer 5 (5a or 5b) that can emit light of three primary colors, namely, red (R), green (G), and blue (B) is disposed between cathodes 3 and anodes 2. The cathodes 3 and the anodes 2 may be provided in the form of stripes intersecting with each other. The cathodes 3 and the anodes 2 are selected by a luminance signal circuit 34 and a control circuit 35 provided in a shift register, and a signal voltage is applied to each of the cathodes 3 and the anodes 2. Accordingly, the organic layer 5 disposed at a position (pixel) at which a cathode 3 and an anode 2, which are selected by a passive matrix system or an active matrix system, intersect with each other emits light.

The example shown in FIG. 5 shows an 8×3 RGB passive matrix. An organic layer 5a including a hole-transporting layer 6 and an electron-transporting layer 7 or an organic layer 5b including a hole-transporting layer 10, a light-emitting layer 11, and an electron-transporting layer 12 is disposed between the cathodes 3 and the anodes 2 (see FIGS. 3 and 4). The cathodes 3 and the anodes 2 are patterned in the form of stripes and orthogonally intersect each other in a matrix. A signal voltage is applied to the cathodes 3 and the anodes 2 in time series by the control circuit 35 provided in the shift register and the luminance signal circuit 34. Consequently, light is emitted at a crossing position of the stripe-shaped patterns of the cathodes 3 and the anodes 2.

The above-described organic electroluminescent element can be used not only as a display for characters and symbols but also as an image reproduction device. In addition, the stripe-shaped patterns of the cathodes 3 and the anodes 2 may be arranged for each of the colors of red (R), green (G), and blue (B), and thus a multicolor or full-color all-solid-state flat panel display can be produced.

Each of the above-described organic electroluminescent elements may be driven by thin-film transistors.

Figure 6:
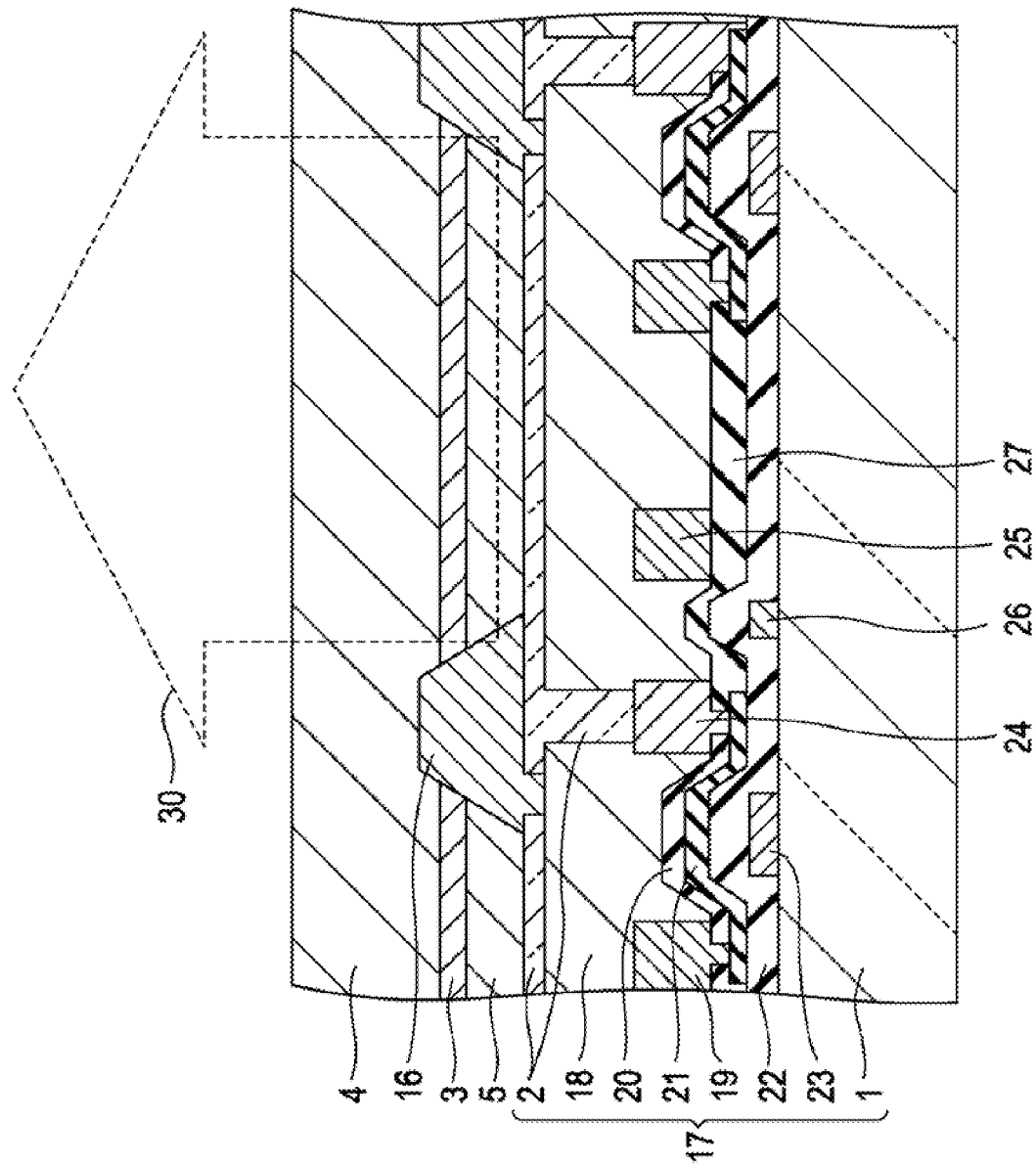
FIG. 6 is a schematic cross-sectional view of a relevant part illustrating an example of a thin-film-transistor-driven top-emission element according to an embodiment.

Next, an example of a thin-film-transistor-driven top-emission element is shown in FIG. 6.

[Example of Thin-Film-Transistor-Driven Top-Emission Element]

FIG. 6 is a schematic cross-sectional view of a relevant part illustrating an example of a top-emission element driven by thin-film transistors, according to an embodiment.

This light-emitting element shown in FIG. 6 is configured as a reflection-type element in which light emitted from an organic layer 5 includes light reflected at an anode 2, is transmitted through a thin cathode 3 and emitted to the outside, and is observed from the cathode 3 side. This light-emitting element is a top emission element in which light is emitted to the top face.

As shown in FIG. 6, a thin-film transistor 17 includes a gate electrode 23, a drain electrode 19, a source electrode 24, a semiconductor layer 21, an interlayer insulating film 22, an interlayer insulating film 20, a wiring 25, a wiring 26, an insulating film 27, a planarizing layer 18 etc. These components are provided on a substrate 1. The organic layer (light-emitting layer) 5 that emits light 30 and the cathode 3 are separated by barriers 16 so that a plurality of organic electroluminescent elements are formed on the anode 2. The organic electroluminescent elements are protected by a protective film 4.

Next, examples of aromatic amine compounds according to embodiments will be described.
[Examples of Aromatic Amine Compounds]
Preferable examples of aromatic amine compounds according to embodiments of the present invention include tertiary amine compounds (71) and (77) shown below.

Compound (71):

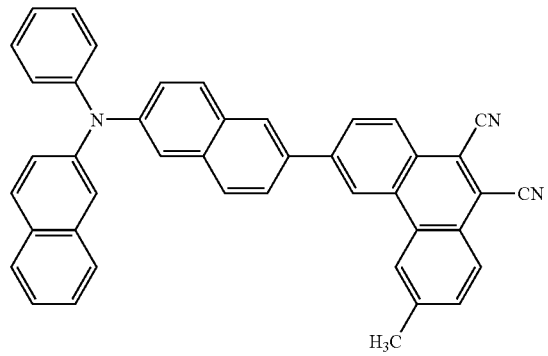

Compound (77):

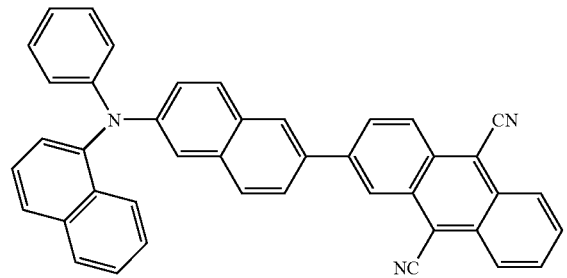

Compound (71) is a tertiary amine compound in which, in general formula [I] above, $X^1$ is a phenyl group (—$C_6H_5$), $X^2$ is a 2-naphthyl group (—$C_{10}H_7$), $Ar^1$ is a 2,6-naphthylene group (—$C_{10}H_6$—) and $Ar^2$ is a 3-phenanthryl group having cyano groups (—CN) at the 9-position and the 10-position, and a methyl group (—$CH_3$) at the 6-position.

This tertiary amine compound is an aromatic tertiary amine compound in which an unsubstituted phenyl group, an unsubstituted 2-naphthyl group, and a 2,6-naphthylene group are bonded to an amine nitrogen (N). The 3-phenanthryl group having substituents of cyano groups (—CN) at the 9-position and the 10-position and a methyl group at the 6-position (—$C_{14}H_6CH_3(CN)_2$) is bonded to the 2,6-naphthylene group.

Compound (77) is a tertiary amine compound in which, in general formula [I] above, $X^1$ is a phenyl group, $X^2$ is a 1-naphthyl group, $Ar^1$ is a 2,6-naphthylene group, and $Ar^2$ is a 2-anthryl group having cyano groups at the 9-position and the 10-position.

This tertiary amine compound is an aromatic tertiary amine compound in which an unsubstituted phenyl group, an unsubstituted 1-naphthyl group, and a 2,6-naphthylene group are bonded to an amine nitrogen (N). A 2-anthryl group having substituents of cyano groups (—CN) at the 9-position and the 10-position (—$C_{14}H_7(CN)_2$) is bonded to the 2,6-naphthylene group.

Figure 7:
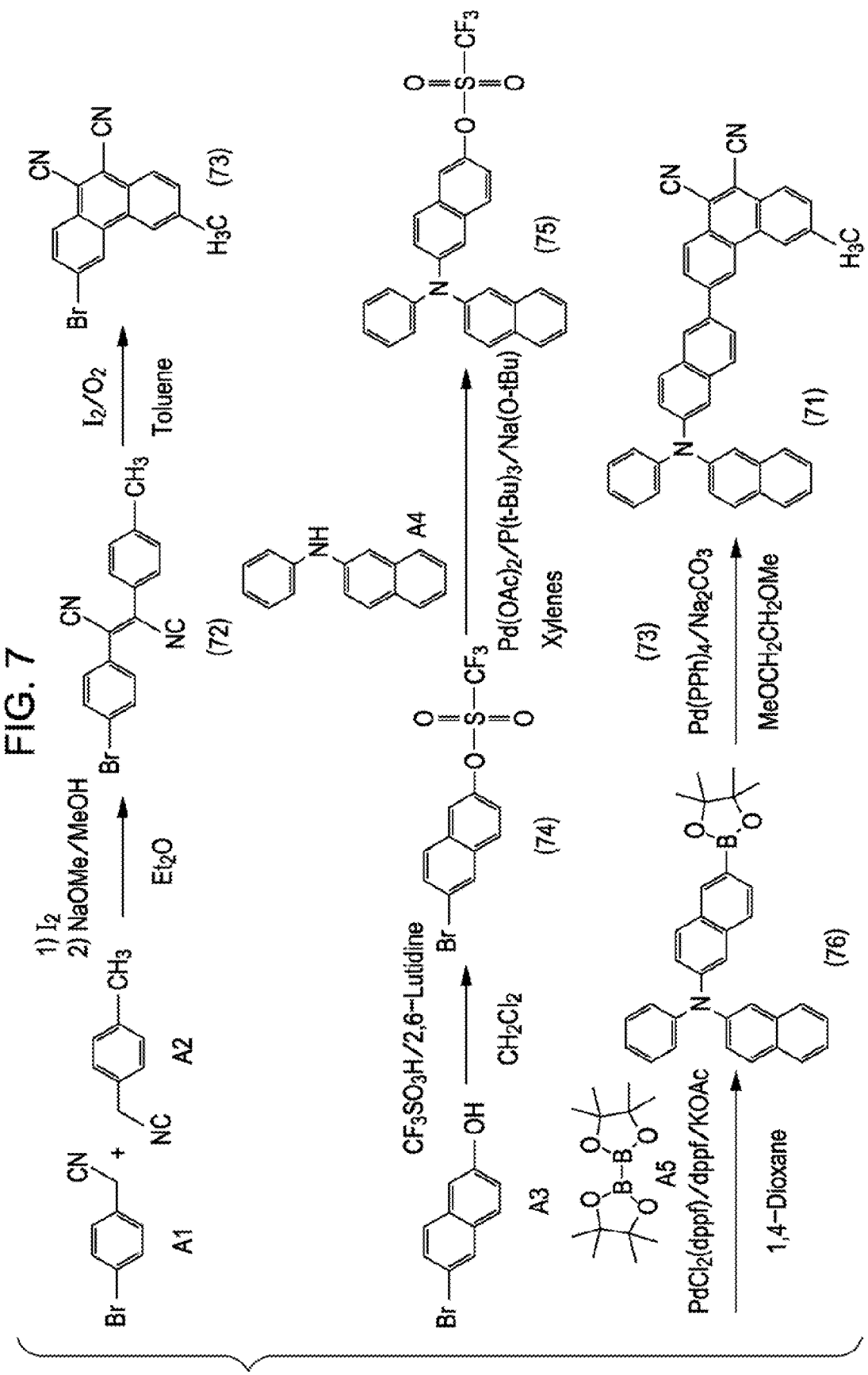
FIG. 7 is a drawing showing an example of a synthesis scheme of compound (71) according to an embodiment.

Next, synthesis examples of the aromatic amine compounds according to embodiments will be described.
[Synthesis Examples of Aromatic Amine Compounds]
Next, examples of synthesis schemes of compound (71) and compound (77) according to embodiments will be described.
[Example of Synthesis Scheme of Aromatic Tertiary Amine Compound (71)]
FIG. 7 shows an example of a synthesis scheme of compound (71) according to an embodiment.

First, compound A1 (4-bromobenzyl cyanide, $C_8H_6BrN$) and compound A2 (p-methylbenzyl cyanide, $C_9H_9N$) are dissolved in anhydrous ethyl ether ($Et_2O$), and iodine ($I_2$) is added to the solution. Next, a methanol (MeOH) solution of sodium methoxide (NaOMe) is added dropwise to the solution, and the resulting mixture is stirred. Thus, a crude product containing compound (72) is obtained.

The crude product containing compound (72) is dissolved in toluene. Iodine ($I_2$) is added to the solution, and the resulting reaction solution is irradiated with ultraviolet light while supplying oxygen ($O_2$). Thus, a crude product containing a by-product and compound (73) is obtained. The crude product is then purified by silica gel chromatography to obtain compound (73).

2,6-Lutidine (2,6-dimethylpyridine, $C_7H_9N$) and trifluoromethanesulfonic acid ($CF_3SO_3H$) are added to a dichloromethane ($CH_2Cl_2$) solution of compound A3 (6-bromo-naphthalen-2-ol) ($C_{10}H_7BrO$) to conduct a reaction. This reaction solution is then purified by silica gel chromatography to obtain compound (74).

Compound (74), compound A4 (N-phenyl-2-naphthylamine, 2-anilinonaphthalene, $C_{16}H_{13}N$), palladium (II) acetate (Pd(OAc)$_2$), tri(tert-butyl)phosphine (P(t-Bu)$_3$, Bu=$C_4H_9$), sodium tert-butoxide (Na(O-tBu)), and xylenes (herein, a mixture containing o-xylene, m-xylene, and p-xylene is referred to as "xylenes") are mixed under an argon (Ar) gas flow to conduct a reaction. The resulting reaction product is then purified by silica gel chromatography to obtain compound (75).

Compound (75), compound A5 (bis(pinacolate)diboron, $C_{12}H_{24}B_2O_4$), (bis(diphenylphosphino)ferrocene)dichloropalladium (PdCl$_2$(dppf), $C_{34}H_{28}FeP_2 \cdot PdCl_2$), bis(diphenylphosphino)ferrocene (dppf, $C_{34}H_{28}FeP_2$), potassium acetate (KOAc), and 1,4-dioxane ($C_4H_8O_2$) are mixed, and the mixture is refluxed under an Ar gas flow to conduct a reaction. The resulting reaction solution is then purified by silica gel chromatography to obtain compound (76). Note that PdCl$_2$(dppf) is a coordination compound of PdCl$_2$ and dppf ($C_{34}H_{28}FeP_2$) having a structure in which two phosphine moieties are disposed on a ferrocene backbone.

Compound (76), the crude product containing compound (73), tetrakis(triphenylphosphine)palladium(0) (Pd(PPh$_3$)$_4$, Pd[P(C$_6$H$_5$)$_3$]$_4$), sodium carbonate (Na$_2$CO$_3$), and 1,2-dimethoxyethane (MeOCH$_2$CH$_2$OMe) are mixed, and the mixture is refluxed under an Ar gas flow to conduct a reaction.

Thus, a crude product containing compound (71) is obtained. The crude product is then purified by silica gel chromatography to obtain compound (71).

[Example of Synthesis Scheme of Aromatic Tertiary Amine Compound (77)]

Figure 8:
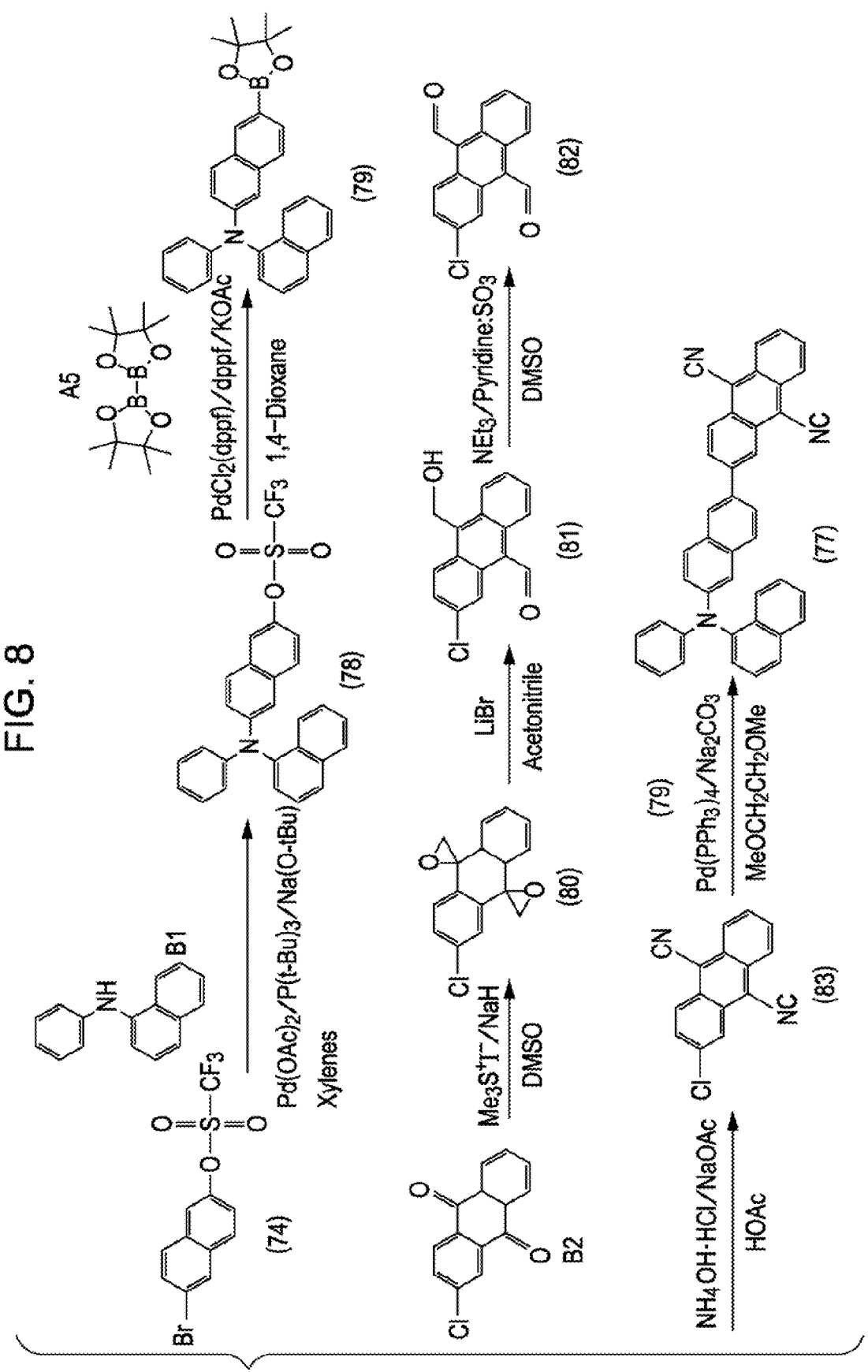
FIG. 8 is a drawing showing an example of a synthesis scheme of compound (77) according to an embodiment.

FIG. 8 shows an example of a synthesis scheme of compound (77) according to an embodiment of the present invention.

Compound (78) and compound (79) can be synthesized as in compound (75) and compound (76), respectively, shown in FIG. 7.

Compound (74) obtained as in the scheme shown in FIG. 7, compound B1 (N-phenyl-1-naphthylamine, 1-anilinonaphthalene, $C_{16}H_{13}N$), palladium (II) acetate (Pd(OAc)$_2$), tri(tert-butyl)phosphine (P(t-Bu)$_3$, Bu=$C_4H_9$), sodium tert-butoxide (Na(O-tBu)), and xylenes are mixed under an Ar gas flow to conduct a reaction. The resulting reaction solution is then purified by silica gel chromatography to obtain compound (78).

Compound (78), compound A5 (bis(pinacolate)diboron, $C_{12}H_{24}B_2O_4$), (bis(diphenylphosphino)ferrocene)dichloropalladium (PdCl$_2$(dppf), $C_{34}H_{28}FeP_2$·PdCl$_2$), bis(diphenylphosphino)ferrocene (dppf, $C_{34}H_{28}FeP_2$), potassium acetate (KOAc), and 1,4-dioxane ($C_4H_8O_2$) are mixed, and the mixture is refluxed under an Ar gas flow to conduct a reaction. The resulting reaction solution is then purified by silica gel chromatography to obtain compound (79).

Sodium hydride (NaH) from which oil has been removed in a darkroom is mixed with dehydrated dimethyl sulfoxide (DMSO, $C_2H_6OS$) and compound B2 (2-chloro-9,10-anthraquinone, $C_{14}H_7Cl_2$). A dehydrated DMSO solution of trimethyliodosulfur (IV) (Me$_3$S$^+$I$^-$, $C_3H_9$S$^+$I$^-$) is added dropwise to the mixed solution in an argon atmosphere at room temperature or lower over a long period of time. The mixed solution is stirred at room temperature and then poured into ice water. The solution is then stirred overnight. Ethyl acetate is then added to the solution to separate the resulting mixture. The organic layer is washed with water and saline solution, and dried over anhydrous magnesium sulfate. The resulting solution is then concentrated under reduced pressure to epoxidize compound B2. Thus, a crude product solution of compound (epoxide) (80) is obtained. Note that $C_3H_9$S$^+$I$^-$ is a salt of trimethylsulfonium ($C_3H_9$S$^+$) and I$^-$.

Compound (80) is added to an acetonitrile ($C_2H_3N$) solution of lithium bromide (LiBr) and potassium iodide (KI) in an argon atmosphere in a darkroom. The mixture is stirred for a long time under heating to conduct a reaction, and a precipitated solid is then separated by filtration. The resulting crude crystals are washed with acetonitrile. Thus, an orange crystalline compound (81) in which epoxy rings of compound (80) are opened is obtained.

A method of obtaining compound (83) from compound (81) by way of compound (82) follows a general organic synthesis method. Specifically, by conducting a triethylamine (NEt$_3$)/pyridine:SO$_3$ oxidation of compound (81), —COH is selectively oxidized to —C=O to obtain aldehyde compound (82). Subsequently, nitrile compound (83) can be obtained from aldehyde compound (82) by way of an oxime using hydroxyammonium hydrochloride (NH$_4$OH·HCl).

More specifically, triethylamine (NEt$_3$, $C_6H_{15}N$) and pyridine-sulfur trioxide complex (sulfur trioxidepyridine salt, pyridine:SO$_3$, $C_5H_5N$·SO$_3$) are added to a dehydrated DMSO solution of compound (81) at 37° C. or lower in an argon atmosphere. The mixture is stirred and then poured into water. The resulting precipitate is filtered, and the precipitate is suspended again in water. The suspension is stirred and then filtered. Next, the resulting product is suspended in methanol, and the suspension is stirred. Subsequently, the suspension is filtered. Thus, orange crystalline compound (82) is obtained.

Hydroxyammonium hydrochloride (NH$_4$OH·HCl) and compound (82) are added to a HOAc (wherein Ac represents CH$_3$CO, and thus HOAc represents acetic acid) solution of sodium acetate (NaOAc). The mixture is refluxed to conduct a reaction. The mixture is cooled and then poured into water. The resulting crystals are filtered. The crude crystals are sequentially washed with water and methanol, and then purified with a silica gel column (eluate: hot toluene). The resulting crudely purified solid is recrystallized a plurality of times with tetrahydrofuran (THF). Thus, bright yellow crystalline compound (83) is obtained.

Compound (79), compound (83), tetrakis(triphenylphosphine)palladium(0) (Pd(PPh$_3$)$_4$, Pd[P(C$_6$H$_5$)$_3$]$_4$), sodium carbonate (Na$_2$CO$_3$), and 1,2-dimethoxyethane (DME, MeOCH$_2$CH$_2$OMe) are mixed, and the resulting reaction solution is refluxed under an Ar gas flow to conduct a reaction. The reaction solution is dried under reduced pressure, and the resulting crude product is purified by silica gel chromatography (eluate: hot toluene) to obtain a red crude product. This crude product is purified by sublimation. Thus, pure compound (77) is obtained.

Next, Examples of the present invention will be described, but the present invention is not limited to the Examples.

EXAMPLES

[First Organic Electroluminescent Element]

First, an organic electroluminescent element including an organic light-emitting layer containing compound (71) and host compound (84) below will be described.

(1) Configuration and Fluorescence Intensity of Organic Light-Emitting Layer Containing Compound (71)

A mixed film (codeposited film, thickness: 25 nm) containing compound (71) and host compound (84) was formed on a glass substrate by a vacuum evaporation method in a vacuum of 10$^{-4}$ Pa or less.

Compound (71):

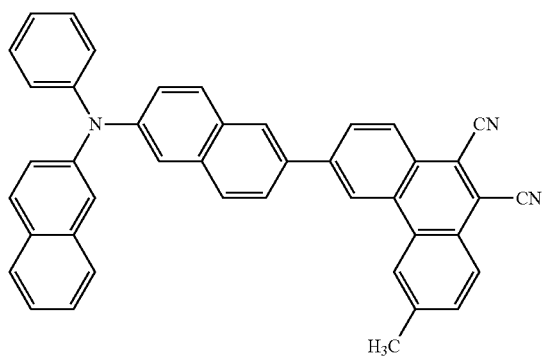

-continued

Compound (84):

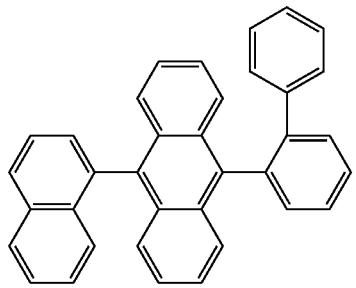

Host compound (84) is an aromatic compound composed of an anthracene derivative. Host compound (84) is 9-(biphenyl-2-yl)-10-(1-naphthyl)anthracene ($C_{36}H_{24}$) having a 1-naphthyl group (—$C_{10}H_7$) at the 9-position and an o-biphenyl group (—$C_6H_4C_6H_5$) at the 10-position. Host compound (84) can be obtained by substituting a hydro group (—H) at the 10-position of 9-(biphenyl-2-yl)anthracene ($C_{26}H_{18}$) with a 1-naphthyl group (—$C_{10}H_7$). Host compound (84) can be synthesized by reacting 9-(1-naphthyl)-10-bromo-anthracene with 2-biphenyl boronic acid. The synthesis method will be described in detail in an Example below.

Figure 9:
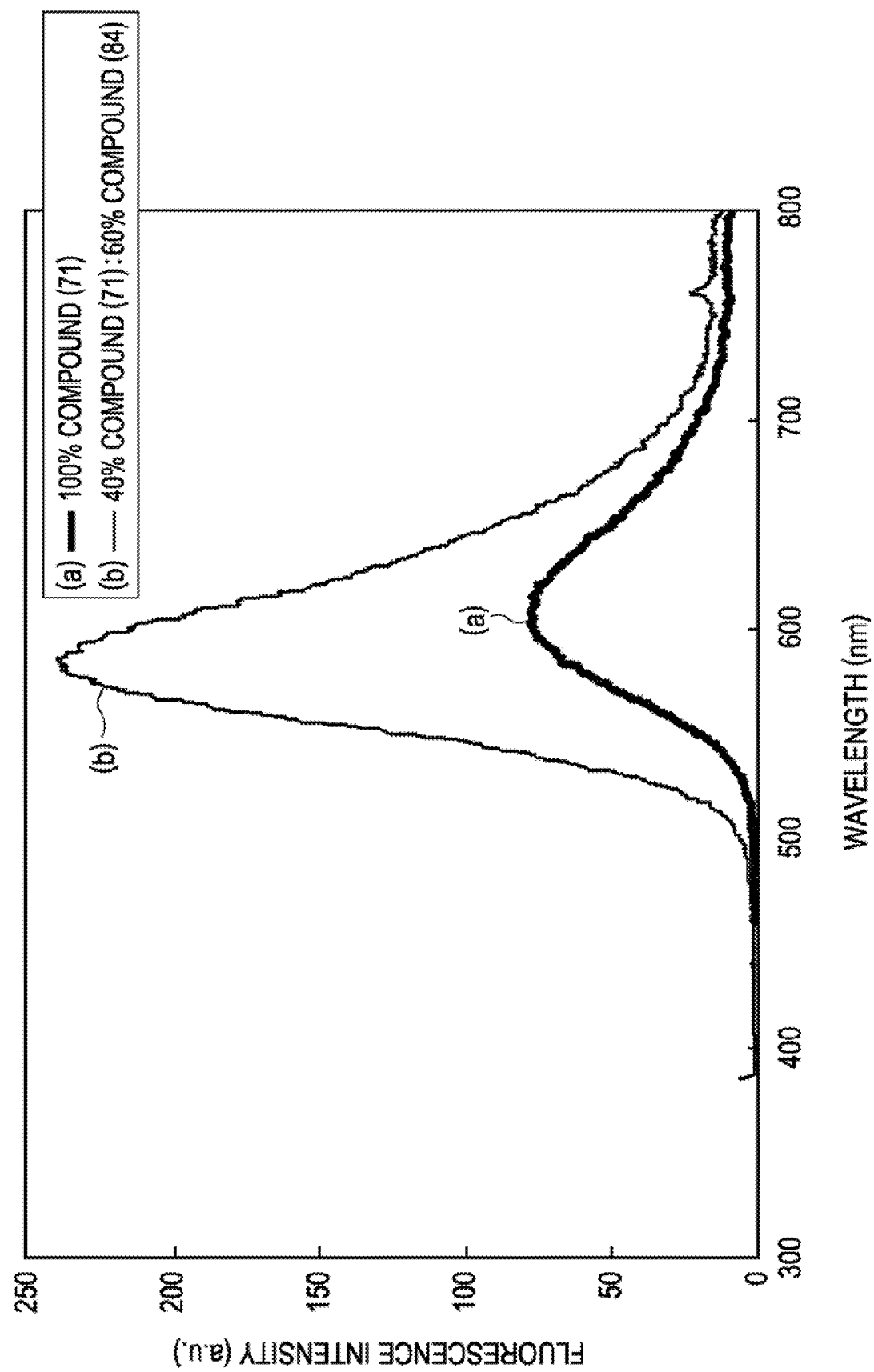
FIG. 9 is a graph showing a relationship between examples of organic light-emitting layers containing compound (71) and fluorescence intensities thereof in an Example.

FIG. 9 is a graph showing a relationship between examples of organic light-emitting layers containing compound (71) and fluorescence intensities thereof in an Example of the present invention.

FIG. 9 shows fluorescence spectra. In FIG. 9, the horizontal axis represents the wavelength (nm) and the vertical axis represents the fluorescence intensity (arbitrary units). In FIG. 9, (a) shows a fluorescence spectrum of a thin film composed of 100% of compound (71), and (b) shows a fluorescence spectrum of a mixed film (codeposited film) composed of 40% of compound (71) and 60% of host compound (84) (wherein the composition of the codeposited film is expressed in units of volume percent (%), and this is the same as that in the description below).

In FIG. 9, (a) is a fluorescence spectrum obtained by excitation at 453 mm, which is an absorption maximum of compound (71), and (b) is a fluorescence spectrum obtained by excitation at 382 nm, which is an absorption maximum of host compound (84). In the codeposited film, fluorescence of host compound (84) was not observed, and red fluorescence was observed from compound (71) as a result of energy transfer.

According to the fluorescence spectrum of the thin film composed of 100% of compound (71), which is shown by (a) in FIG. 9, it was found that the film could be used as a good red-light-emitting material having a fluorescence maximum of 610 nm. On the other hand, in the codeposited film shown by (b) of FIG. 9, the fluorescence intensity was increased by three times as compared with that of (a), which shows the result of the thin film composed of 100% of compound (71). This result suggested that the codeposited film can provide a good red-light-emitting element by combining with an appropriate filter.

(2) Preparation of Organic Electroluminescent Element

A double hetero-structured transmission-type organic electroluminescent element shown in FIG. 4 was prepared. This organic electroluminescent element included a hole-transporting layer 10 (see FIG. 4) including a first hole-transporting layer and a second hole-transporting layer and a light-emitting layer composed of a mixed film (codeposited film) containing compound (71) and host compound (84).

The first hole-transporting layer was composed of 4,4',4"-tris(3-methyl-phenylphenylamino)triphenylamine (tris[4-(3-methylphenylamino)phenyl]amine, m-MTDATA, $C_{57}H_{48}N_4$). The second hole-transporting layer was composed of 4,4'-bis[N,N'-di(1-naphthyl)-N,N'-diphenyl]biphenyldiamine (4,4'-bis[phenyl(1-naphthyl)amino]biphenyl, α-NPD, $C_{44}H_{32}N_2$).

m-MTDATA:

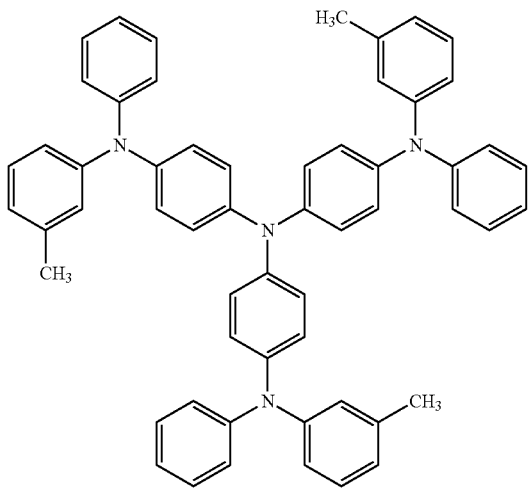

α-NPD:

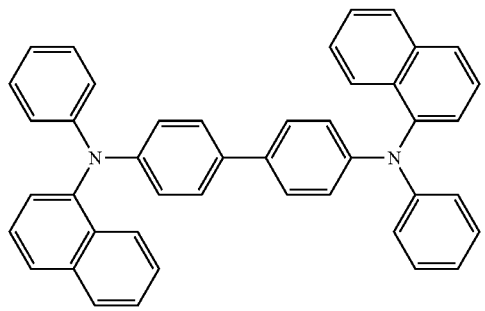

First, a glass substrate (30 mm×30 mm) having an anode composed of ITO with a thickness of 100 nm thereon was placed in a vacuum evaporation system. A metal mask having a plurality of unit openings each having dimensions of 2.0 mm×2.0 mm was disposed as an evaporation mask in proximity to the substrate. Next, m-MTDATA, which was a material constituting the first hole-transporting layer, was deposited by a vacuum evaporation method so as to have a thickness of 110 nm in a vacuum of $10^{-4}$ Pa or less. Subsequently, α-NPD, which was a material constituting the second hole-transporting layer, was deposited so as to have a thickness of 110 nm.

Furthermore, as materials constituting the light-emitting layer, compound (71) and host compound (84) were deposited on the second hole-transporting layer so as to have a thickness of 65 nm. In this step, compound (71) and host compound (84) were deposited so that the ratio of compound (71):host compound (84) was 40%:60%. Furthermore, as an electron-transporting layer, tris(8-quinolinyloxy)aluminum (tris(8-quinolinol) aluminum, $Alq_3$, $C_{27}H_{18}AlN_3O_3$) was deposited on the light-emitting layer so as to have a thickness of 30 nm. The deposition rate in each of these steps was 0.2 nm/sec.

A stacked film of magnesium (Mg) and silver (Ag) was used as a material constituting a cathode. A Mg film having a thickness of 50 nm and a Ag film having a thickness of 150 nm were formed by vacuum evaporation at a deposition rate of 1 nm/sec. Thus, the organic electroluminescent element shown in FIG. 4 was prepared.

(3) Characteristics of Organic Electroluminescent Element

A forward bias direct-current voltage was applied to the organic electroluminescent element prepared as described above in a nitrogen atmosphere to evaluate luminous characteristics. The luminescent color was red. As a result of spectrometry, an emission spectrum similar to that shown in FIG. 9 was obtained. A spectrometer including a photodiode array manufactured by Otsuka Electronics Co., Ltd. as a detector was used in the spectrometry. In addition, a voltage-luminance characteristic and an external quantum efficiency were measured.

Figure 10:
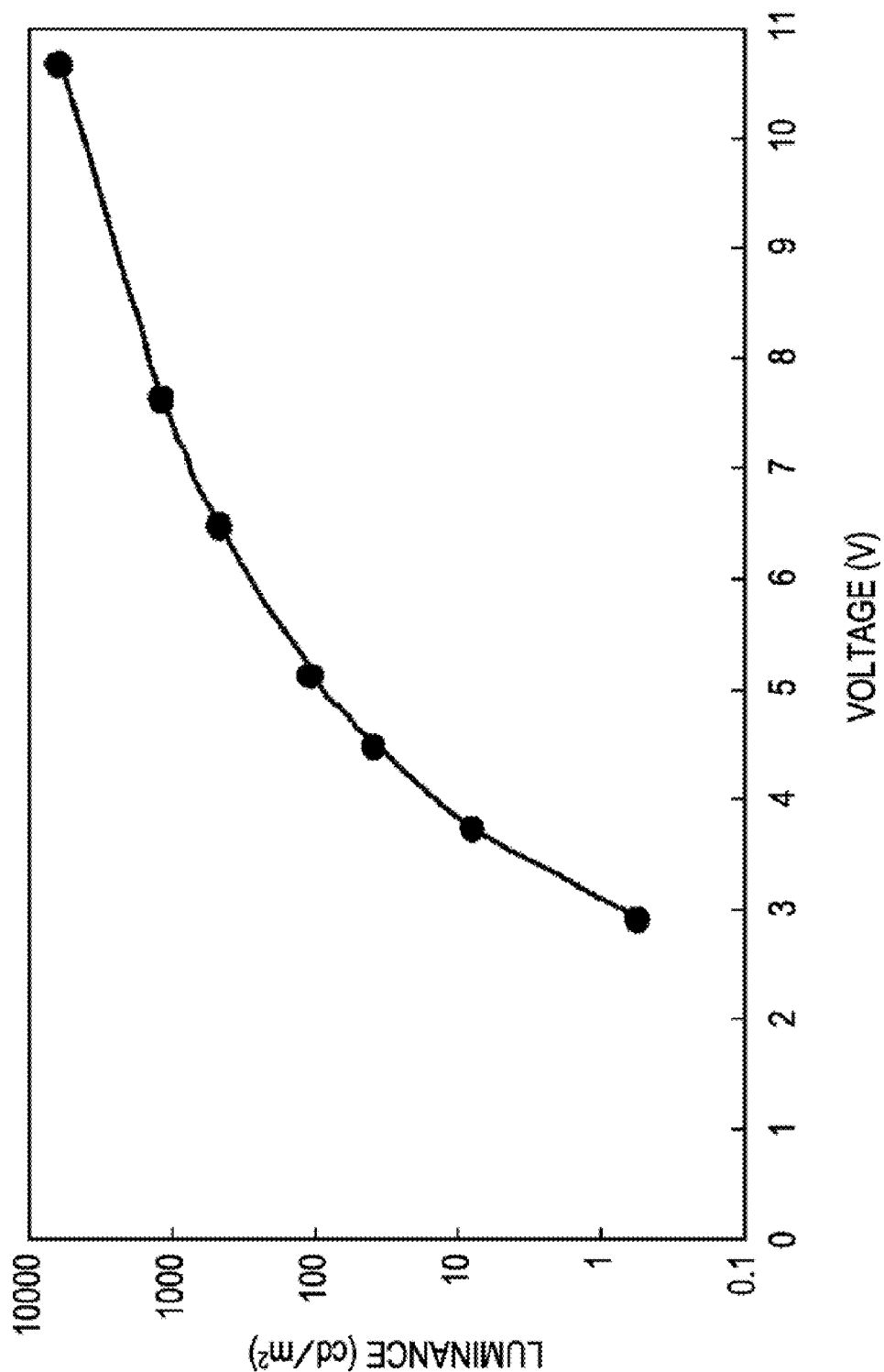
FIG. 10 is a graph showing an example of a voltage-luminance characteristic of an organic electroluminescent element in the Example.

FIG. 10 is a graph showing an example of the voltage-luminance characteristic of the organic electroluminescent element in the Example. In FIG. 10, the horizontal axis represents the applied voltage (V) and the vertical axis represents the luminance (cd/m$^2$).

Figure 11:
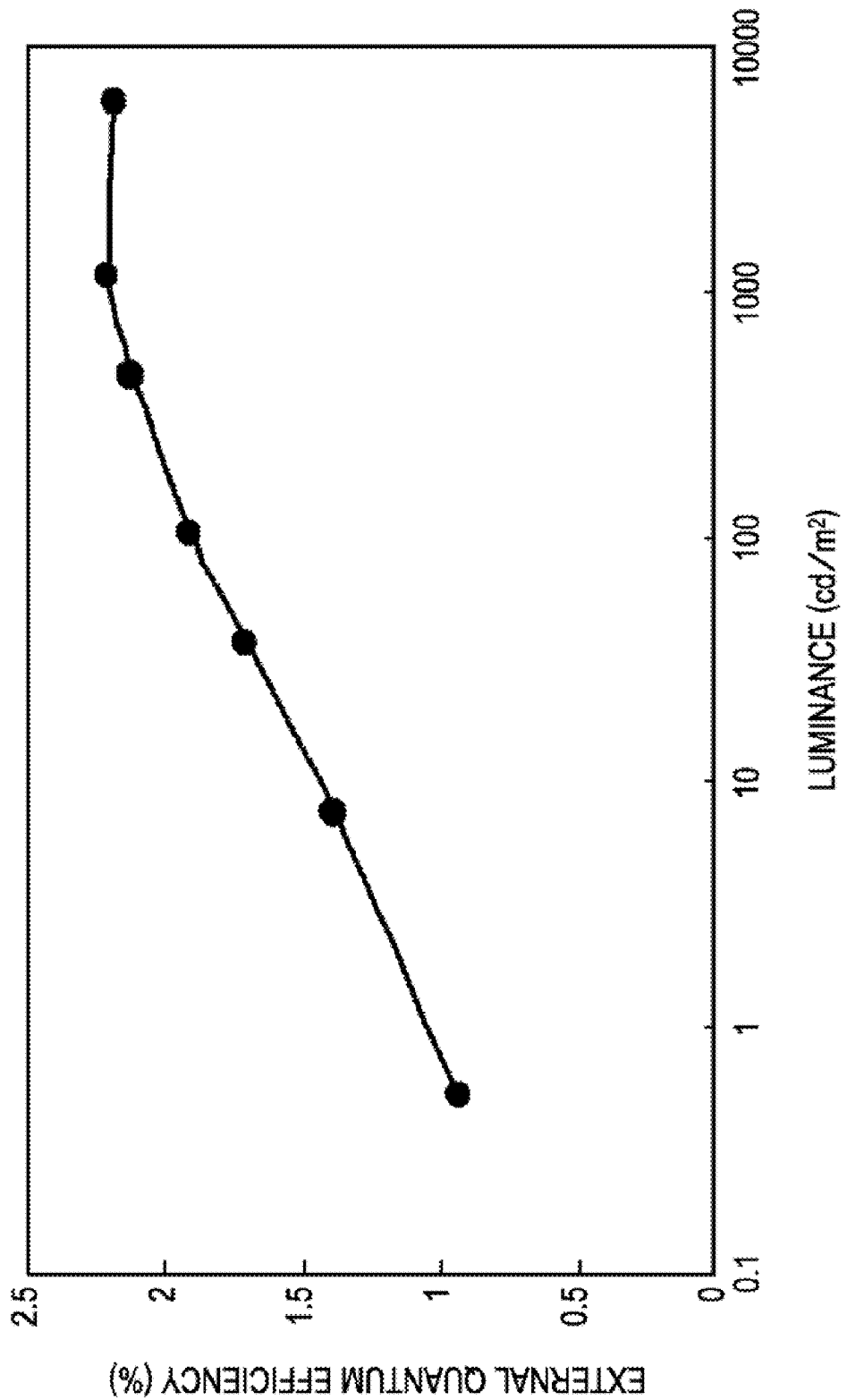
FIG. 11 is a graph showing an example of a luminance-external quantum efficiency characteristic of the organic electroluminescent element in the Example.

FIG. 11 is a graph showing an example of a luminance-external quantum efficiency characteristic of the organic electroluminescent element in the Example. In FIG. 11, the horizontal axis represents the luminance (cd/m$^2$) and the vertical axis represents the external quantum efficiency (%).

Figure 12:
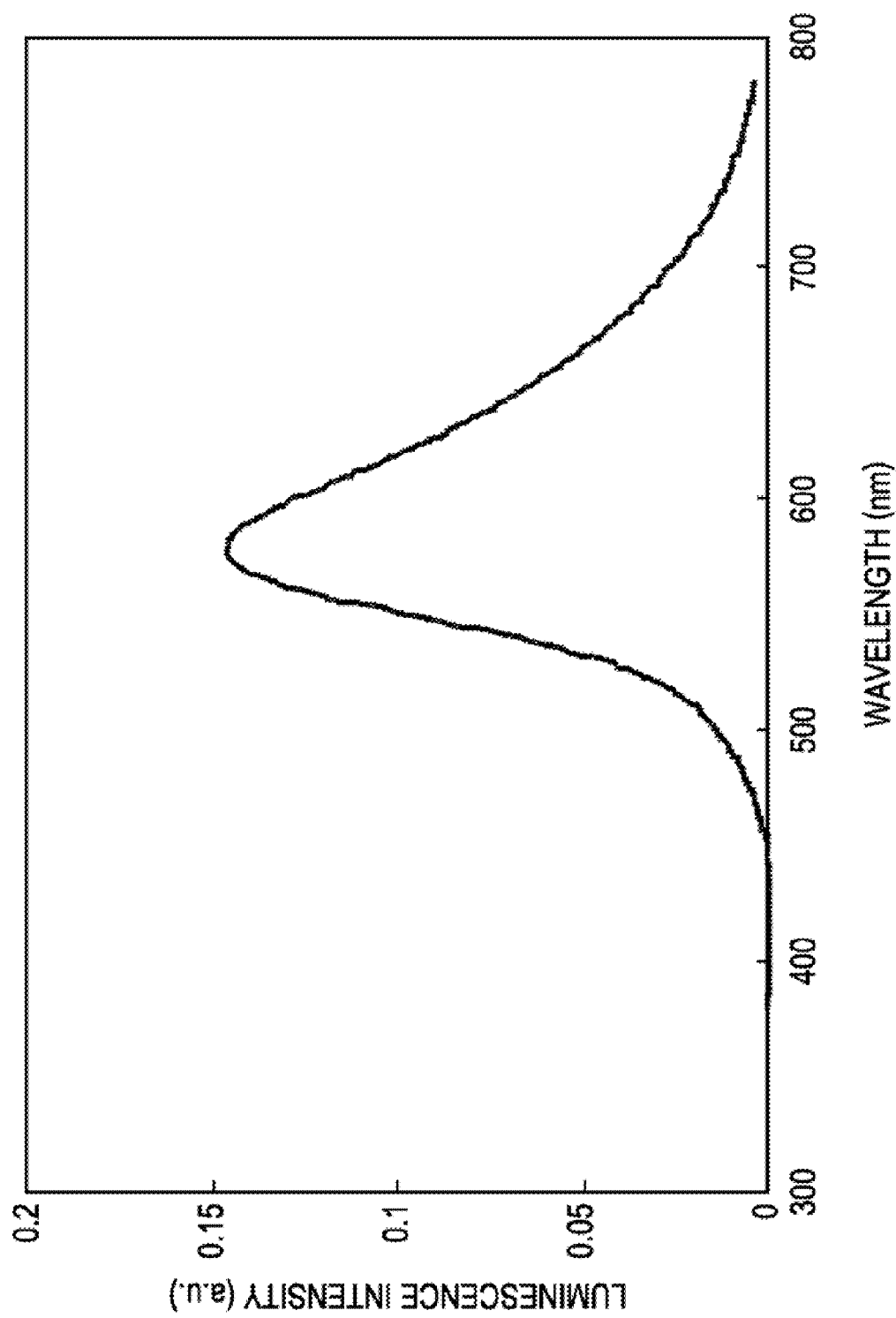
FIG. 12 is a graph showing an example of an emission spectrum of the organic electroluminescent element in the Example.

FIG. 12 is a graph showing an example of an emission spectrum (organic electroluminescence spectrum) of the organic electroluminescent element in the Example. In FIG. 12, the horizontal axis represents the wavelength (nm) and the vertical axis represents the luminescence intensity (arbitrary units).

As shown in FIGS. 10 and 11, in the measurement of the voltage-luminance characteristic, a luminance of 3,000 cd/m$^2$ was obtained at 8 V, and the external quantum efficiency at this luminance was very high; 2.2%. FIG. 12 shows the organic electroluminescence spectrum at that time.

After the preparation of this organic electroluminescent element, the organic electroluminescent element was left to stand in a nitrogen atmosphere for one month. According to the result, degradation of the characteristics of the organic electroluminescent element was not observed. Furthermore, in order to forcibly degrade the organic electroluminescent element, light was continuously emitted from the organic electroluminescent element with an initial luminance of 100 cd/m$^2$ while supplying a constant current. In this test, the time during which the luminance was decreased to the half of the initial value was 2,000 hours.

[Second Organic Electroluminescent Element]

Next, an organic electroluminescent element including an organic light-emitting layer containing compound (77) and host compound (85) below will be described.

(1) Configuration and Fluorescence Intensity of Organic Light-Emitting Layer Containing Compound (77)

A mixed film (codeposited film, thickness: 30 nm) containing compound (77) and host compound (85) was formed on a glass substrate by a vacuum evaporation method in a vacuum of 10$^{-4}$ Pa or less.

Compound (77):

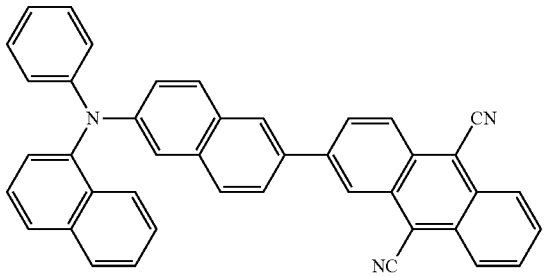

Compound (85): 9,10-Di(3-fluoranthenyl) anthracene

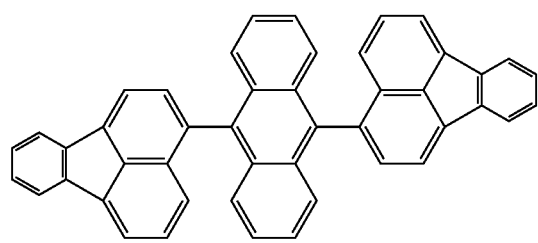

Compound (85) is a compound described in Japanese Unexamined Patent Application Publication Nos. 2001-257074 and 2002-69044. Compound (85) is an aromatic compound in which fluoranthene ($C_{16}H_{10}$) is bonded to anthracene ($C_{14}H_{10}$) and has a structure in which a fluoranthenyl group (—$C_{16}H_9$) is bonded to each of the 9-position and the 10-position of anthracene.

Figure 13:
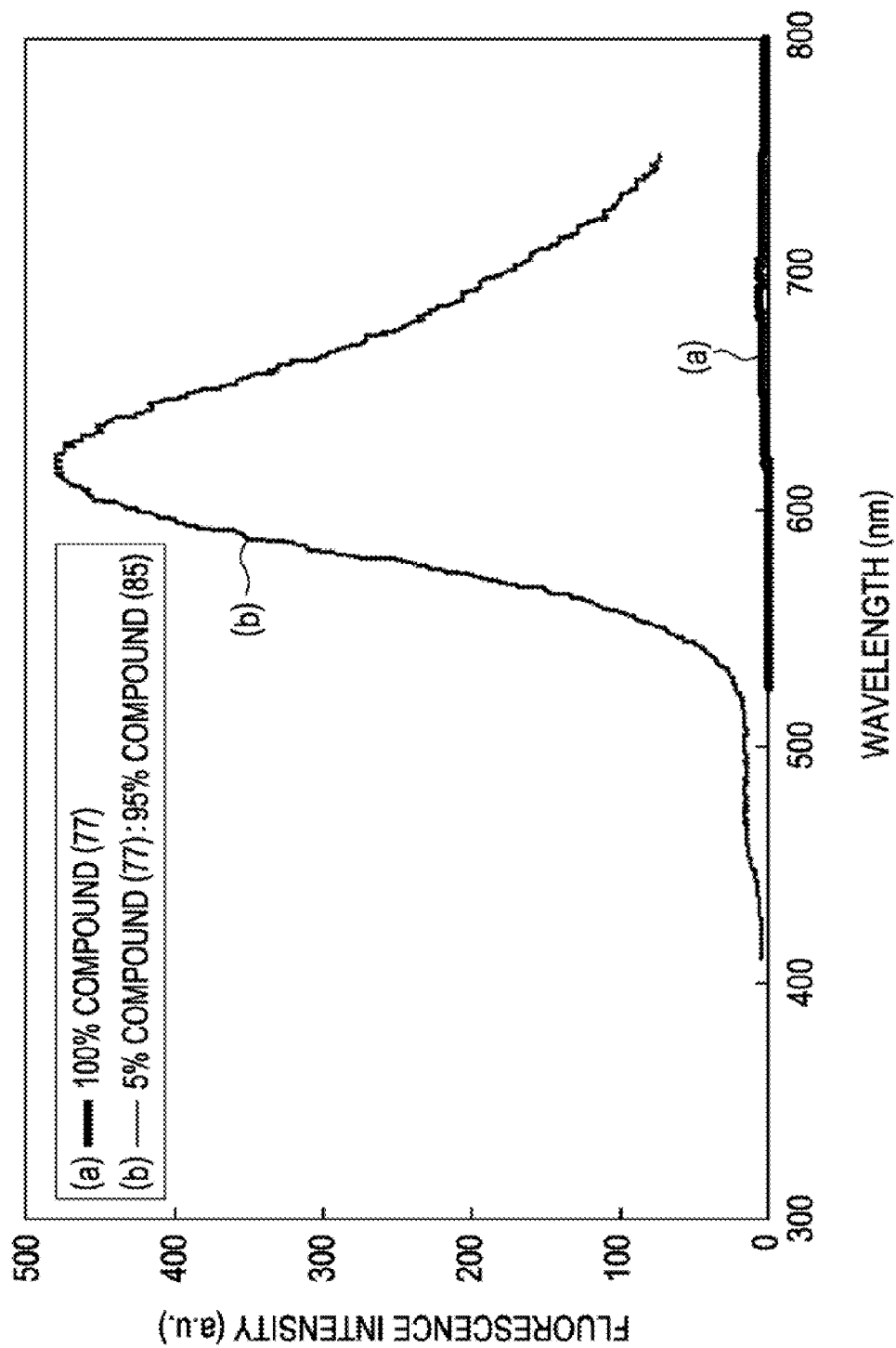
FIG. 13 is a graph showing a relationship between examples of organic light-emitting layers containing compound (77) and fluorescence intensities thereof in an Example.

FIG. 13 is a graph showing a relationship between examples of organic light-emitting layers containing compound (77) and fluorescence intensities thereof in an Example of the present invention.

FIG. 13 shows fluorescence spectra. In FIG. 13, the horizontal axis represents the wavelength (nm) and the vertical axis represents the fluorescence intensity (arbitrary units). In FIG. 13, (a) shows a fluorescence spectrum of a thin film composed of 100% of compound (77), and (b) shows a fluorescence spectrum of a mixed film (codeposited film) composed of 5% of compound (77) and 95% of host compound (85).

In FIG. 13, (a) is a fluorescence spectrum obtained by excitation at 484 nm, which is an absorption maximum of compound (77), and (b) is a fluorescence spectrum obtained by excitation at 384 nm, which is an absorption maximum of host compound (85). In the codeposited film, fluorescence of host compound (85) was suppressed, and red fluorescence was observed from compound (77) as a result of energy transfer.

According to the fluorescence spectrum of the thin film composed of 100% of compound (77), which is shown by (a) in FIG. 13, it was found that the film could be used as a deep-red-light-emitting material having a fluorescence maximum of 695 nm. On the other hand, in the codeposited film shown by (b) of FIG. 13, the fluorescence intensity was increased by 100 times as compared with that of (a), which shows the result of the thin film composed of 100% of compound (77). This result suggested that the codeposited film can provide a good red-light-emitting element by combining with an appropriate filter.

(2) Preparation of Organic Electroluminescent Element

A double hetero-structured transmission-type organic electroluminescent element shown in FIG. 4 was prepared. This organic electroluminescent element included a hole-transporting layer 10 (see FIG. 4) including a first hole-transporting layer and a second hole-transporting layer and a light-emitting layer composed of a mixed film (codeposited film) containing compound (77) and host compound (85). The first hole-transporting layer was composed of m-MT-DATA. The second hole-transporting layer was composed of α-NPD.

First, a glass substrate (30 mm×30 mm) having an anode composed of ITO with a thickness of 100 nm thereon was placed in a vacuum evaporation system. A metal mask having a plurality of unit openings each having dimensions of 2.0 mm×2.0 mm was disposed as an evaporation mask in proximity to the substrate. Next, m-MTDATA, which was a material constituting the first hole-transporting layer, was deposited by a vacuum evaporation method so as to have a thickness of 110 nm in a vacuum of $10^{-4}$ Pa or less. Subsequently, α-NPD, which was a material constituting the second hole-transporting layer, was deposited so as to have a thickness of 140 nm.

Furthermore, as materials constituting the light-emitting layer, compound (77) and host compound (85) were deposited on the second hole-transporting layer so as to have a thickness of 55 nm. In this step, compound (77) and host compound (85) were deposited so that the ratio of compound (77):host compound (85) was 5%:95%. Furthermore, as an electron-transporting layer, tris(8-quinolinol)aluminum ($Alq_3$) was deposited on the light-emitting layer so as to have a thickness of 30 nm. The deposition rate in each of these steps was 0.2 nm/sec.

A stacked film of magnesium (Mg) and silver (Ag) was used as a material constituting a cathode. A Mg film having a thickness of 50 nm and a Ag film having a thickness of 150 nm were formed by vacuum evaporation at a deposition rate of 1 nm/sec. Thus, the organic electroluminescent element shown in FIG. 4 was prepared.

(3) Characteristics of Organic Electroluminescent Element

A forward-bias direct-current voltage was applied to the organic electroluminescent element prepared as described above in a nitrogen atmosphere to evaluate luminous characteristics. The luminescent color was red. As a result of spectrometry, an emission spectrum similar to that shown in FIG. 13 was obtained. A spectrometer including a photodiode array manufactured by Otsuka Electronics Co., Ltd. as a detector was used in the spectrometry. In addition, a voltage-luminance characteristic and an external quantum efficiency were measured.

Figure 14:
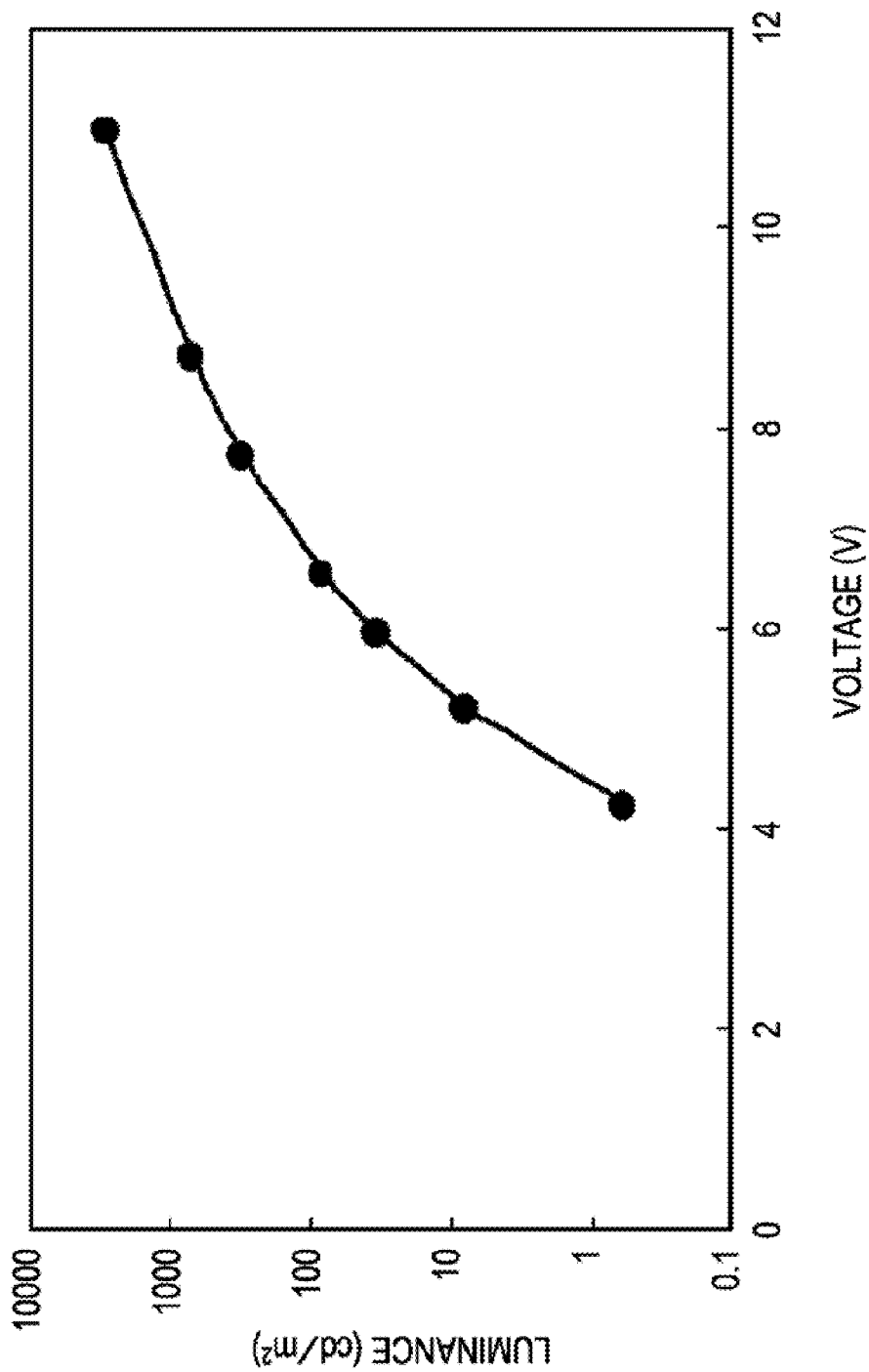
FIG. 14 is a graph showing an example of a voltage-luminance characteristic of an organic electroluminescent element in the Example.

FIG. 14 is a graph showing an example of the voltage-luminance characteristic of the organic electroluminescent element in the Example. In FIG. 14, the horizontal axis represents the applied voltage (V) and the vertical axis represents the luminance ($cd/m^2$).

Figure 15:
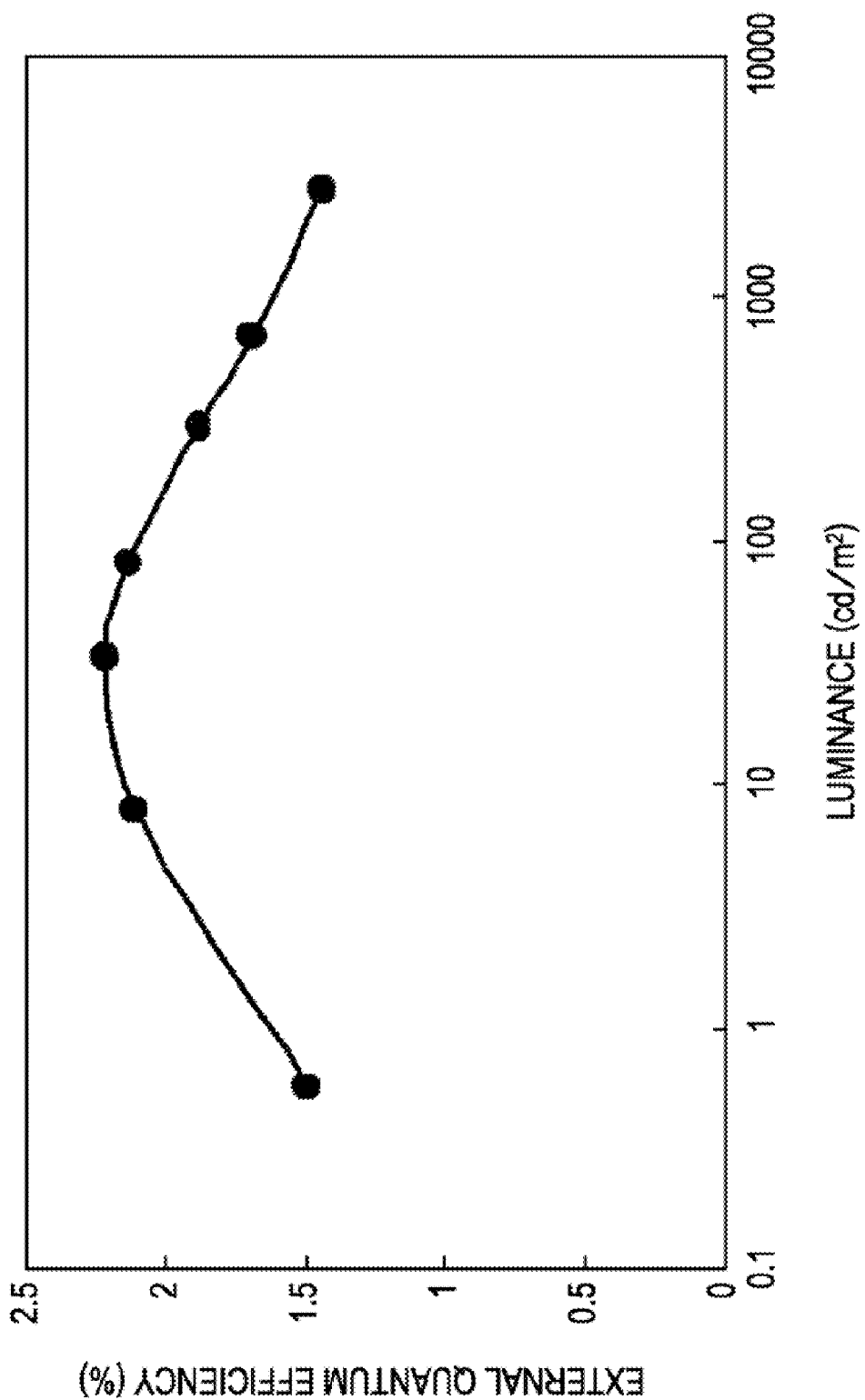
FIG. 15 is a graph showing an example of a luminance-external quantum efficiency characteristic of the organic electroluminescent element in the Example.

FIG. 15 is a graph showing an example of a luminance-external quantum efficiency characteristic of the organic electroluminescent element in the Example of the present invention. In FIG. 15, the horizontal axis represents the luminance ($cd/m^2$) and the vertical axis represents the external quantum efficiency (%).

Figure 16:
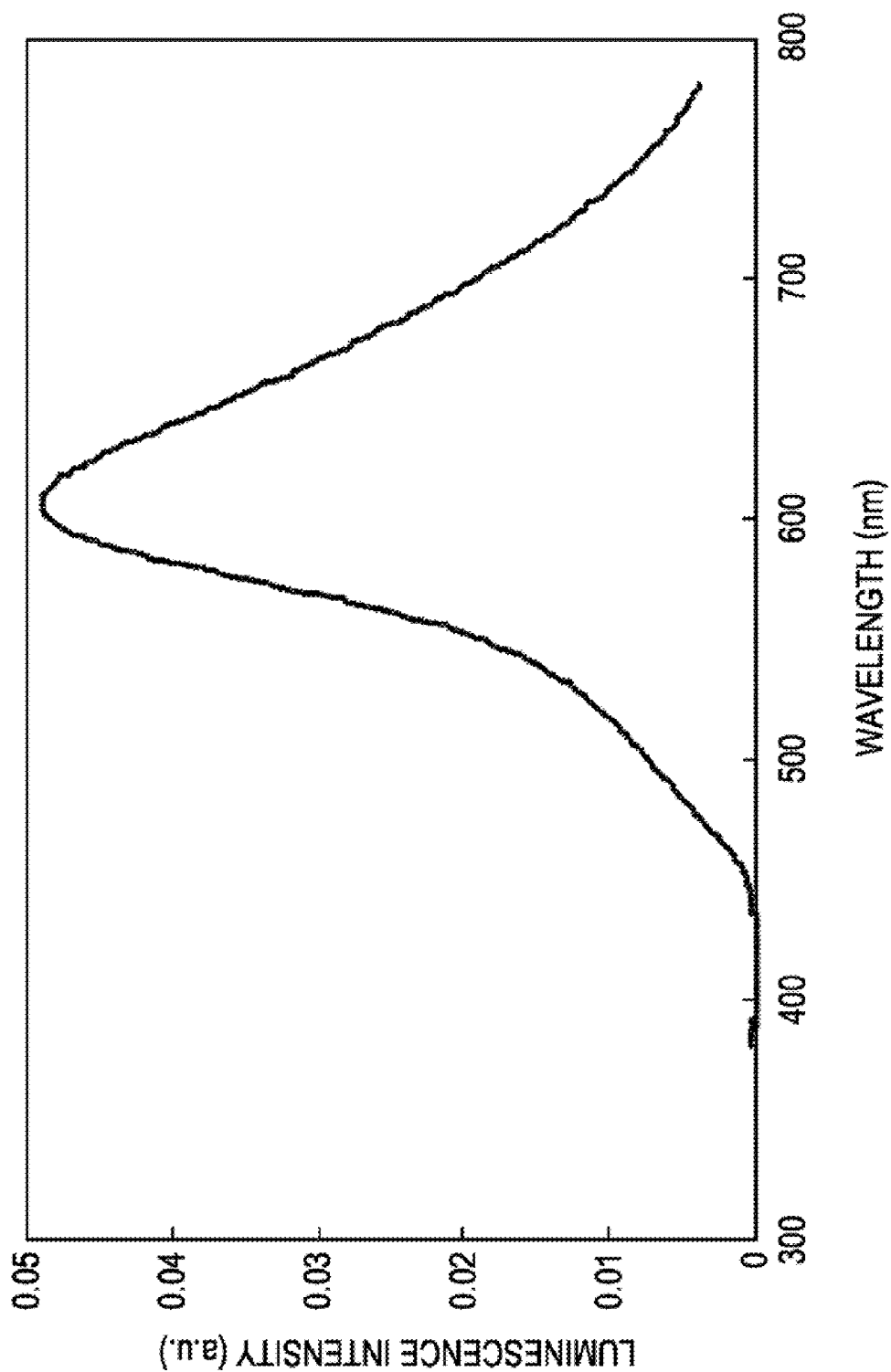
FIG. 16 is a graph showing an example of an emission spectrum of the organic electroluminescent element in the Example.

FIG. 16 is a graph showing an example of an emission spectrum (organic electroluminescence spectrum) of the organic electroluminescent element in the Example of the present invention. In FIG. 16, the horizontal axis represents the wavelength (nm) and the vertical axis represents the luminescence intensity (arbitrary units).

As shown in FIGS. 14 and 15, in the measurement of the voltage-luminance characteristic, a luminance of 500 $cd/m^2$ was obtained at 8 V, and the external quantum efficiency at this luminance was very high; 1.8%. FIG. 16 shows the organic electroluminescence spectrum at that time.

After the preparation of this organic electroluminescent element, the organic electroluminescent element was left to stand in a nitrogen atmosphere for one month. According to the result, degradation of the characteristics of the organic electroluminescent element was not observed. Furthermore, in order to forcibly degrade the organic electroluminescent element, light was continuously emitted from the organic electroluminescent element with an initial luminance of 100 $cd/m^2$ while supplying a constant current. In this test, the time during which the luminance was decreased to the half of the initial value was 2,000 hours.

[Third Organic Electroluminescent Element]

Next, an organic electroluminescent element including an organic light-emitting layer containing compound (71) and host compound (86) below will be described.

(1) Configuration and Fluorescence Intensity of Organic Light-Emitting Layer Containing Compound (71)

A mixed film (codeposited film, thickness: 25 nm) containing compound (71) and host compound (86) (known as a common name of ADN) was formed on a glass substrate by a vacuum evaporation method in a vacuum of $10^{-4}$ Pa or less.

Compound (86): 9,10-Di(2-naphthyl)anthracene

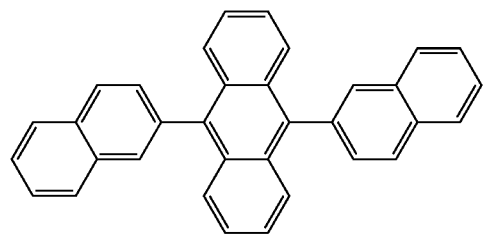

Figure 17:
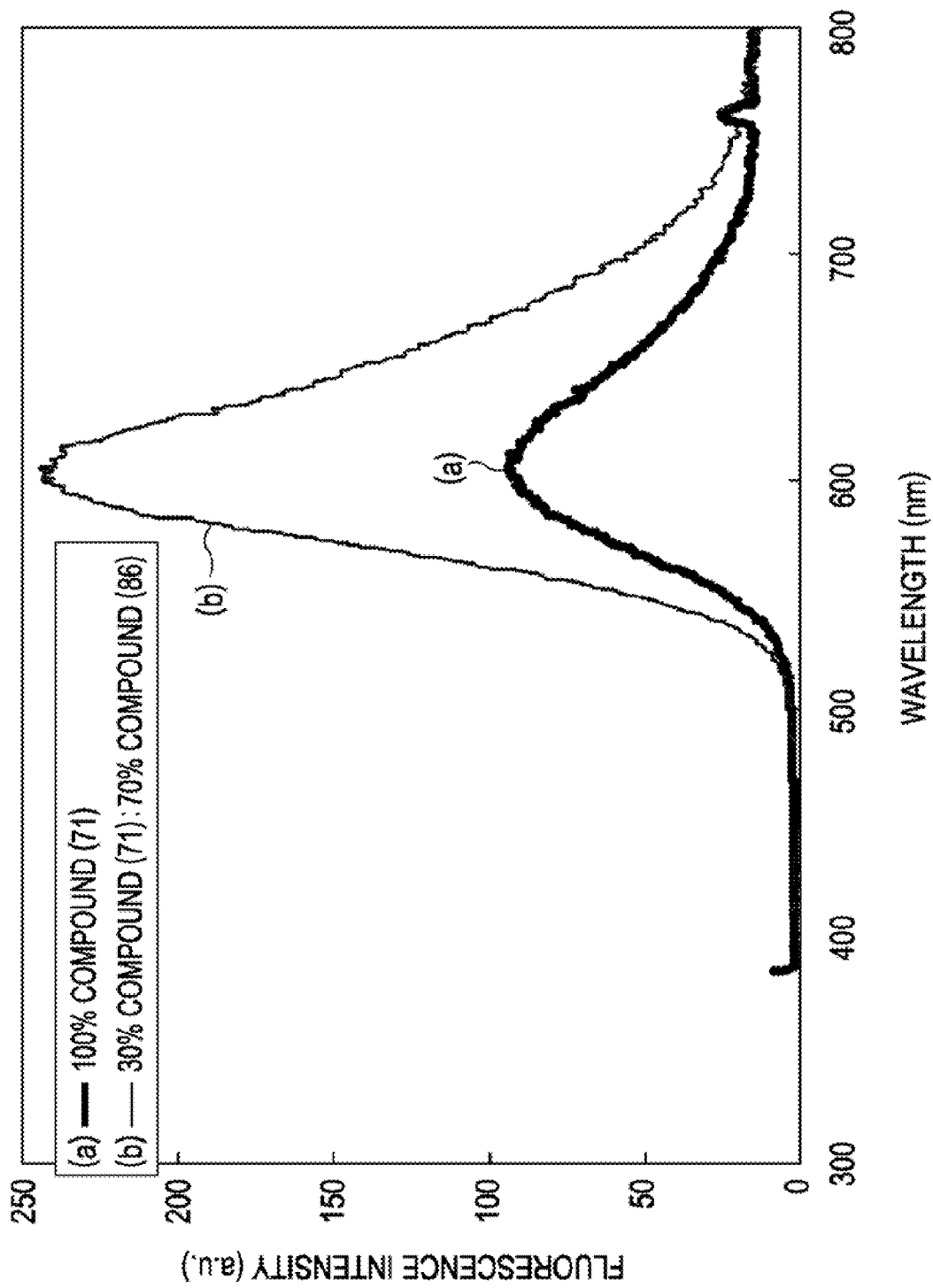
FIG. 17 is a graph showing a relationship between examples of organic light-emitting layers containing compound (71) and fluorescence intensities thereof in an Example.

FIG. 17 is a graph showing a relationship between examples of organic light-emitting layers containing compound (71) and fluorescence intensities thereof in an Example of the present invention.

FIG. 17 shows fluorescence spectra. In FIG. 17, the horizontal axis represents the wavelength (nm) and the vertical axis represents the fluorescence intensity (arbitrary units). In FIG. 17, (a) shows a fluorescence spectrum of a thin film composed of 100% of compound (71), and (b) shows a fluorescence spectrum of a mixed film (codeposited film) composed of 30% of compound (71) and 70% of host compound (86).

In FIG. 17, (a) is a fluorescence spectrum obtained by excitation at 453 nm, which is an absorption maximum of compound (71), and (b) is a fluorescence spectrum obtained by excitation at 382 nm, which is an absorption maximum of host compound (86). In the codeposited film, fluorescence of host compound (86) was not observed, and red fluorescence was observed from compound (71) as a result of energy transfer. In the codeposited film, the fluorescence intensity was increased by 2.3 times. This result suggested that the codeposited film can provide a good red-light-emitting element by combining with an appropriate filter.

(2) Preparation of Organic Electroluminescent Element

A double hetero-structured transmission-type organic electroluminescent was prepared as in the above-described first organic electroluminescent element except that a light-emitting layer having a thickness of 35 nm was codeposited on the second hole-transporting layer so that the ratio of compound (71):host compound (86) was 30%:70%.

(3) Characteristics of Organic Electroluminescent Element

A forward bias direct-current voltage was applied to the organic electroluminescent element prepared as described above in a nitrogen atmosphere to evaluate luminous characteristics. The luminescent color was red. As a result of spectrometry, an emission spectrum similar to that shown in FIG. 17 was obtained. A spectrometer including a photodiode array manufactured by Otsuka Electronics Co., Ltd. as a detector was used in the spectrometry. In addition, a voltage-luminance characteristic and an external quantum efficiency were measured.

Figure 18:
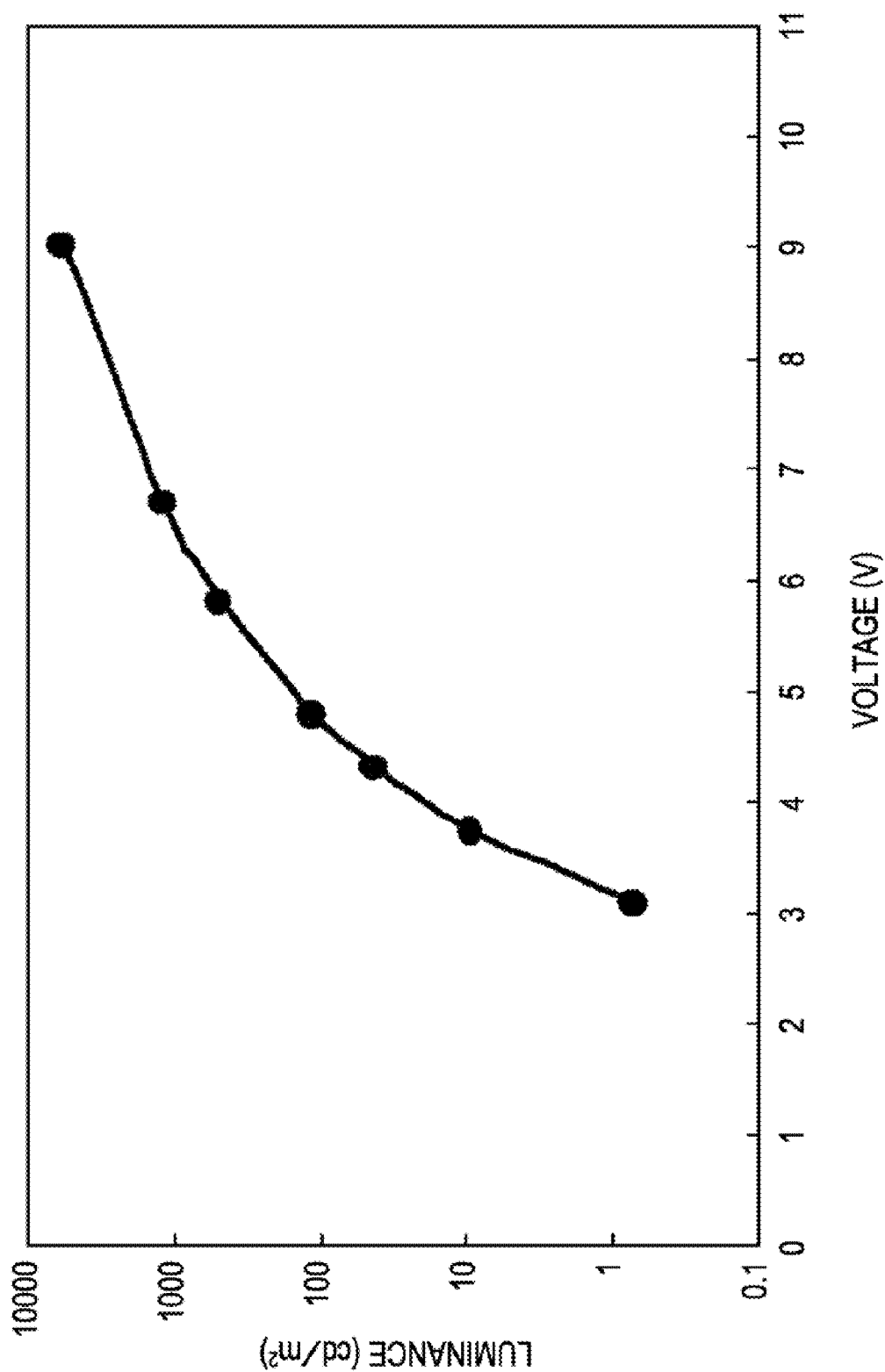
FIG. 18 is a graph showing an example of a voltage-luminance characteristic of an organic electroluminescent element in the Example.

FIG. 18 is a graph showing an example of the voltage-luminance characteristic of the organic electroluminescent element in the Example of the present invention. In FIG. 18, the horizontal axis represents the applied voltage (V) and the vertical axis represents the luminance ($cd/m^2$).

Figure 19:
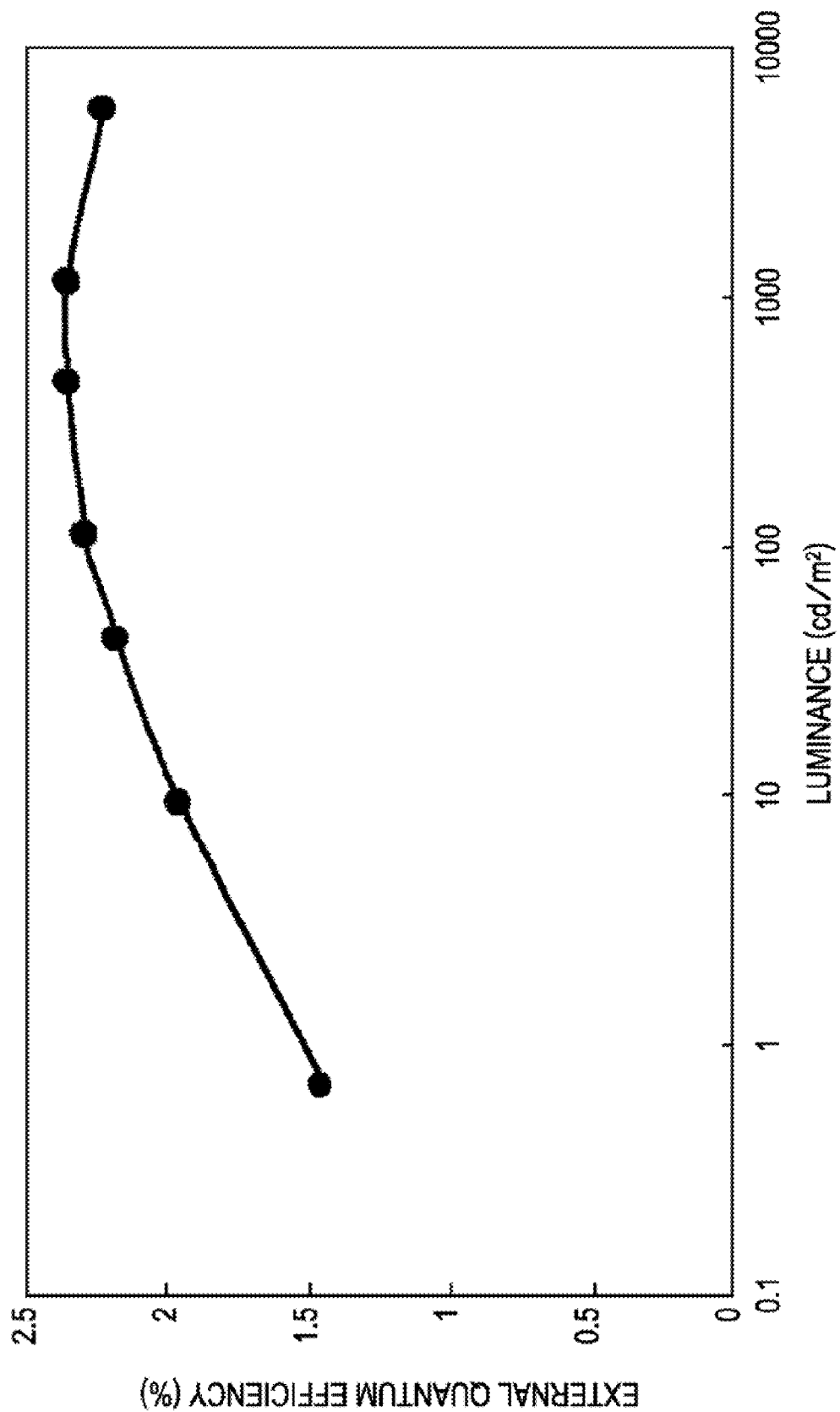
FIG. 19 is a graph showing an example of a luminance-external quantum efficiency characteristic of the organic electroluminescent element in the Example.

FIG. 19 is a graph showing an example of a luminance-external quantum efficiency characteristic of the organic electroluminescent element in the Example of the present invention. In FIG. 19, the horizontal axis represents the luminance ($cd/m^2$) and the vertical axis represents the external quantum efficiency (%).

Figure 20:
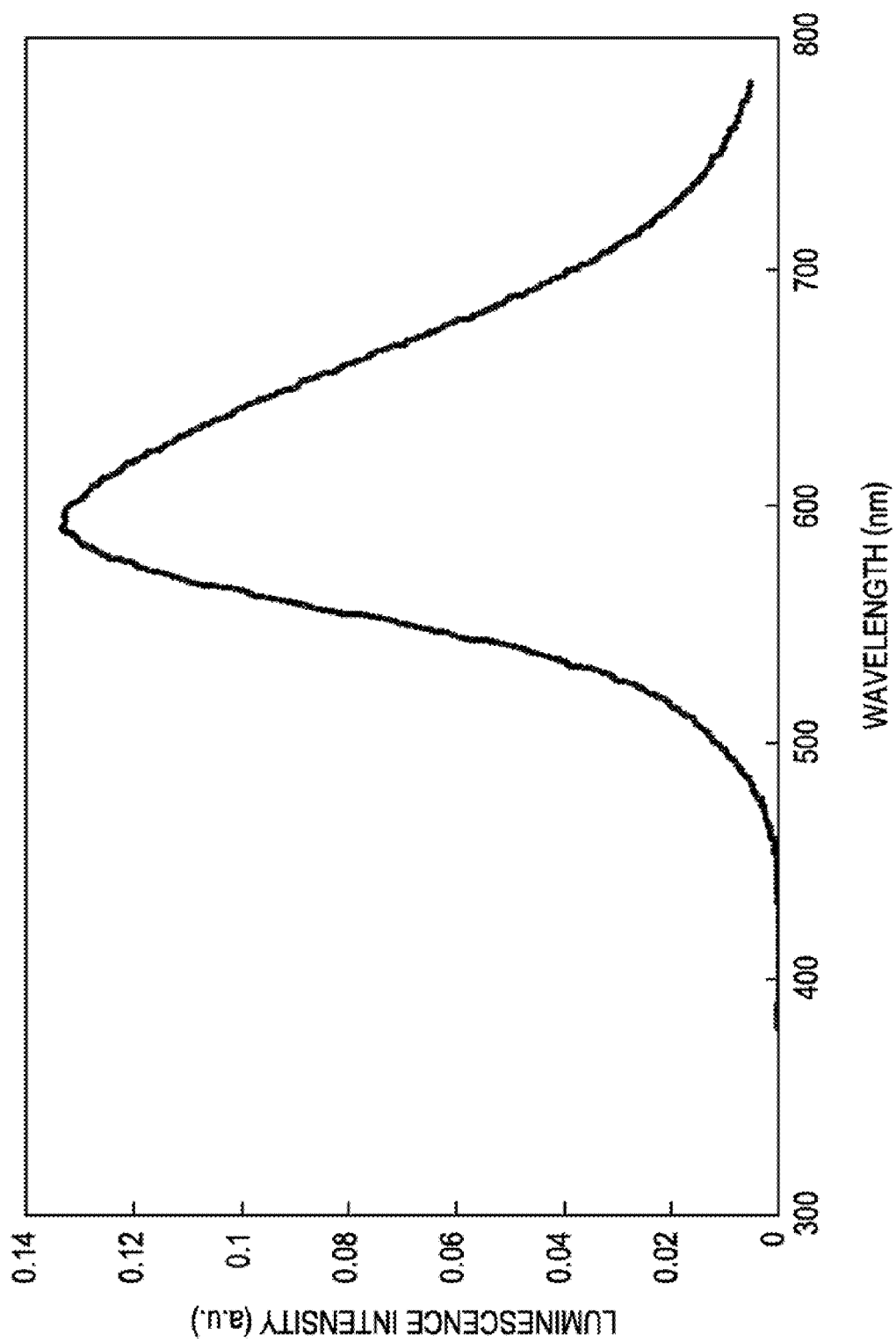
FIG. 20 is a graph showing an example of an emission spectrum of the organic electroluminescent element in the Example.

FIG. 20 is a graph showing an example of an emission spectrum (organic electroluminescence spectrum) of the organic electroluminescent element in the Example. In FIG. 20, the horizontal axis represents the wavelength (nm) and the vertical axis represents the luminescence intensity (arbitrary units).

As shown in FIGS. 18 and 19, in the measurement of the voltage-luminance characteristic, a luminance of 3,500 $cd/m^2$ was obtained at 8 V, and the external quantum efficiency at this luminance was very high; 2.4%. FIG. 20 shows the organic electroluminescence spectrum at that time.

After the preparation of this organic electroluminescent element, the organic electroluminescent element was left to stand in a nitrogen atmosphere for one month. According to the result, degradation of the characteristics of the organic electroluminescent element was not observed. Furthermore, in order to forcibly degrade the organic electroluminescent element, light was continuously emitted from the organic electroluminescent element with an initial luminance of 100 $cd/m^2$ while supplying a constant current. In this test, the time during which the luminance was decreased to the half of the initial value was 2,100 hours.

[Fourth Organic Electroluminescent Element]

Next, an organic electroluminescent element including an organic light-emitting layer containing compound (77) and host compound (86) below will be described.

(1) Configuration and Fluorescence Intensity of Organic Light-Emitting Layer Containing Compound (77)

A mixed film (codeposited film, thickness: 25 nm) containing compound (77) and host compound (86) was formed on a glass substrate by a vacuum evaporation method in a vacuum of $10^{-4}$ Pa or less.

Figure 21:
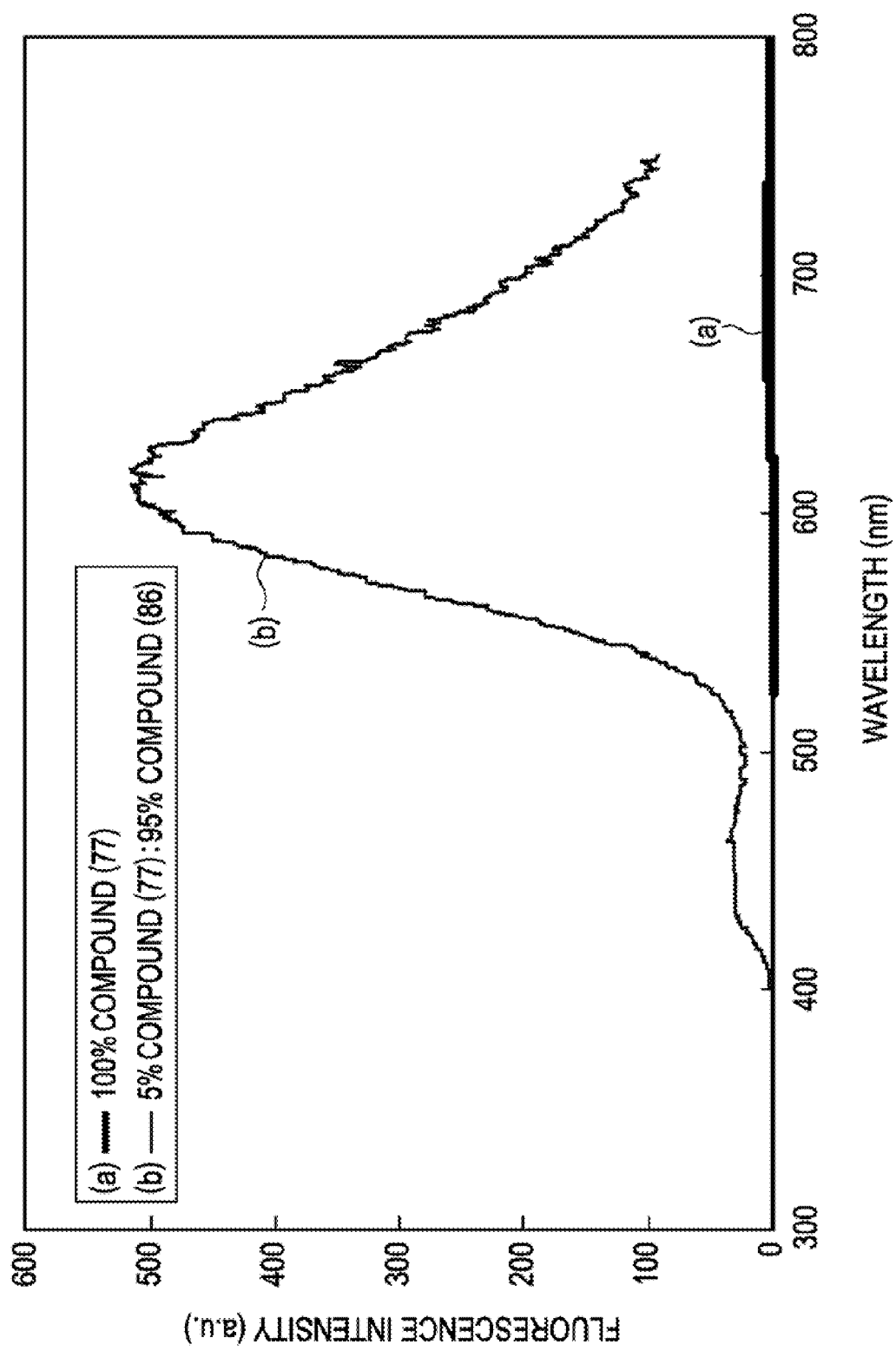
FIG. 21 is a graph showing a relationship between examples of organic light-emitting layers containing compound (77) and fluorescence intensities thereof in an Example.

FIG. 21 is a graph showing a relationship between examples of organic light-emitting layers containing compound (77) and fluorescence intensities thereof in an Example of the present invention.

FIG. 21 shows fluorescence spectra. In FIG. 21, the horizontal axis represents the wavelength (nm) and the vertical axis represents the fluorescence intensity (arbitrary units). In FIG. 21, (a) shows a fluorescence spectrum of a thin film composed of 100% of compound (77), and (b) shows a fluorescence spectrum of a mixed film (codeposited film) composed of 5% of compound (77) and 95% of host compound (86).

In FIG. 21, (a) is a fluorescence spectrum obtained by excitation at 484 nm, which is an absorption maximum of compound (77), and (b) is a fluorescence spectrum obtained by excitation at 382 nm, which is an absorption maximum of host compound (86). In the codeposited film, fluorescence of host compound (86) was suppressed, and instead, red fluorescence was observed from compound (77) as a result of energy transfer. In the codeposited film, the fluorescence intensity was increased by 110 times. This result suggested that the codeposited film can provide a good red-light-emitting element by combining with an appropriate filter.

(2) Preparation of Organic Electroluminescent Element

A double hetero-structured transmission-type organic electroluminescent was prepared as in the above-described first organic electroluminescent element except that a light-emitting layer having a thickness of 50 nm was codeposited on the second hole-transporting layer so that the ratio of compound (77):host compound (86) was 5%:95%, and tris (8-quinolinol)aluminum ($Alq_3$) was further deposited as an electron-transporting layer on the light-emitting layer so as to have a thickness of 20 nm.

(3) Characteristics of Organic Electroluminescent Element

A forward bias direct-current voltage was applied to the organic electroluminescent element prepared as described above in a nitrogen atmosphere to evaluate luminous characteristics. The luminescent color was red. As a result of spectrometry, an emission spectrum similar to that shown in FIG. 21 was obtained. A spectrometer including a photodiode array manufactured by Otsuka Electronics Co., Ltd. as a detector was used in the spectrometry. In addition, a voltage-luminance characteristic and an external quantum efficiency were measured.

Figure 22:
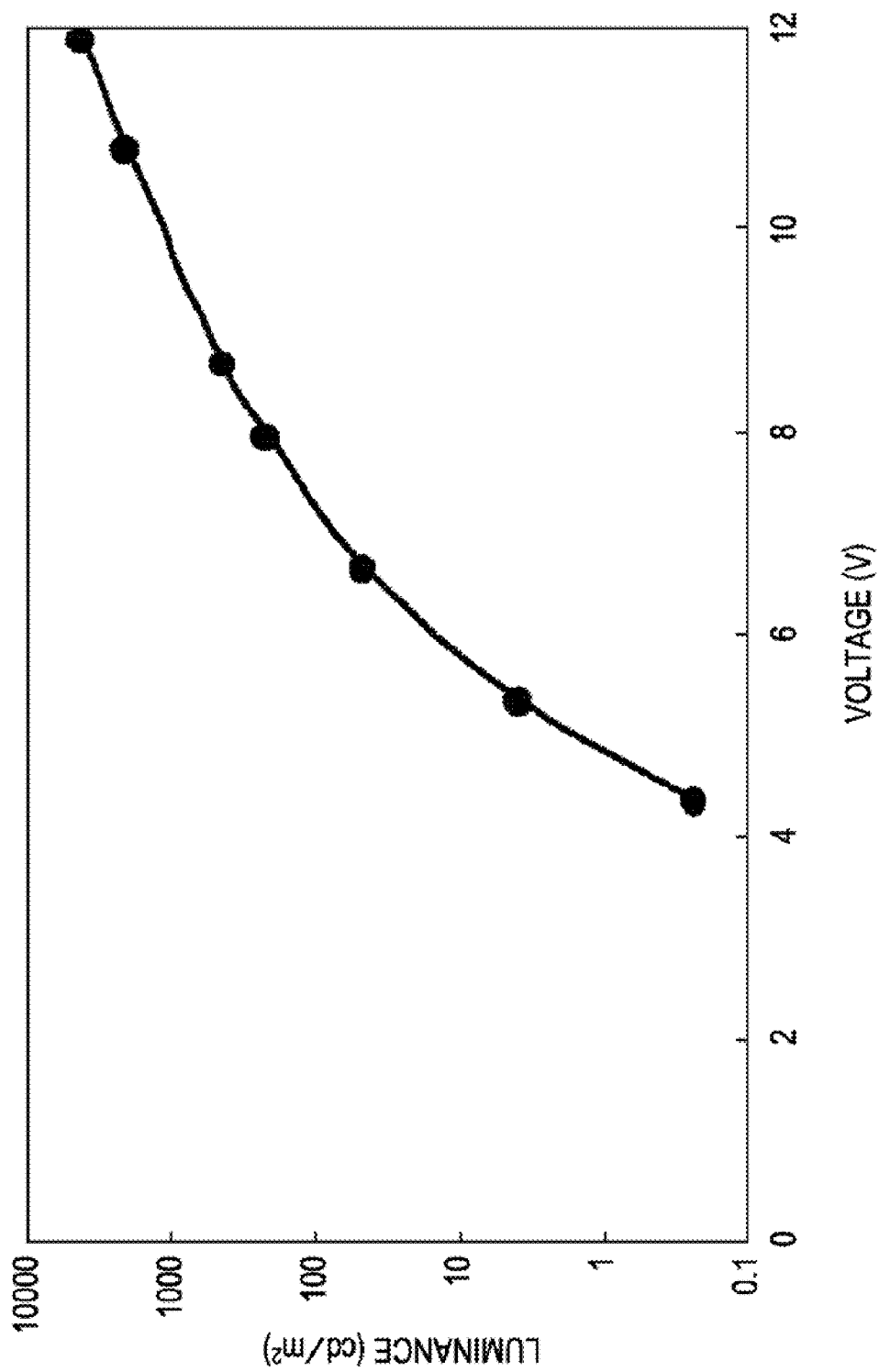
FIG. 22 is a graph showing an example of a voltage-luminance characteristic of an organic electroluminescent element in the Example.

FIG. 22 is a graph showing an example of the voltage-luminance characteristic of the organic electroluminescent element in the Example. In FIG. 22, the horizontal axis represents the applied voltage (V) and the vertical axis represents the luminance ($cd/m^2$).

Figure 23:
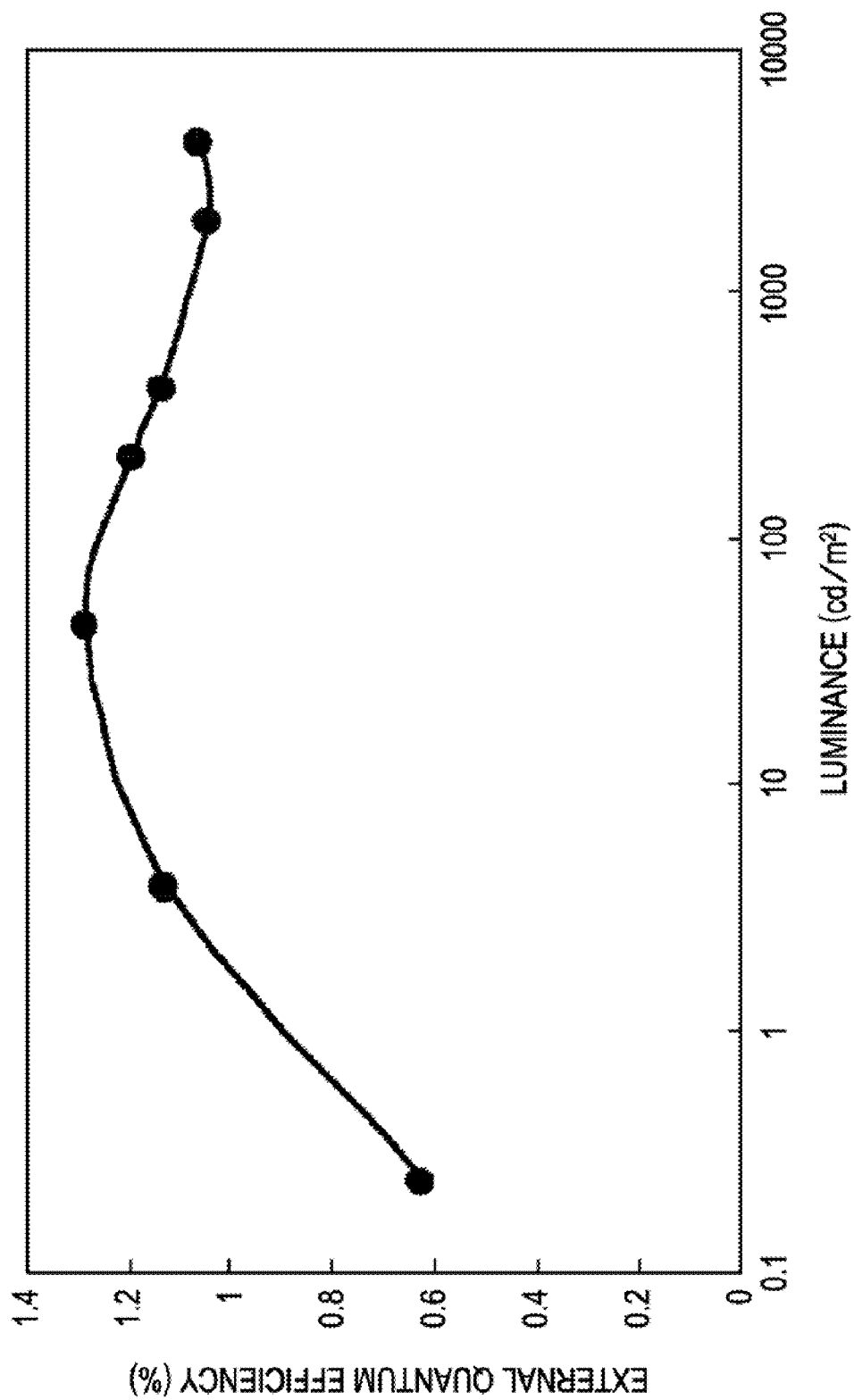
FIG. 23 is a graph showing an example of a luminance-external quantum efficiency characteristic of the organic electroluminescent element in the Example.

FIG. 23 is a graph showing an example of a luminance-external quantum efficiency characteristic of the organic electroluminescent element in the Example. In FIG. 23, the horizontal axis represents the luminance ($cd/m^2$) and the vertical axis represents the external quantum efficiency (%).

Figure 24:
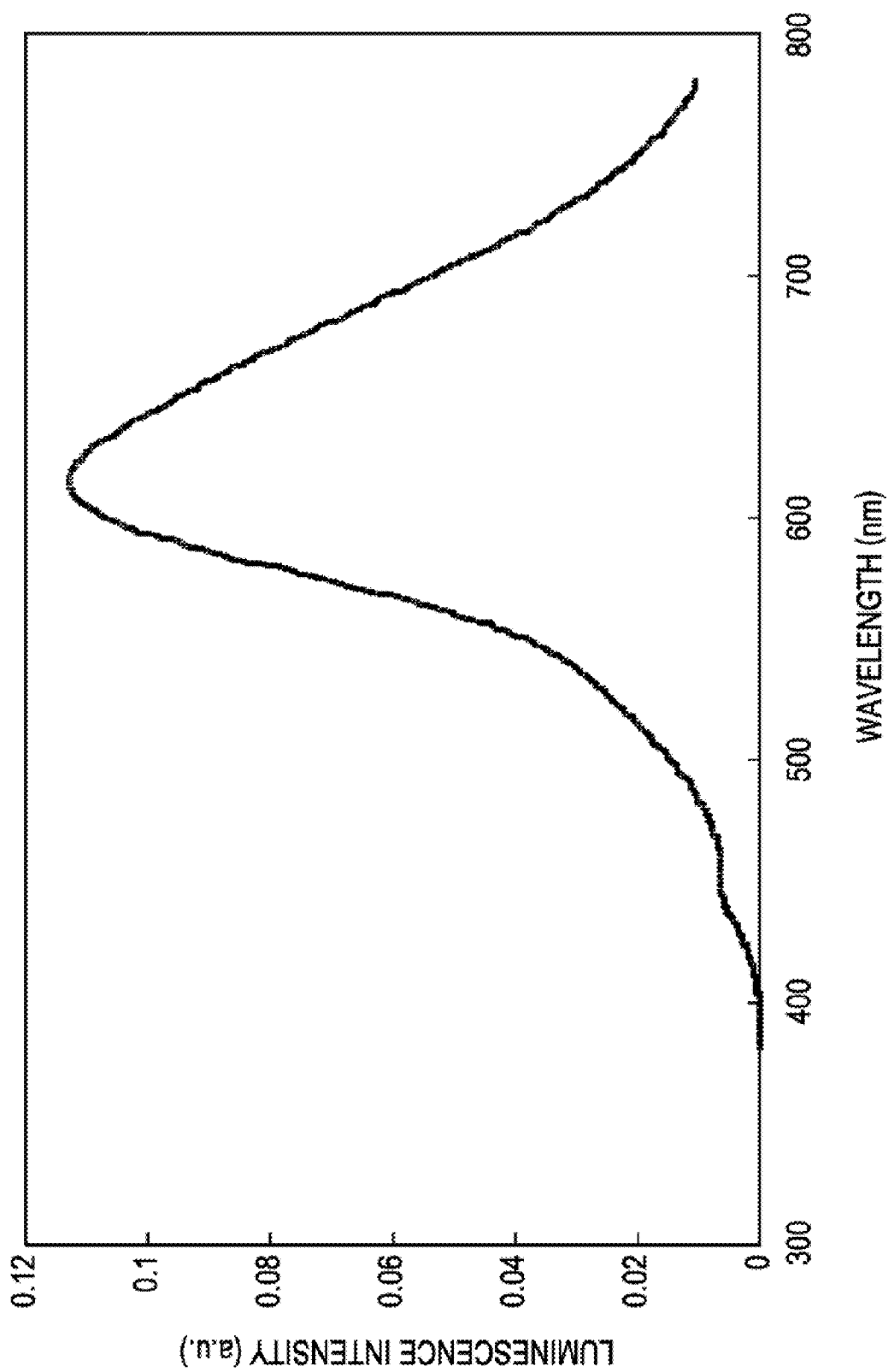
FIG. 24 is a graph showing an example of an emission spectrum of the organic electroluminescent element in the Example.

FIG. 24 is a graph showing an example of an emission spectrum (organic electroluminescence spectrum) of the organic electroluminescent element in the Example. In FIG. 24, the horizontal axis represents the wavelength (nm) and the vertical axis represents the luminescence intensity (arbitrary units).

As shown in FIGS. 22 and 23, in the measurement of the voltage-luminance characteristic, a luminance of 220 $cd/m^2$ was obtained at 8 V, and the external quantum efficiency at this luminance was very high; 1.2%. FIG. 24 shows the organic electroluminescence spectrum at that time.

After the preparation of this organic electroluminescent element, the organic electroluminescent element was left to stand in a nitrogen atmosphere for one month. According to the result, degradation of the characteristics of the organic electroluminescent element was not observed. Furthermore, in order to forcibly degrade the organic electroluminescent element, light was continuously emitted from the organic electroluminescent element with an initial luminance of 100 $cd/m^2$ while supplying a constant current. In this test, the time during which the luminance was decreased to the half of the initial value was 1,800 hours.

In the above-described first organic electroluminescent element to fourth organic electroluminescent element, host compound (87) or host compound (88) described below may be used as the host compound. Furthermore, the combination of the aromatic amine compound and the host compound may be changed.

Next, synthesis examples of aromatic amine compounds according to embodiments and host compounds will be described.

[Synthesis Examples of Aromatic Amine Compound]

Synthesis examples of compound (71) and compound (77) according to embodiments will now be described with reference to FIGS. 7 and 8, respectively.

(1) Synthesis example of aromatic tertiary amine compound (71)

Compound (71):

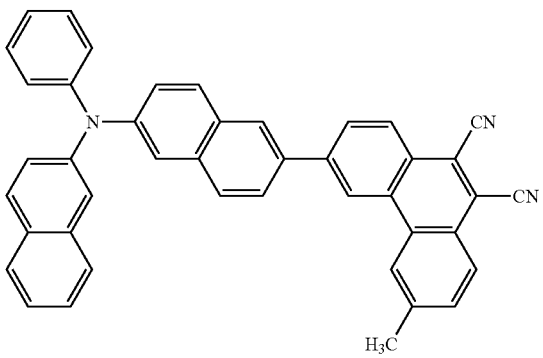

(1-1) Synthesis Example of Compound (72)

First, 48.0 g (0.24 mol) of compound A1 (4-bromobenzyl cyanide, $C_8H_6BrN$) and 96.4 g (0.73 mol) of compound A2 (p-methylbenzyl cyanide (p-xylyl cyanide, $C_9H_9N$) were dissolved in 1.5 L of anhydrous ethyl ether ($Et_2O$). Subsequently, 249 g (0.98 mol) of iodine ($I_2$) was added to the solution. Next, 500 mL of a methanol (MeOH) solution containing 106 g (1.96 mol) of sodium methoxide (NaOMe) was added dropwise to the reaction solution while maintaining the temperature of the reaction solution to 15° C. on an ice bath. The reaction solution was stirred for 30 minutes. The precipitated crystals were separated by filtration, and then washed with MeOH. Thus, 95.2 g of a crude product containing compound (72) and a by-product was obtained.

(1-2) Synthesis Example of Compound (73)

Next, 93.5 g of the crude product containing compound (72) was dissolved in 19 L of toluene. Subsequently, 5 g (19.7 mmol) of iodine ($I_2$) was added to the solution. The resulting reaction solution was irradiated with ultraviolet light under stirring for two days while supplying oxygen. The reaction solution was concentrated until the volume of the solution was decreased to half; and the precipitated crystals were separated by filtration. The crude crystals were then purified by silica gel chromatography (eluate: toluene). Thus, 17 g of a crude product containing compound (73) and a by-product was obtained.

(1-3) Synthesis Example of Compound (74)

Next, 28.4 g (0.26 mol) of 2,6-lutidine (2,6-dimethylpyridine, $C_7H_9N$) and 44.4 g (0.16 mol) of trifluoromethanesulfonic acid ($CF_3SO_3H$) were added to 450 mL of a dichloromethane ($CH_2Cl_2$) solution containing 29.6 g (0.13 mol) of compound A3 (6-bromonaphthol, 6-bromo-naphthalen-2-ol, $C_{10}H_7BrO$). The reaction solution was stirred at 35° C. for one hour. The reaction solution was then purified by silica gel chromatography (eluate: toluene). Thus, 46.0 g of compound (74) was obtained (yield: 98%).

(1-4) Synthesis Example of Compound (75)

Next, 45.0 g (0.13 mol) of Compound (74), 27.9 g (0.13 mol) of compound A4 (N-phenyl-2-naphthylamine, 2-anilinonaphthalene, $C_{16}H_{13}N$), 0.70 g (3.1 mmol) of $Pd(OAc)_2$, 2.85 g (14.1 mmol) of tri(tert-butyl)phosphine ($P(t-Bu)_3$, $Bu=C_4H_9$), 14.7 g (0.15 mol) of sodium tert-butoxide (Na(O-tBu)), and 418 mL of xylenes were mixed under an Ar gas flow, and the reaction solution was stirred at 120° C. for two hours. Water was added to the reaction solution to separate the resulting mixture. The organic layer was concentrated under reduced pressure. The resulting crude product was then purified by silica gel chromatography (eluate: toluene). Thus, 53.9 g of compound (75) was obtained (yield: 86%).

(1-5) Synthesis Example of Compound (76)

Next, 40.5 g (0.082 mol) of Compound (75), 25.0 g (0.098 mol) of compound A5 (bis(pinacolate)diboron, $C_{12}H_{24}B_2O_4$), 3.9 g (5.3 mmol) of bis(diphenylphosphino)ferrocene)dichloropalladium ($PdCl_2(dppf)$, $C_{34}H_{28}FeP_2 \cdot PdCl_2$), 1.4 g (2.5 mol) of bis(diphenylphosphino)ferrocene (dppf, $C_{34}H_{28}FeP_2$), 24.3 g (0.25 mol) of potassium acetate (KOAc), and 486 mL of 1,4-dioxane ($C_4H_8O_2$) were mixed, and the mixture was refluxed for one night under an Ar gas flow to conduct a reaction. The resulting reaction solution was dried under reduced pressure. The crude product was then purified by silica gel chromatography (eluate: toluene/hexane=2/3 to 1/2). Thus, 25.0 g of compound (76) was obtained (yield: 65%).

(1-6) Synthesis Example of Compound (71)

Next, 13.0 g (27.6 mmol) of Compound (76), 16 g of the crude product containing compound (73) in an amount of about 35%, 1.8 g (1.6 mmol) of tetrakis(triphenylphosphine)palladium(0) ($Pd(PPh_3)_4$, $Pd[P(C_6H_5)_3]_4$), 96 mL of a 1 M sodium carbonate ($Na_2CO_3$) solution, and 113 mL of 1,2-dimethoxyethane (DME) (ethylene glycol dimethyl ether, $MeOCH_2CH_2OMe$) were mixed, and the resulting reaction solution was refluxed for one night under an Ar gas flow to conduct a reaction. The reaction solution was dried under reduced pressure, and the resulting crude product was then purified by silica gel chromatography (eluate: toluene). Thus, 21 g of a crude product containing compound (71) was obtained. The crude product was purified by sublimation. Thus, 3.0 g (5.1 mmol) of pure compound (71) was obtained (yield after sublimation: 18%).

Figure 25:
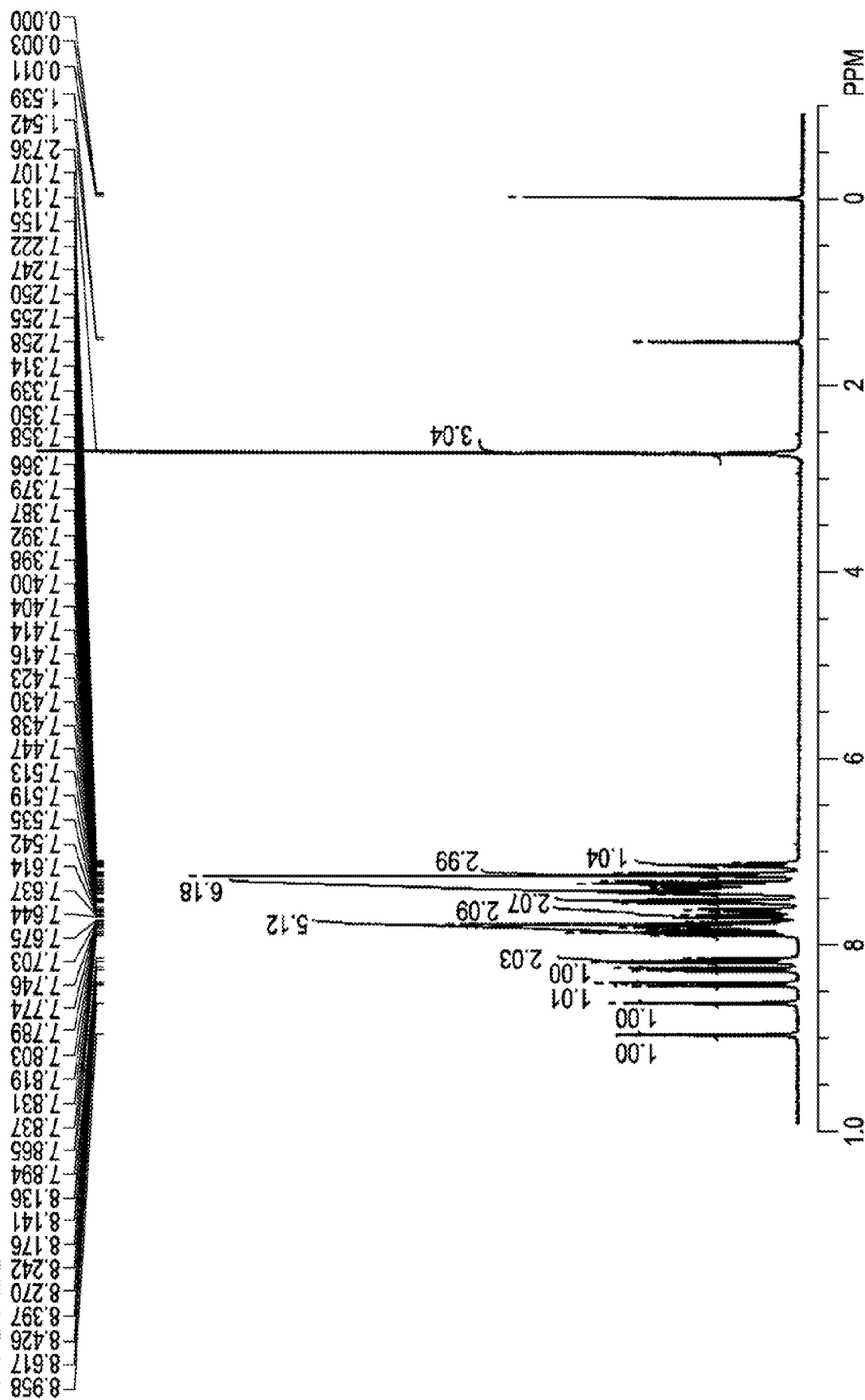
FIG. 25 is a chart showing a $^1$H NMR spectrum of compound (71) in an Example.

FIG. 25 is a chart showing a $^1$H NMR (nuclear magnetic resonance) spectrum of compound (71) in this Example of the present invention.

In FIG. 25, the horizontal axis represents the chemical shift (ppm) and the vertical axis represents the nuclear magnetic resonance signal intensity. A chemical shift value of each signal peak is shown in the upper part of the chart, and the signal intensity is shown near the signal peak. The NMR spectrum was measured with a JNM-AL300 FT NMR apparatus manufactured by JEOL Ltd.

δ ppm (300 MHz, $CDCl_3$); 2.74 (s, 3H), 7.13 (t, 1H), 7.22-7.26 (m, 2H), 7.31-7.45 (m, 6H), 7.52 (d, 2H), 7.62 (d, 1H), 7.69 (d, 1H), 7.75-7.89 (m, 5H), 8.14-8.18 (m, 2H), 8.26 (d, 1H), 8.42 (d, 1H), 8.62 (s, 1H), 8.96 (s, 1H).

Twenty four aromatic hydrogen atoms were observed relative to three aliphatic hydrogen atoms. This result corresponded to the molecular structure of compound (71).

Figure 26:
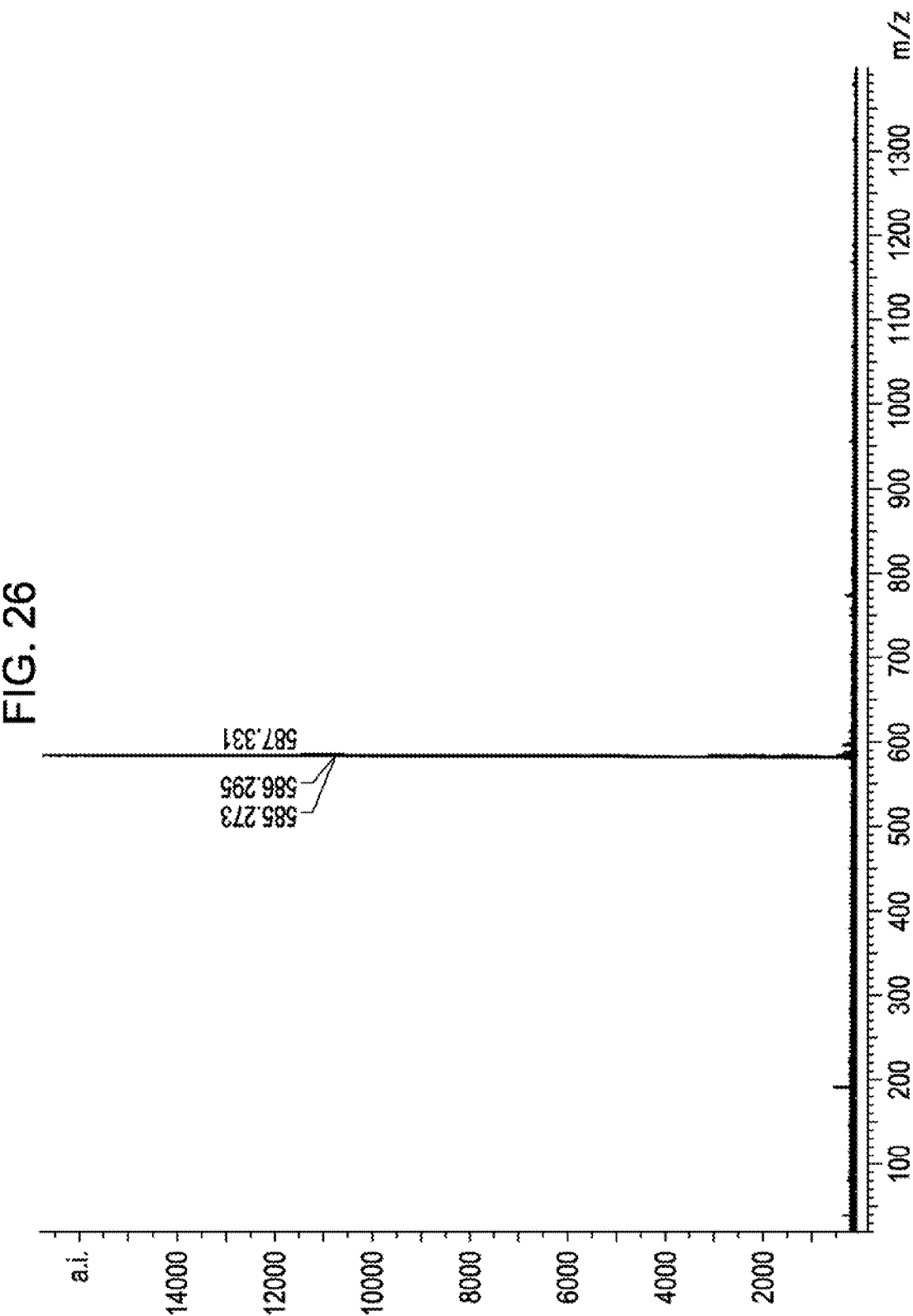
FIG. 26 is a chart showing a MALDI-TOF-MS spectrum of compound (71) in the Example.

FIG. 26 is a chart showing a matrix-assisted laser desorption/ionization time-of-flight mass spectrometer (MALDI-TOF-MS) spectrum of compound (71) in the Example.

The MS spectrum shown in FIG. 26 was measured with an apparatus of KRATOS AXIMA-CFR manufactured by Shimadzu Corporation. The MS spectrum shows a calculated value of m/z (m: molecular weight, z: charge number) for each measured peak.

A calculated value of the molecular weight of compound (71) (chemical formula: $C_{43}H_{27}N_3$) is 585.69. As shown in FIG. 26, the value of m/z (m: molecular weight, z: charge number) and a pattern coefficient (coefficient of frequency of occurrence) for each measured peak were 585.22 (100%), 586.22 (47.6%), 587.23 (10.7%), and 588.23 (1.6%). The measured value of the molecular weight was 585.84.

The NMR spectrum shown in FIG. 25 and the MS spectrum shown in FIG. 26 showed that the synthesized compound (71) was the target compound.

Next, absorption and luminous characteristics of the synthesized compound (71) will be described. An absorption spectrum and an emission spectrum were measured with a U-3310 spectrophotometer and an FL-4500 fluorescence spectrophotometer, respectively, both of which were manufactured by Hitachi Ltd. In THF, compound (71) showed an absorption maximum of 425 nm, a molar extinction coefficient of 24,200, a fluorescence maximum of 641 nm, and a fluorescence quantum yield of 0.24.

According to differential thermal analysis (DSC), it was confirmed that compound (71) does not have a glass transition temperature and has a melting point of 307° C.

(2) Synthesis Example of Aromatic Tertiary Amine Compound (77)

Compound (77):

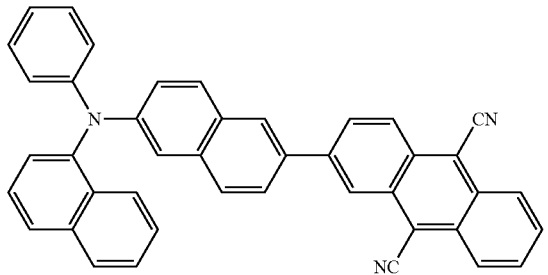

(2-1) Synthesis Example of Compound (78)

Compound (78) shown in FIG. 8 was synthesized by the same method as the method for synthesizing compound (75) shown in FIG. 7.

(2-2) Synthesis Example of Compound (79)

Compound (79) shown in FIG. 8 was synthesized by the same method as the method for synthesizing compound (76) shown in FIG. 7.

(2-3) Synthesis Example of Compound (80)

First, 18.0 g (0.45 mol) of 60% sodium hydride (NaH) from which oil had been removed in a darkroom was mixed with 1.2 L of dehydrated dimethyl sulfoxide (DMSO, $C_2H_6OS$) and 48.5 g (0.20 mol) of compound B2 (2-chloro-9,10-anthraquinone, $C_{14}H_7Cl_2$). Subsequently, 0.8 L of a dehydrated DMSO solution containing 91.8 g (0.45 mol) of trimethyliodosulfur (IV) ($Me_3S^+I^-$, $C_3H_9S^+I^-$) was added dropwise to the mixed solution in an argon atmosphere at 27° C. or lower over a period of one hour. The mixed solution was stirred at 25° C. for three hours and then poured into 4 L of ice water. The solution was stirred overnight. Ethyl acetate was then added to the solution to separate the resulting mixture. The organic layer was washed with water and saline solution, and dried over anhydrous magnesium sulfate. The resulting solution was then concentrated under reduced pressure to epoxidize compound B2. Thus, 52.8 g of a crude product solution of compound (epoxide) (80) was obtained (yield: 97%). Note that $C_3H_9S^+I^-$ is a salt of trimethylsulfonium ($C_3H_9S^+$) and $I^-$.

(2-4) Synthesis Example of Compound (81)

Next, 52.8 g (0.20 mol) of compound (80) was added to 2.0 L of an acetonitrile ($C_2H_3N$) solution containing 84.7 g (0.98 mol) of lithium bromide (LiBr) in an argon atmosphere in a darkroom. The mixture was stirred at 60° C. for 18 hours to conduct a reaction, and a precipitated solid was then separated by filtration. The resulting crude crystals were washed with acetonitrile. Thus, 57.3 g of an orange crystalline compound (81) in which epoxy rings of compound (80) were opened was obtained.

A method of obtaining compound (83) from compound (81) by way of compound (82) follows a general organic synthesis method. Specifically, by conducting a triethylamine ($NEt_3$)/pyridine:$SO_3$ oxidation of compound (81), —COH is selectively oxidized to —C═O to obtain aldehyde compound (82). Subsequently, nitrile compound (83) can be obtained from aldehyde compound (82) by way of an oxime using hydroxyammonium hydrochloride ($NH_4OH.HCl$).

(2-5) Synthesis Example of Compound (82)

More specifically, 40.5 g (0.4 mol) of triethylamine ($NEt_3$, $C_6H_{15}N$) and 63.7 g (0.4 mol) of pyridine-sulfur trioxide complex (sulfur trioxidepyridine salt, pyridine:$SO_3$ complex, $C_5H_5N.SO_3$) were added to 400 mL of a dehydrated DMSO solution containing 54.1 g (0.2 mol) of compound (81) at 37° C. or lower in an argon atmosphere. The mixture was stirred for two hours and then poured into water. The resulting precipitate was filtered, and the precipitate was suspended again in water. The suspension was stirred and then filtered. Next, the resulting product was suspended in methanol, and the suspension was stirred. Subsequently, the suspension was filtered. Thus, 30.8 g of orange crystalline compound (82) was obtained (yield: 57%).

(2-6) Synthesis Example of Compound (83)

Next, 15.3 g (0.22 mol) of hydroxyammonium hydrochloride ($NH_4OH.HCl$) and 26.9 g (0.10 mol) of compound (82) were added to 300 mL of a HOAc (wherein Ac represents $CH_3CO$, and thus HOAc represents acetic acid) solution containing 18.0 g (0.22 mol) of sodium acetate (NaOAc). The mixture was refluxed for 27 hours to conduct a reaction. The mixture was cooled and then poured into water. The resulting crystals were filtered. The crude crystals were sequentially washed with water and methanol, and then purified with a silica gel column (eluate: hot toluene). Subsequently, 15.0 g of the resulting crudely purified solid was recrystallized a plurality of times with tetrahydrofuran (THF, $C_4H_8O$). Thus, 2.2 g of bright yellow crystalline compound (83) was obtained (yield: 8.4%, purity: 98.7%).

(2-7) Synthesis Example of Compound (77)

Next, 3.80 g (8.07 mmol) of Compound (79), 2.12 g (8.07 mmol) of compound (83), 0.28 g (0.24 mmol) of tetrakis (triphenylphosphine)palladium(0) ($Pd(PPh_3)_4$, $Pd[P(C_6H_5)_3]_4$), 1.71 g (16.1 mmol) of sodium carbonate ($Na_2CO_3$), and 76 mL of 1,2-dimethoxyethane (DME, MeOCH$_2$CH$_2$OMe) were mixed, and the resulting reaction solution was refluxed under an Ar gas flow for 22 hours to conduct a reaction. The reaction solution was dried under reduced pressure, and the resulting crude product was purified by silica gel chromatography (eluate: hot toluene). As a result, 4.3 g of a red crude product was obtained (yield: 93%). This crude product was purified by sublimation. Thus, pure compound (77) is obtained.

Figure 27:
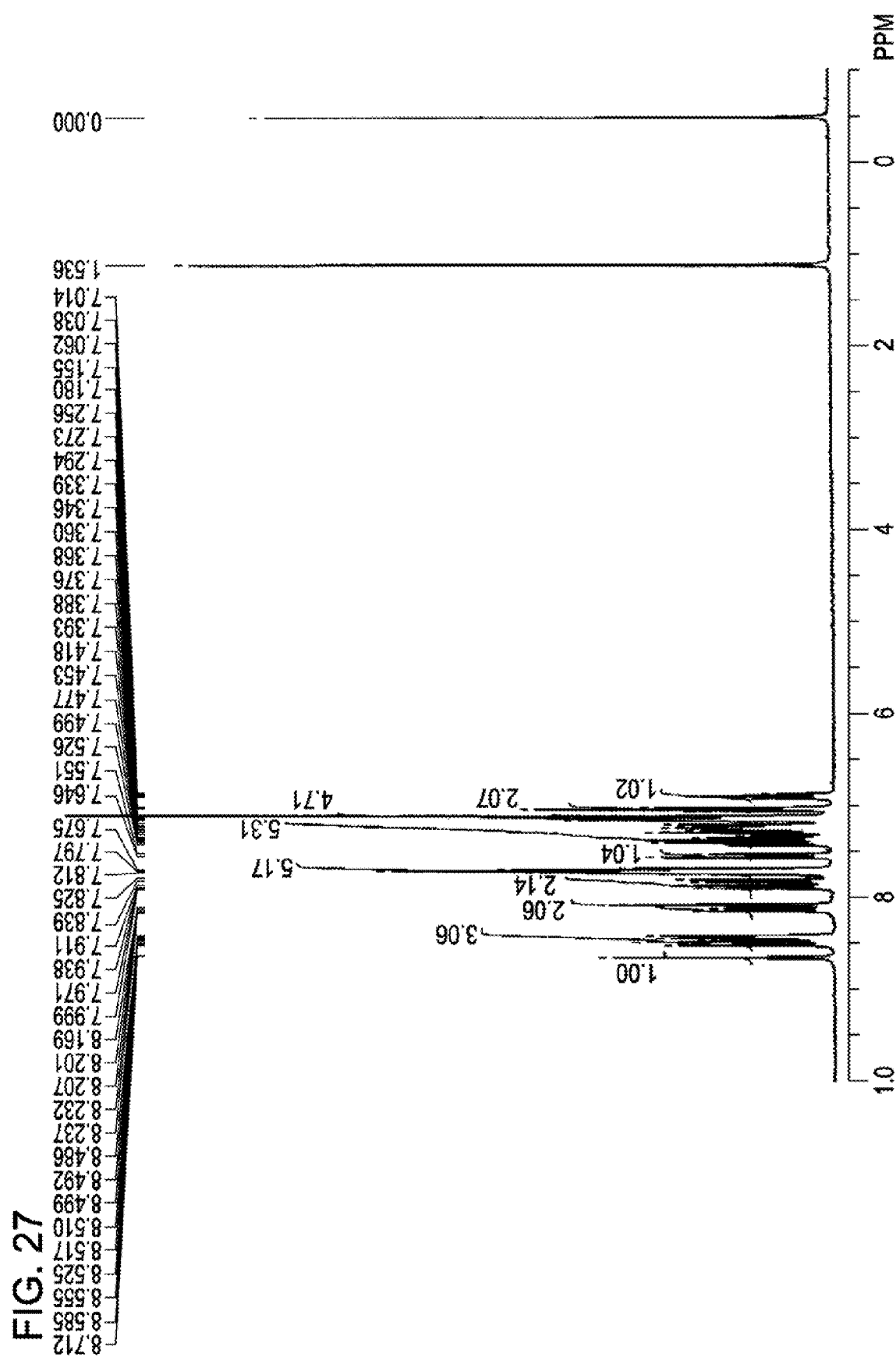
FIG. 27 is a chart showing a $^1$H NMR spectrum of compound (77) in an Example.

FIG. 27 is a chart showing a $^1$H NMR (nuclear magnetic resonance) spectrum of compound (77) in this Example.

In FIG. 27, the horizontal axis represents the chemical shift (ppm), and the vertical axis represents the nuclear magnetic resonance signal intensity. A chemical shift value of each signal peak is shown in the upper part of the chart, and the signal intensity is shown near the signal peak. The NMR spectrum was measured with a JNM-AL300 FT NMR apparatus manufactured by JEOL Ltd.

δ ppm (300 MHz, CDCl$_3$); 7.04 (t, 1H), 7.17 (d, 2H), 7.26-7.29 (m, 3H), 7.33-7.55 (m, 5H), 7.66 (d, 1H), 7.80-7.84 (m, 5H), 7.92 (d, 1H), 7.98 (d, 1H), 8.17 (s, 1H), 8.22 (d, 1H), 8.49-8.53 (m, 2H), 8.57 (d, 1H), 8.71 (s, 1H).

Twenty five aromatic hydrogen atoms were observed. This result corresponded to the molecular structure of compound (77).

Figure 28:
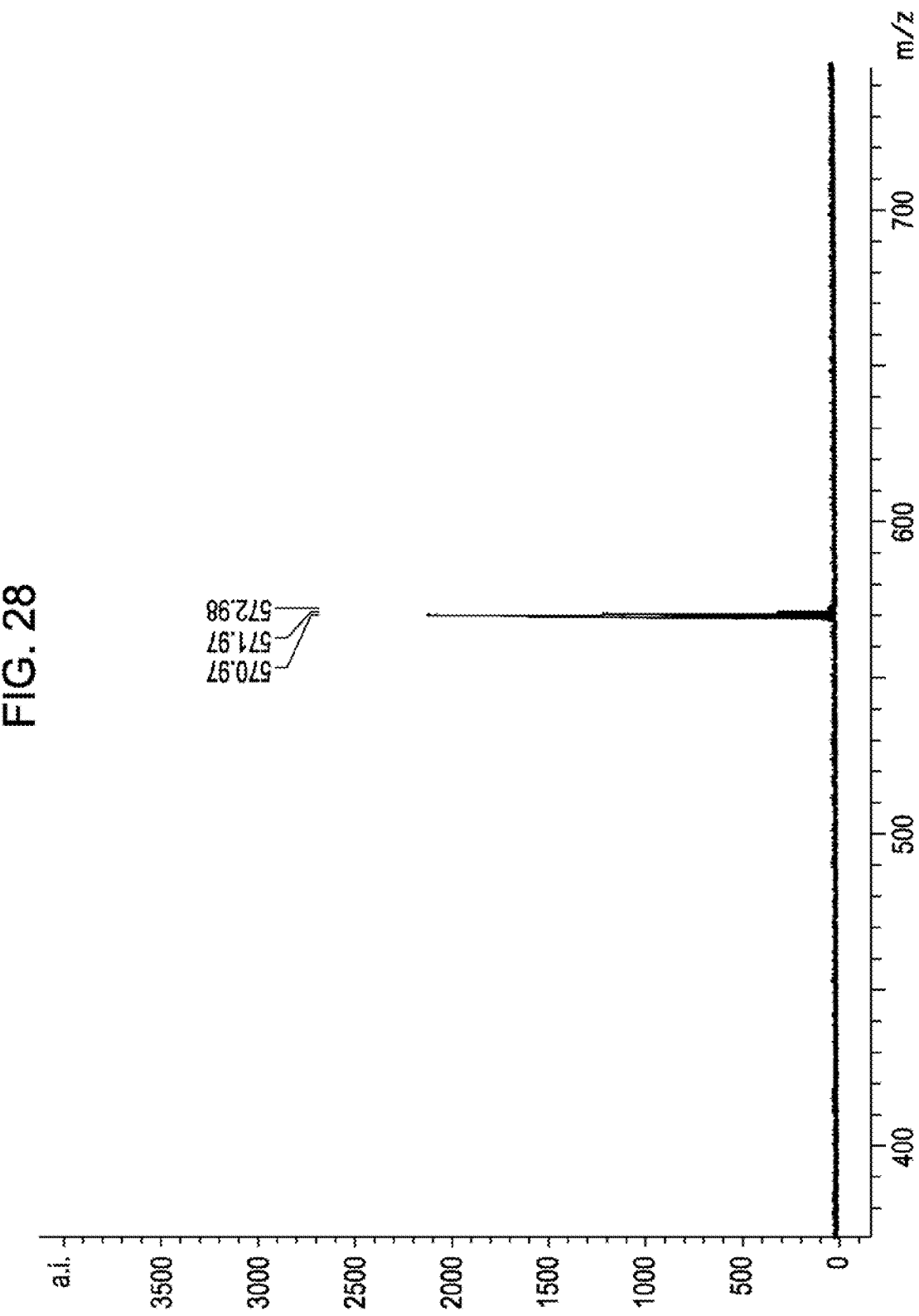
FIG. 28 is a chart showing a MALDI-TOF-MS spectrum of compound (77) in the Example.

FIG. 28 is a chart showing a MALDI-TOF-MS spectrum of compound (77) in the Example.

The MS spectrum shown in FIG. 28 was measured with an apparatus of KRATOS AXIMA-CFR manufactured by Shimadzu Corporation. The MS spectrum shows a calculated value of m/z (m: molecular weight, z: charge number) for each measured peak.

A calculated value of the molecular weight of compound (77) (chemical formula: C$_{42}$H$_{25}$N$_3$) is 571.67. As shown in FIG. 28, the value of m/z (m: molecular weight, z: charge number) and a pattern coefficient (coefficient of frequency of occurrence) for each measured peak were 571.20 (100%), 572.21 (45.7%), 573.21 (10.7%), 574.21 (1.6%), and 572.20 (1.1%). The measured value of the molecular weight was 571.66.

The NMR spectrum shown in FIG. 27 and the MS spectrum shown in FIG. 28 showed that the synthesized compound (77) was the target compound.

Next, absorption and luminous characteristics of the synthesized compound (77) will be described. An absorption spectrum and an emission spectrum were measured with a U-3310 spectrophotometer and an FL-4500 fluorescence spectrophotometer, respectively, both of which were manufactured by Hitachi Ltd. In 1,4-dioxane, compound (77) showed an absorption maximum of 484 nm, a molar extinction coefficient of 12,100, a fluorescence maximum of 647 nm, and a fluorescence quantum yield of 0.33.

According to differential thermal analysis (DSC), it was confirmed that compound (77) has a glass transition temperature of 134° C. and a melting point of 285° C.

[Synthesis Examples of Host Compounds]

Figure 29A:
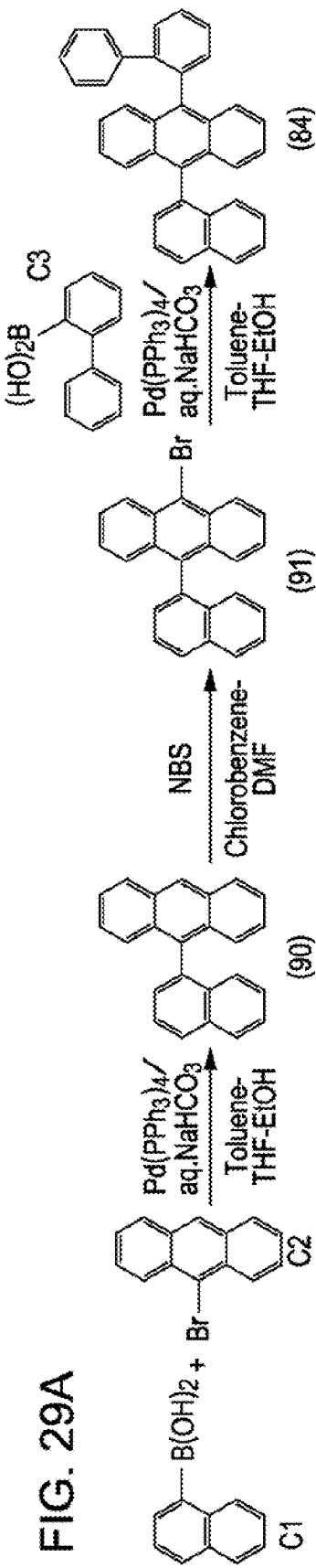
FIGS. 29A to 29C are drawings each showing an example of a synthesis scheme of a host compound in an Example.
Figure 29B:
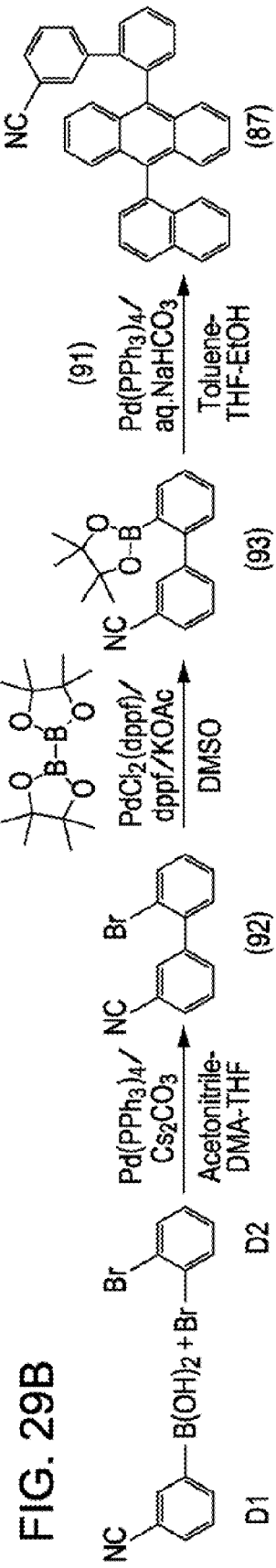
Figure 29C:
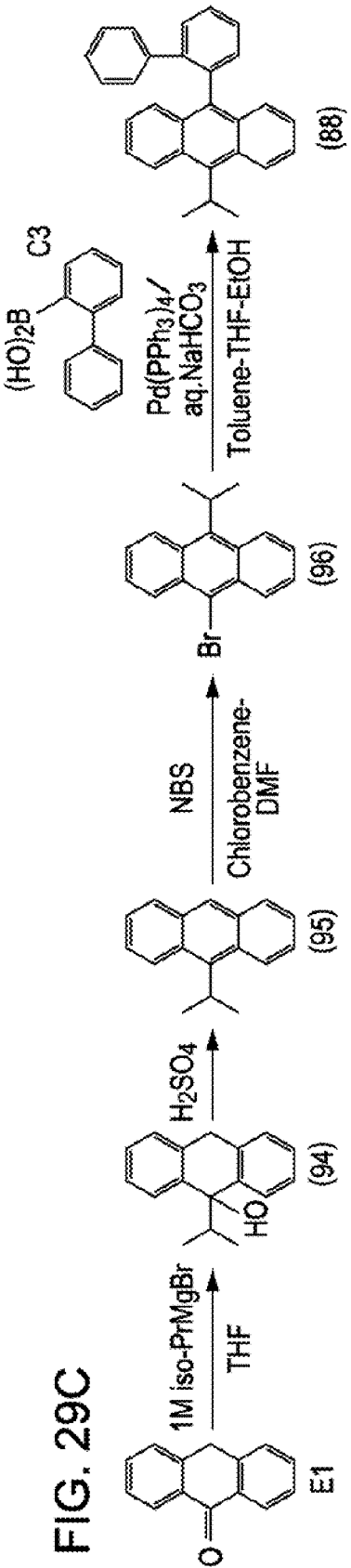

FIGS. 29A to 29C each show an example of a synthesis scheme of a host compound composed of an anthracene derivative compound in an Example. FIG. 29A shows an example of a synthesis scheme of host compound (84) below. FIG. 29B shows an example of a synthesis scheme of host compound (87) below. FIG. 29C shows an example of a synthesis scheme of host compound (88) below.

Compound (84):

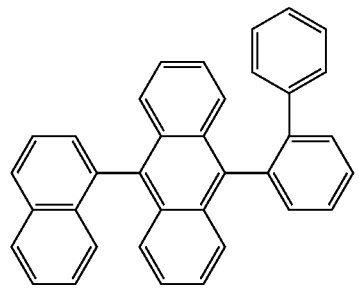

Compound (87):

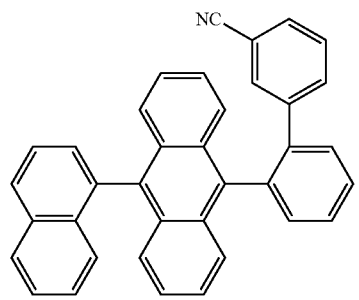

Compound (88):

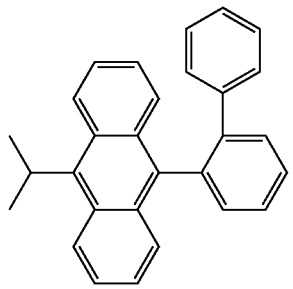

(1) Synthesis Example of Host Compound (84)

A synthesis of host compound (84) will now be described with reference to FIG. 29A.

(1-1) Synthesis Example of Compound (90)

Compound (90) is synthesized by Suzuki coupling reaction in which a biaryl is produced from an aryl boronic acid and an aryl halide in the presence of a base using a palladium (Pd) catalyst. Specifically, 12.8 g (74.7 mmol) of compound C1 ((1-naphthyl)boronic acid, C$_{10}$H$_9$BO$_2$), 12.8 g (49.8 mmol) of compound C2 (9-bromoanthracene, C$_{14}$H$_9$Br), 1.15 g (0.996 mmol) of tetrakis(triphenylphosphine)palladium(0) (Pd(PPh$_3$)$_4$, Pd[P(C$_6$H$_5$)$_3$]$_4$), 150 mL of a saturated aqueous sodium bicarbonate (NaHCO$_3$) solution, 100 mL of ethyl alcohol (EtOH), and 400 mL of tetrahydrofuran (THF) (C$_4$H$_8$O) were mixed. The atmosphere of the resulting reaction solution was replaced with nitrogen three times under stirring, and the reaction solution was then stirred at 75° C. for 14 hours. A saturated saline solution was added to the reaction solution, and the resulting mixture was then separated. The organic layer was dried on sodium sulfate (Na$_2$SO$_4$) and then concentrated under reduced pressure. The resulting crude product was purified by alumina chromatography (eluate: toluene to toluene/THF=20/1). The purified product was recrystallized using acetone-EtOH. Thus, 14.2 g of compound (90) (9-(1-naphthyl)anthracene, C$_{24}$H$_{16}$) was obtained (yield: 94%).

The synthesized compound was identified as the target compound by $^1$H NMR and fast atom bombardment-mass spectrometry (FAB-MS).

$^1$H NMR (400 MHz, CDCl$_3$) δ (ppm): 7.32 (t, 2H), 7.46 (t, 2H), 7.55-7.60 (m, 3H), 7.68 (d, 2H), 7.69-7.93 (m, 2H), 8.00-8.08 (m, 4H), 8.53 (s, 1H).

(1-2) Synthesis Example of Compound (91)

Next, 14.2 g (46.7 mmol) of compound (90) was dissolved in a mixed solvent of 400 mL of chlorobenzene (C$_6$H$_5$Cl) and 50 mL of dimethylformamide (DMF, C$_3$H$_7$NO). Subsequently, 9.0 g (50.7 mmol) of N-bromosuccinimide (NBS, C$_4$H$_4$BrNO$_2$) was added to the solution, and the solution was stirred at 85° C. for three hours. The reaction solution was cooled and then purified by alumina chromatography (eluate: toluene). The eluate was concentrated under reduced pressure. The resulting precipitated crystals were separated by filtration and washed with EtOH. As a result, 14.7 g of compound (91) was obtained (yield: 82%).

The synthesized compound was identified as the target compound by $^1$H NMR and FAB-MS.

$^1$H NMR (400 MHz, CDCl$_3$) δ (ppm): 7.34 (d, 1H), 7.36 (d, 1H), 7.52 (d, 1H), 7.58-7.62 (m, 6H), 7.89-7.91 (m, 2H), 8.01 (d, 1H), 8.06 (d, 1H), 8.63 (d, 2H).

(1-3) Synthesis Example of Compound (84)

Next, 4.17 g (10.8 mmol) of compound (91), 2.80 g (14.1 mmol) of compound C3 (2-biphenylboronic acid, C$_{12}$H$_{11}$BO$_2$), 0.624 g (0.540 mmol) of tetrakis(triphenylphosphine)palladium(0) (Pd(PPh$_3$)$_4$, Pd[P(C$_6$H$_5$)$_3$]$_4$), 100 mL of a saturated aqueous sodium bicarbonate (NaHCO$_3$) solution, 50 mL of EtOH, and 100 mL of tetrahydrofuran (THF) were mixed. The atmosphere of the resulting reaction solution was replaced with nitrogen three times under stirring, and the reaction solution was then stirred at 75° C. for five hours. A saturated saline solution was added to the reaction solution, and the resulting mixture was then separated. The organic layer was dried on sodium sulfate (Na$_2$SO$_4$) and then concentrated under reduced pressure. The resulting crude product was purified by silica gel chromatography (eluate: toluene/hexane=1/20). The purified product was recrystallized using acetone-EtOH. Thus, 1.49 g of compound (84) was obtained (yield: 30%). Subsequently, 4.44 g of the product was purified by sublimation at 280° C. in a vacuum of 10$^{-5}$ Torr to obtain 3.67 g of compound (84).

The synthesized compound was identified as the target compound by $^1$H NMR, $^{13}$C NMR, and FAB-MS.

Figure 30:
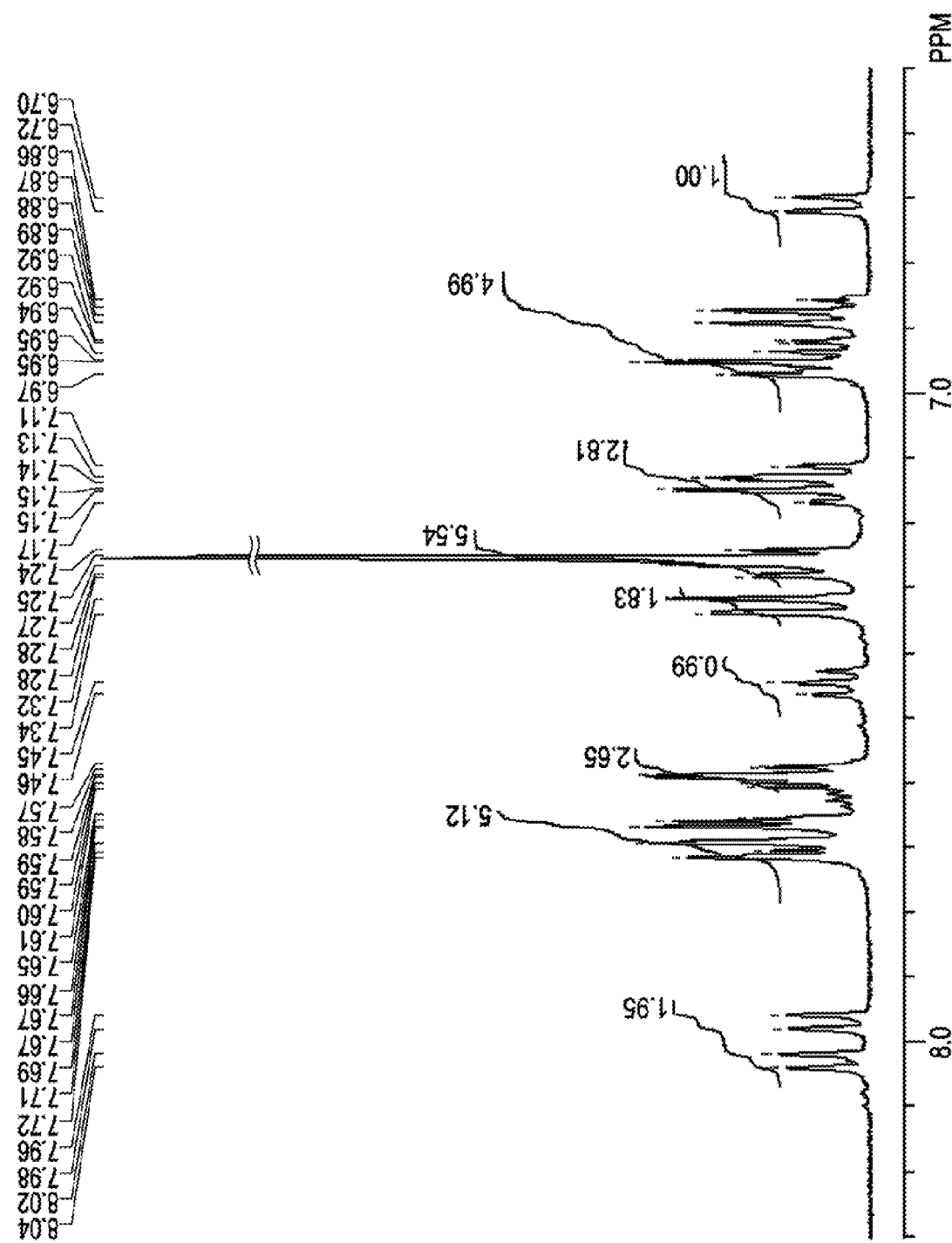
FIG. 30 is a chart showing a $^1$H NMR spectrum of compound (84) in the Example.

FIG. 30 is a chart showing a $^1$H NMR (nuclear magnetic resonance) spectrum of compound (84) in this Example.

Figure 31:
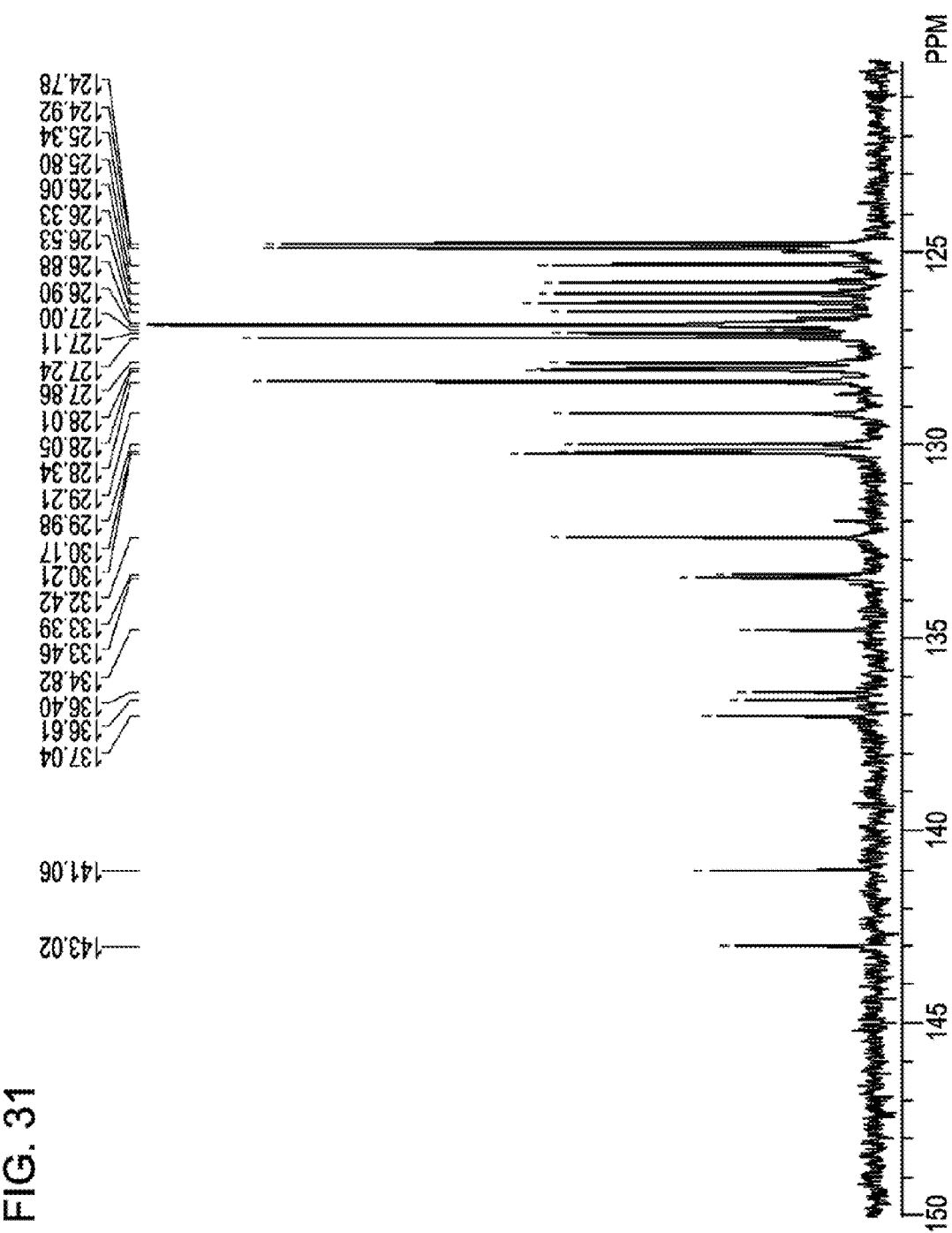
FIG. 31 is a chart showing a $^{13}$C NMR spectrum of compound (84) in the Example.

FIG. 31 is a chart showing a $^{13}$C NMR (nuclear magnetic resonance) spectrum of compound (84) in the Example.

In FIGS. 30 and 31, the horizontal axis represents the chemical shift (ppm), and the vertical axis represents the nuclear magnetic resonance signal intensity. A chemical shift value of each signal peak is shown in the upper part of each of the charts, and the signal intensity is shown near the signal peak. The NMR spectra were measured with a JNM-AL300 FT NMR apparatus manufactured by JEOL Ltd.

$^1$H NMR (400 MHz, CDCl$_3$) δ (ppm): 6.71 (d, 1H), 6.86-6.97 (m, 5H), 7.11-7.17 (m, 3H), 7.24-7.28 (m, 2H), 7.33 (d, 2H), 7.45 (t, 1H), 7.57-7.61 (m, 3H), 7.65-7.72 (m, 5H), 7.97 (d, 1H), 8.03 (d, 1H).

In the $^1$H NMR spectrum, only aromatic hydrogen atoms were observed, and an integral value obtained by subtracting peaks due to impurities and solvents showed that the number of hydrogen atoms was 24, which is the number of hydrogen atoms of compound (84). This result corresponded to the molecular structure of compound (84). The $^{13}$C NMR spectrum (complete decoupling) showed that if the number of magnetically equivalent carbon atoms derived from anthracene is 7, the number of magnetically equivalent carbon atoms derived from compound (84) is 29.

A mass spectrum of compound (84) was measured with a GC-mate II gas chromatograph/mass spectrometer manufactured by JEOL Ltd. by a direct injection method. The mass spectrum was confirmed by an electronic ionization (EI$^+$) method. According to the result, a value of m/z corresponding to a molecular ion peak C$_{36}$H$_{24}$=456 was measured.

Figure 32:
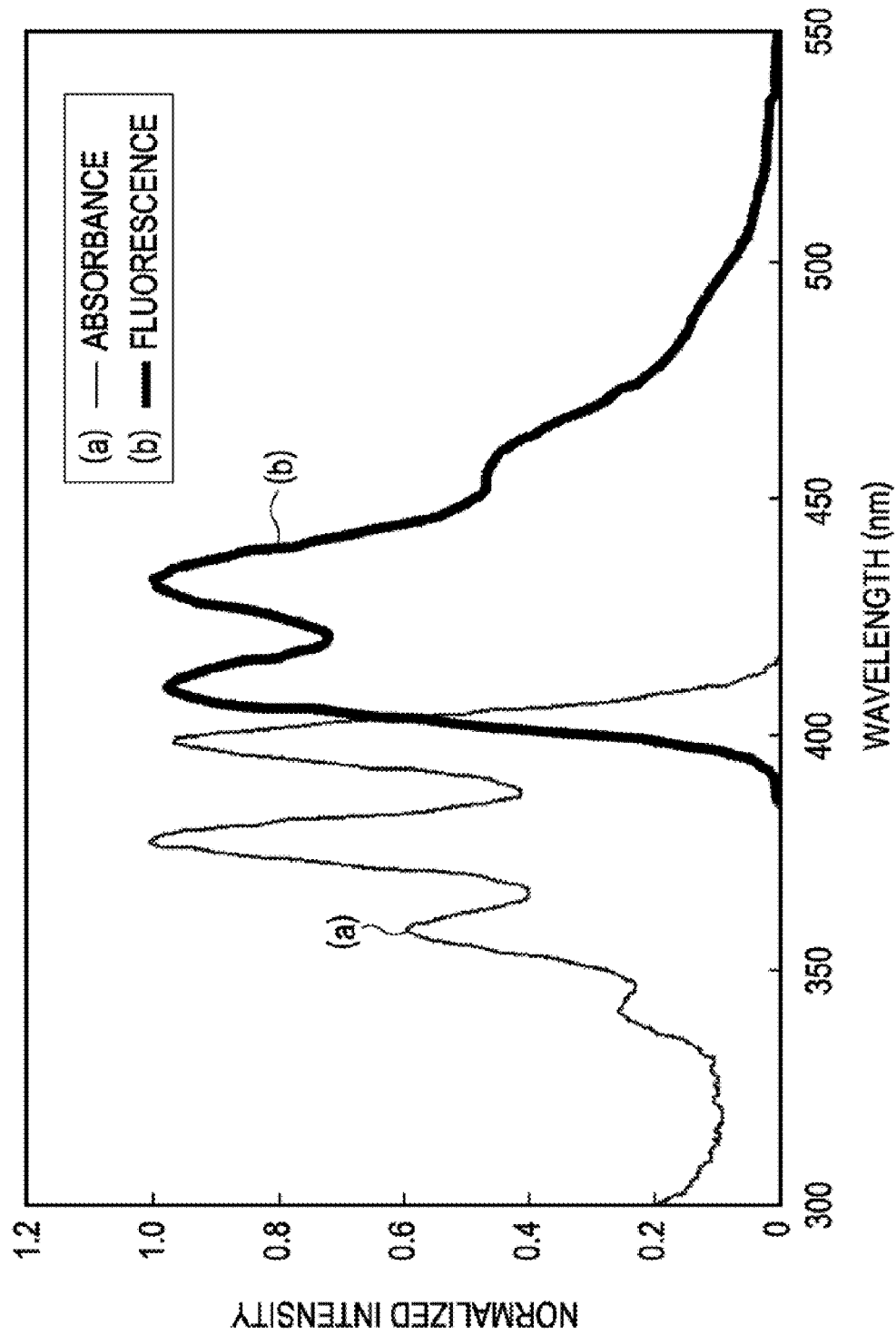
FIG. 32 is a graph showing an absorption spectrum and a fluorescence spectrum of a 1,4-dioxane solution of compound (84) in the Example.

FIG. 32 is a graph showing an absorption spectrum and a fluorescence spectrum of a 1,4-dioxane solution of compound (84) in this Example.

In FIG. 32, (a) shows an absorbance spectrum and (b) shows a fluorescence spectrum. In FIG. 32, the vertical axis represents a normalized intensity normalized by a maximum value, and the horizontal axis represents the wavelength (nm).

As shown in FIG. 32, visible absorption maximum wavelengths of the 1,4-dioxane solution were 358, 378, and 398 nm, and fluorescence maximum wavelengths thereof were 413, 433, and 458 nm. The relative fluorescence quantum efficiency was very high; 0.87.

According to differential thermal analysis (DSC), it was confirmed that compound (84) has a glass transition temperature of 92° C. and a melting point of 264° C.

(2) Synthesis Example of Host Compound (87)

A synthesis of host compound (87) will now be described with reference to FIG. 29B.

(2-1) Synthesis Example of Compound (92)

First, 15.5 g (0.119 mol) of compound D1 (3-cyanophenylboronic acid, C$_7$H$_6$BNO$_2$), 46.3 g (0.178 mol) of compound D2 (1,2-dibromobenzene, C$_6$H$_4$Br$_2$), 6.88 g (5.96 mmol) of tetrakis(triphenylphosphine)palladium(0) (Pd(PPh$_3$)$_4$, Pd[P(C$_6$H$_5$)$_3$]$_4$), 47.35 g (0.145 mol) of cesium carbonate (Cs$_2$CO$_3$), 300 mL of dimethylacetamide (DMA, C$_4$H$_9$NO), 100 mL of acetonitrile, and 400 mL of THF were mixed. The atmosphere of the resulting reaction solution was replaced with nitrogen three times under stirring, and the reaction solution was then stirred at 75° C. for 18 hours. Insoluble matters were removed from the reaction solution by filtration. A saturated saline solution was added to the reaction solution, and the resulting mixture was then separated. The organic layer was dried on Na$_2$SO$_4$ and then concentrated under reduced pressure. The resulting crude product was purified by silica gel chromatography (eluate: toluene/hexane=1/10 to 1/2). The product was recrystallized using acetone-EtOH. As a result, 8.31 g of compound (92) (2'-bromo-1,1'-biphenyl-3-carbonitrile, C$_{13}$H$_8$Br) was obtained (yield: 27%).

The synthesized compound was identified as the target compound by $^1$H NMR and FAB-MS.

$^1$H NMR (400 MHz, CDCl$_3$) δ (ppm): 7.24-7.30 (m, 2H), 7.40 (t, 1H), 7.53 (t, 1H), 7.64-7.77 (m, 4H).

(2-2) Synthesis Example of Compound (93)

In a nitrogen stream, 8.31 g (32.2 mmol) of compound (92), 12.7 g (35.4 mmol) of compound A5 (bis(pinacolate)diboron), 2.63 g (3.22 mmol) of bis(diphenylphosphino)ferrocene)dichloropalladium (PdCl$_2$(dppf)), 1.79 g (3.22 mmol) of bis(diphenylphosphino)ferrocene (dppf), 6.32 g (64.4 mmol) of potassium acetate (KOAc), and 400 mL of dimethyl sulfoxide (DMSO) were mixed. The resulting solution was stirred at 100° C. for 14 hours. Insoluble matters were removed from the reaction solution by filtration. A saturated saline solution was added to the reaction solution, and the resulting mixture was then separated. The organic layer was dried on Na$_2$SO$_4$ and then concentrated under reduced pressure. The resulting crude product was purified by silica gel chromatography (eluate: toluene/hexane=1/20 to toluene/

THF 250/1). As a result, 6.48 g of a crude product of compound (93) was obtained (yield: 66%).

(2-3) Synthesis Example of Compound (87)

Next, 3.67 g (9.55 mmol) of compound (91), 4.48 g (14.7 mmol) of compound (93), 0.552 g (0.355 mmol) of tetrakis(triphenylphosphine)palladium(0) (Pd(PPh$_3$)$_4$), 250 mL of a saturated aqueous NaHCO$_3$ solution, 50 mL of EtOH, and 400 mL of toluene were mixed. The atmosphere of the resulting reaction solution was replaced with nitrogen three times under stirring, and the reaction solution was then stirred at 80° C. for 16 hours. A saturated saline solution was added to the reaction solution, and the resulting mixture was then separated. The organic layer was dried on Na$_2$SO$_4$ and then concentrated under reduced pressure. The resulting crude product was purified by silica gel chromatography (eluate: toluene/hexane=1/20 to 1/1). The product was recrystallized using acetone-EtOH. Thus, 1.42 g of compound (87) was obtained (yield: 32%). Subsequently, the product was purified by sublimation at 240° C. in a vacuum of $10^{-5}$ Torr to obtain 1.12 g of compound (87).

Figure 33:
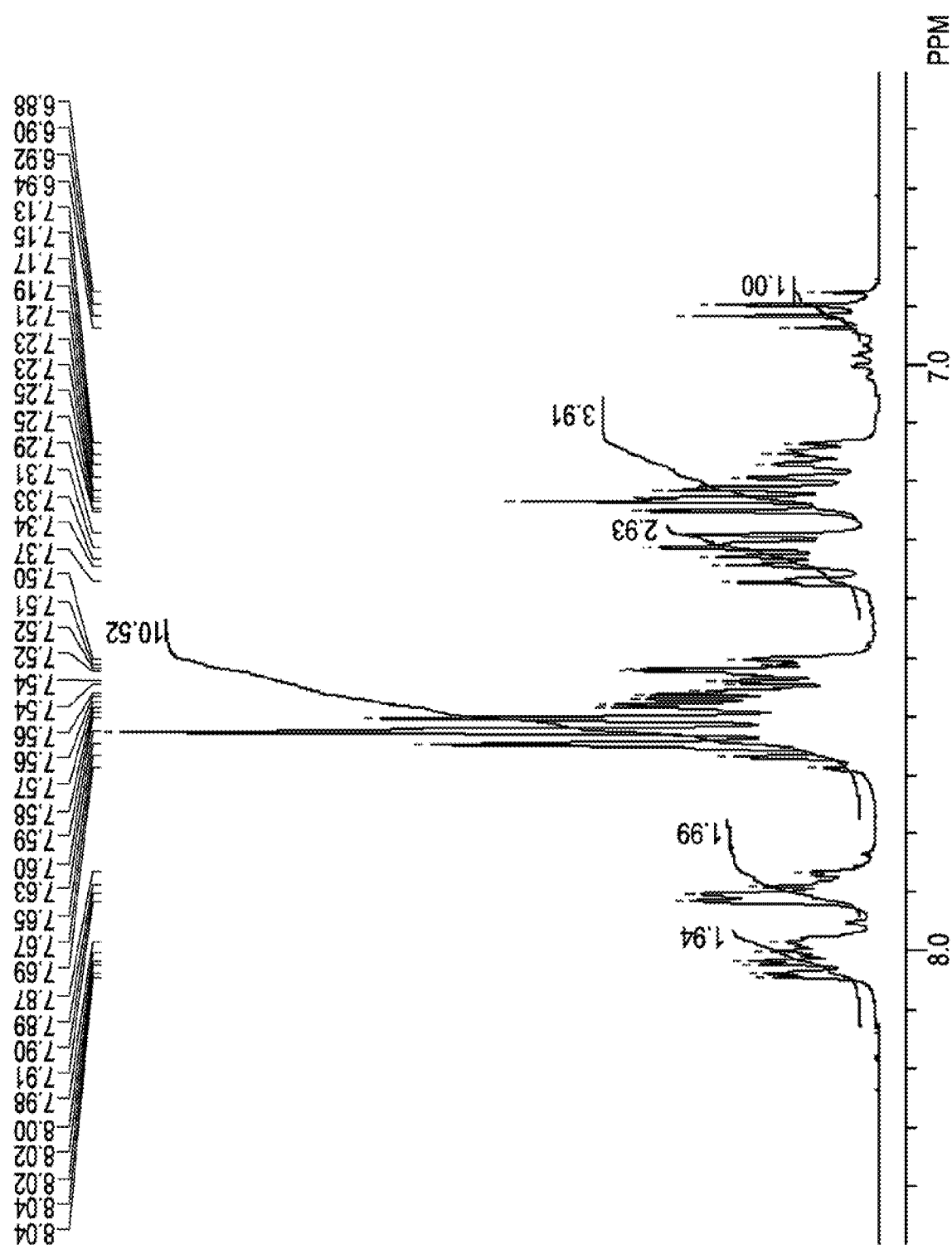
FIG. 33 is a chart showing a $^1$H NMR spectrum of compound (87) in the Example.

FIG. 33 is a chart showing a $^1$H NMR (nuclear magnetic resonance) spectrum of compound (87) in this Example.

Figure 34:
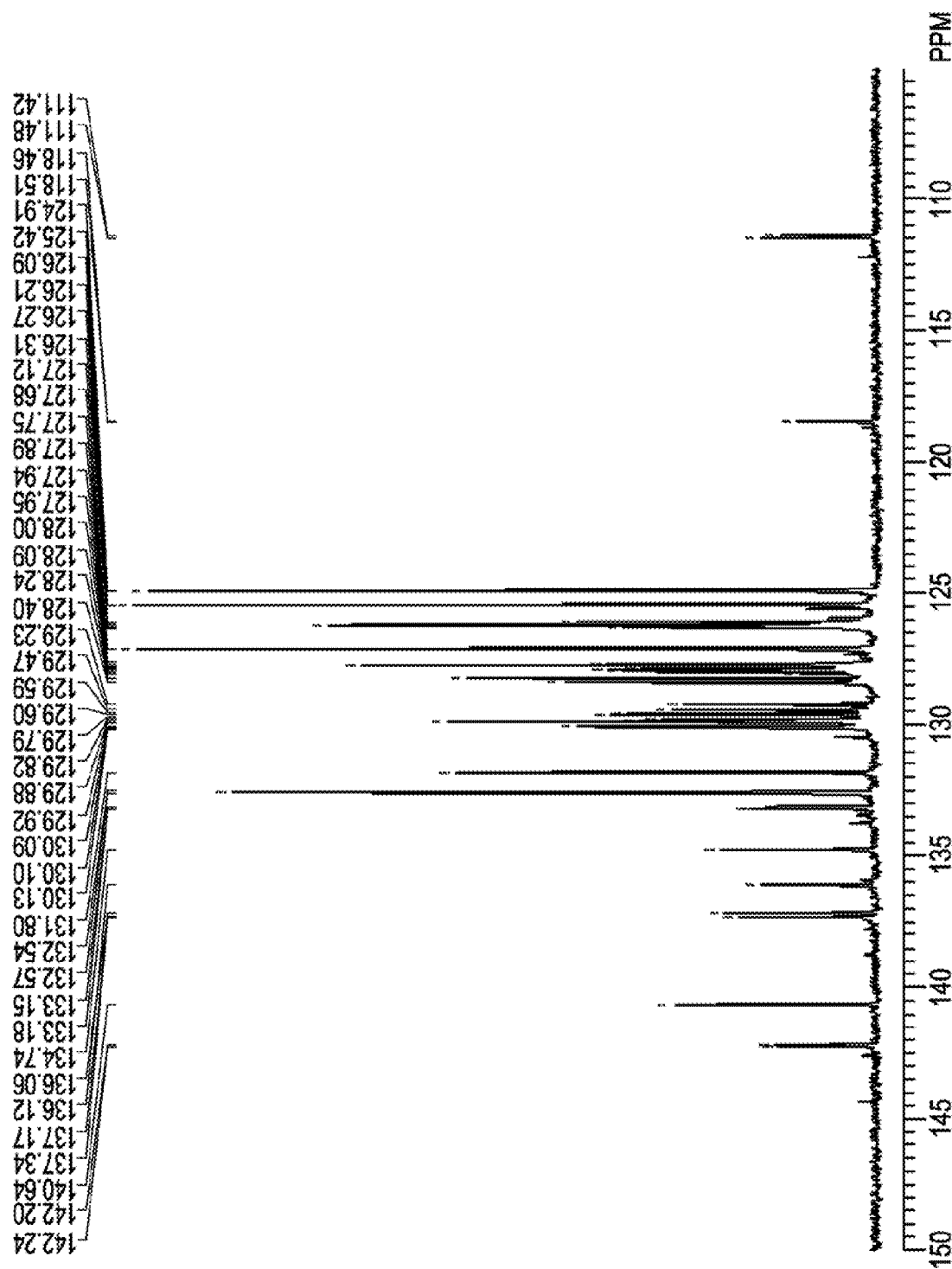
FIG. 34 is a chart showing a $^{13}$C NMR spectrum of compound (87) in the Example.

FIG. 34 is a chart showing a $^{13}$C NMR (nuclear magnetic resonance) spectrum of compound (87) in the Example.

The synthesized compound was identified as the target compound by $^1$H NMR and FAB-MS.

$^1$H NMR (400 MHz, CDCl$_3$) δ (ppm): 6.82-6.93 (m, 1H), 7.14-7.26 (m, 4H), 7.29-7.37 (m, 3H), 7.50-7.66 (m, 11H), 7.87-7.92 (m, 2H), 7.97-8.05 (m, 2H).

In the $^1$H NMR spectrum, only aromatic hydrogen atoms were observed, and an integral value obtained by subtracting peaks due to impurities and solvents showed that the number of hydrogen atoms was 23, which is the number of hydrogen atoms of compound (87). This result corresponded to the molecular structure of compound (87).

In the $^{13}$C NMR spectrum (complete decoupling), two overlapping peaks at 111 ppm each showing a carbon atom substituted with a cyano group and two overlapping peaks at 118 ppm each showing a carbon atom of the cyano group were observed. This result suggests that the synthesized compound contains rotational isomers. However, the result is consistent with the fact that the spectrum shows magnetically equivalent 30 carbon atoms in each of the isomers.

The mass spectrum was confirmed by FAB-MS (EP). According to the result, a value of m/z corresponding to a molecular ion peak C$_{37}$H$_{23}$N=481 was measured.

Figure 35:
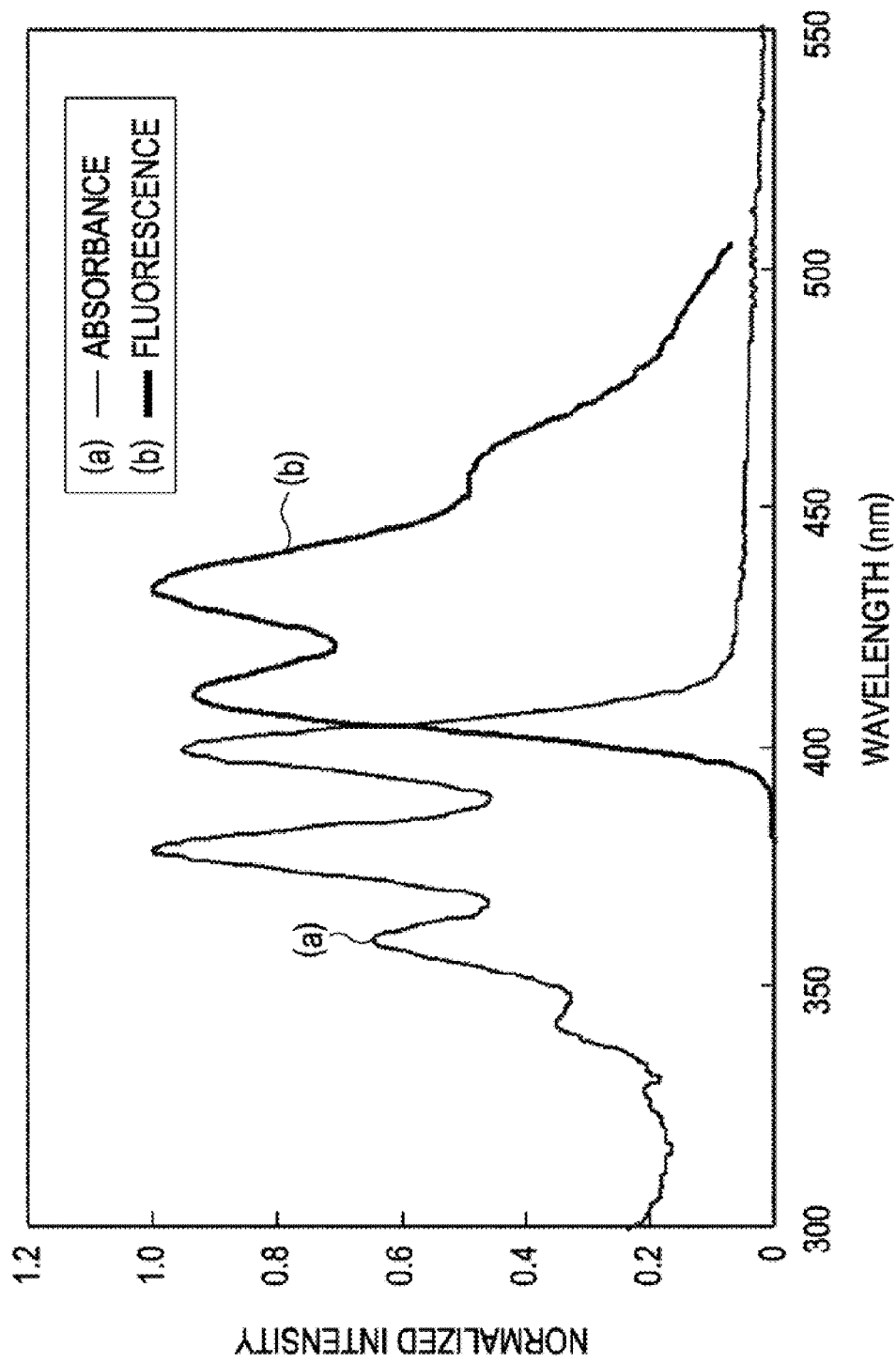
FIG. 35 is a graph showing an absorption spectrum and a fluorescence spectrum of a 1,4-dioxane solution of compound (87) in the Example.

FIG. 35 is a graph showing an absorption spectrum and a fluorescence spectrum of a 1,4-dioxane solution of compound (87) in the Example.

In FIG. 35, (a) shows an absorbance spectrum and (b) shows a fluorescence spectrum. In FIG. 35, the vertical axis represents a normalized intensity normalized by a maximum value, and the horizontal axis represents the wavelength (nm).

As shown in FIG. 35, visible absorption maximum wavelengths of the 1,4-dioxane solution were 358, 378, and 399 nm, and fluorescence maximum wavelengths thereof were 413 and 436 nm. The relative fluorescence quantum efficiency was very high; 0.79.

According to differential thermal analysis (DSC), it was confirmed that compound (87) has a glass transition temperature of 98° C. and a melting point of 204° C.

(3) Synthesis Example of Host Compound (88)

A synthesis of host compound (88) will now be described with reference to FIG. 29C.

(3-1) Synthesis Example of Compound (94) and Compound (95)

First, 500 mL (0.50 mol) of 1 M iso-propylmagnesium bromide (iso-PrMgBr) was diluted with 300 mL of dry tetrahydrofuran (THF). Subsequently, 100 mL of a dry THF solution containing 25.0 g (129 mmol) of compound E1 (anthrone, (C$_{14}$H$_{10}$O)) was added dropwise thereto on an ice bath, and the reaction solution was stirred for 30 minutes. Next, the reaction solution was again cooled to 0° C., and 100 mL (160 mmol) of 1.6 M H$_2$SO$_4$ was added to the solution. The temperature of the reaction solution was gradually increased, and the reaction solution was then refluxed for 15 hours. A saturated saline solution was added to the reaction solution, and the resulting mixture was then separated. The organic layer was dried on Na$_2$SO$_4$ and then concentrated under reduced pressure. The resulting crude product was purified by silica gel chromatography (eluate: toluene/hexane=1/40). The product was recrystallized using acetone-EtOH. Thus, 24.5 g of compound (95) (9-isopropyl-anthracene, C$_{17}$H$_{16}$) was obtained (two-step yield: 86%).

(3-2) Synthesis Example of Compound (96)

Next, 31.1 g (141 mmol) of compound (95) was dissolved in a mixed solvent of 700 mL of chlorobenzene and 100 mL of dimethylformamide (DMF). Subsequently, 27.7 g (155 mmol) of N-bromosuccinimide (NBS) was added to the solution, and the solution was stirred at 70° C. for three hours. The reaction solution was cooled and then purified by alumina chromatography (eluate: toluene), followed by silica gel chromatography (eluate: toluene/hexane=1/20). The eluate was concentrated under reduced pressure. As a result, 24.3 g of wax-like compound (96) (9-isopropyl-10-bromoanthracene, C$_{17}$H$_{15}$Br) was obtained (yield: 57%).

The synthesized compound was identified as the target compound by $^1$H NMR and FAB-MS.

$^1$H NMR (400 MHz, CDCl$_3$) δ (ppm): 1.75 (d, 6H), 4.58 (m, 1H), 7.48-7.52 (m, 2H), 7.57 (t, 2H), 7.47 (d, 2H), 8.63 (d, 2H).

(3-3) Synthesis Example of Compound (88)

Next, 1.00 g (3.34 mmol) of compound (96), 0.500 g (2.52 mmol) of compound C3 (2-biphenylboronic acid), 0.200 g (0.173 mmol) of tetrakis(triphenylphosphine)palladium(0) (Pd(PPh$_3$)$_4$), 50 mL of a saturated aqueous NaHCO$_3$ solution, 10 mL of EtOH, and 80 mL of toluene were mixed. The atmosphere of the resulting solution was replaced with nitrogen three times under stirring, and the reaction solution was then stirred at 80° C. for 48 hours. A saturated saline solution was added to the reaction solution, and the resulting mixture was then separated. The organic layer was dried on Na$_2$SO$_4$ and then concentrated under reduced pressure. The resulting crude product was purified by silica gel chromatography (eluate: toluene/hexane=1/20 to 1/1). The product was recrystallized using acetone-EtOH. Thus, 0.137 g of compound (88) was obtained (yield: 11%). Subsequently, 2.28 g of the product was purified by sublimation at 230° C. in a vacuum of $10^{-5}$ Torr to obtain 1.94 g of compound (88).

The synthesized compound was identified as the target compound by $^1$H NMR and FAB-MS.

1H NMR (400 MHz, CDCl$_3$) δ (ppm): 1.74 (d, 6H), 4.55 (m, 1H), 6.79-6.85 (m, 3H), 6.92 (d, 2H), 7.23-7.27 (m, 2H), 7.36 (m, 3H), 7.49-7.52 (m, 1H), 7.60 (d, 2H), 7.63 (d, 2H).

Figure 36:
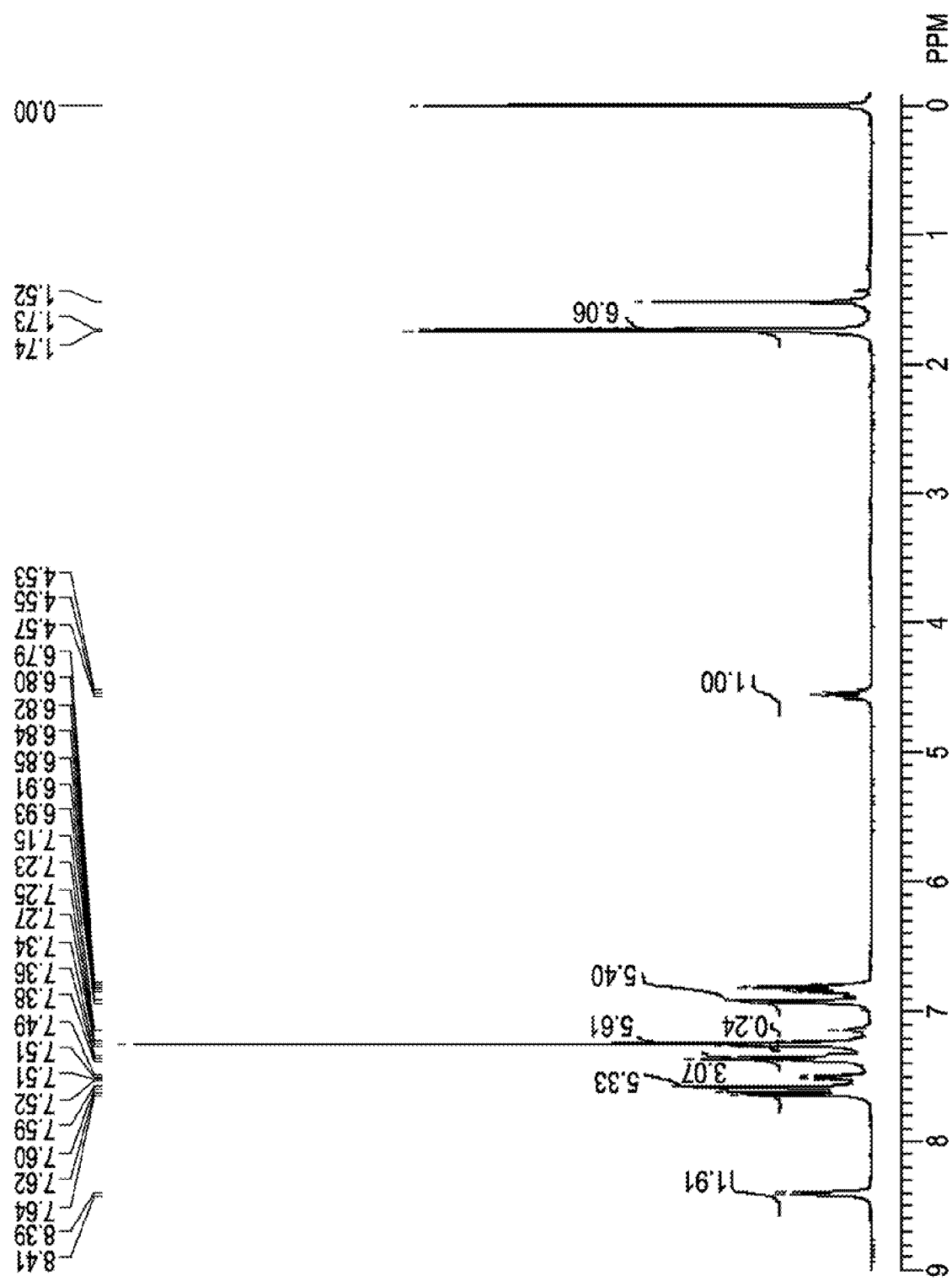
FIG. 36 is a chart showing a $^1$H NMR spectrum of compound (88) in the Example.

FIG. 36 is a chart showing a $^1$H NMR (nuclear magnetic resonance) spectrum of compound (88) in this Example of the present invention.

The integral value of the doublet at 1.74 ppm and the multiplet at 4.55 ppm, which show an isopropyl group, corresponds to 7 hydrogen atoms, and the integral value of the peaks at the low-magnetic-field side of 6.79 ppm or more show 17 hydrogen atoms. This result corresponded to the molecular structure of compound (88).

The mass spectrum was confirmed by FAB-MS (EI+). According to the result, a value of m/z corresponding to a molecular ion peak $C_{29}H_{24}=372$ was measured.

Figure 37:
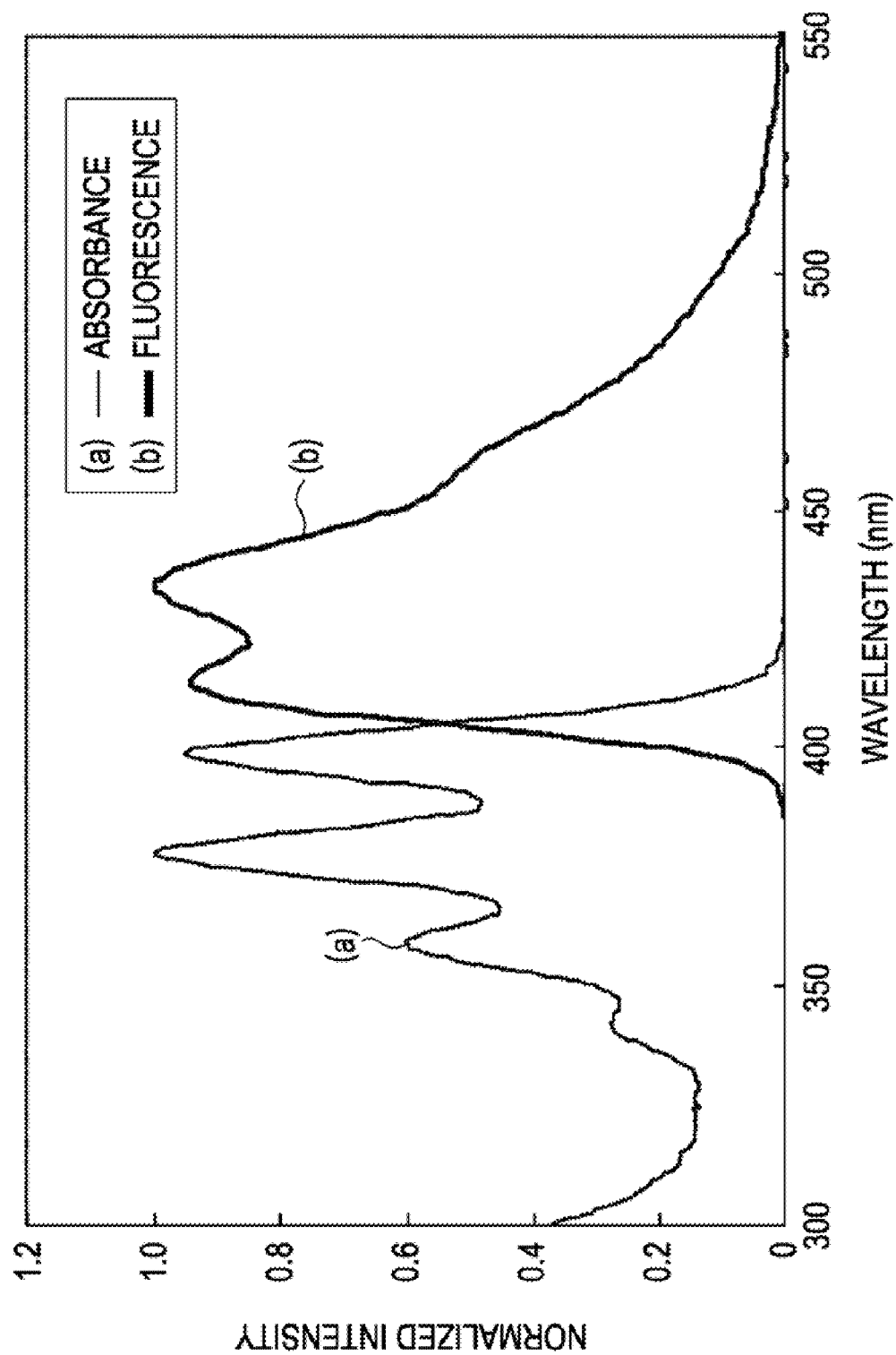
FIG. 37 is a graph showing an absorption spectrum and a fluorescence spectrum of a 1,4-dioxane solution of compound (88) in the Example.

FIG. 37 is a graph showing an absorption spectrum and a fluorescence spectrum of a 1,4-dioxane solution of compound (88) in the Example.

In FIG. 37, (a) shows an absorbance spectrum and (b) shows a fluorescence spectrum. In FIG. 37, the vertical axis represents a normalized intensity normalized by a maximum value, and the horizontal axis represents the wavelength (nm).

As shown in FIG. 37, visible absorption maximum wavelengths of the 1,4-dioxane solution were 358, 378, and 399 nm, and the fluorescence maximum wavelengths thereof were 413, 434, and 460 nm. The relative fluorescence quantum efficiency was very high; 0.79.

According to differential thermal analysis (DSC), it was confirmed that compound (88) has a glass transition temperature of 42° C. and a melting point of 156° C.

In each of the Examples described above, a mixed film containing an aromatic amine compound and an anthracene derivative compound was formed by a codeposition method and used as a light-emitting layer. The mixed film was amorphous, and thermally and chemically stable.

In the Examples described above, each of host compounds (84), (87), and (88) may have a substituent. Each of the hydrogen atoms of an anthracene ring of these compounds may be substituted with a group selected from a trifluoromethyl group; a cyano group; a halogen group; an alkyl group which has 1 to 12 carbon atoms and which may have a substituent; an aryl group which has 5 to 25 carbon atoms, which may have a substituent, and which may contain a heteroatom as a constituent of the ring; an allyl group which may have a substituent; an alkoxy group which has 1 to 12 carbon atoms and which may have a substituent; and an aryloxy group which has 6 to 25 carbon atoms and which may have a substituent.

Each of hydrogen atoms of a first benzene ring bonded to the 10-position of the anthracene ring and each of hydrogen atoms of a second benzene ring bonded to the first benzene ring may be substituted with a group selected from a trifluoromethyl group; a cyano group; a halogen atom; an alkyl group which has 1 to 12 carbon atoms and which may have a substituent; an aryl group which has 6 to 25 carbon atoms, which may have a substituent, and which may contain a heteroatom as a constituent of the ring; an allyl group which may have a substituent; an alkoxy group which has 1 to 12 carbon atoms and which may have a substituent; and an aryloxy group which has 6 to 25 carbon atoms and which may have a substituent. In such a case, adjacent groups may be combined to form a ring.

Furthermore, each of the hydrogen atoms of a naphthalene ring bonded to the 9-position of the anthracene ring may be substituted with a substituent.

In the above embodiments, a description has been made using examples of methods of synthesizing a specific aromatic tertiary amine compound and host compound and organic electroluminescent elements including the compounds. However, the embodiments are not limited to these specific compounds and the organic electroluminescent elements including the compounds.

The luminous efficiency of an organic electroluminescent element depends on the content ratio of an aromatic amine compound (dopant compound) and an anthracene derivative compound (host compound) that form a light-emitting layer. Preferable values of this content ratio vary depending on the combination of the dopant compound and the host compound. The dopant compound and the host compound are prepared in view of the luminescent color of the element, the driving voltage of the element, the luminous efficiency etc. such that the element has suitable characteristics. For example, in the above first organic electroluminescent element and the third organic electroluminescent element described in Examples, the content (volume percent) of the dopant compound is in the range of 0.5% to 5%. In the second organic electroluminescent element and the fourth organic electroluminescent element described in Examples, the content (volume percent) of the dopant compound is in the range of 20% to 40%. In addition, the combination of the dopant compound and the host compound is selected so that a large energy transfer occurs between these compounds.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An aromatic amine compound represented by general formula [I]:

General formula [I]:

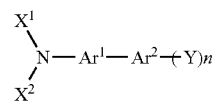

wherein $X^1$ is a phenyl group, $X^2$ is a 2-naphthyl group, $Ar^1$ is a 2,6-naphthylene group, and a group represented by general formula [a] is a 3-phenanthryl group having cyano groups at the 9-position and the 10-position and a methyl group at the 6-position, and the aromatic amine compound is a tertiary amine compound represented by formula [Ia]

General formula [a]:

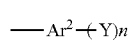

Formula [Ia]:

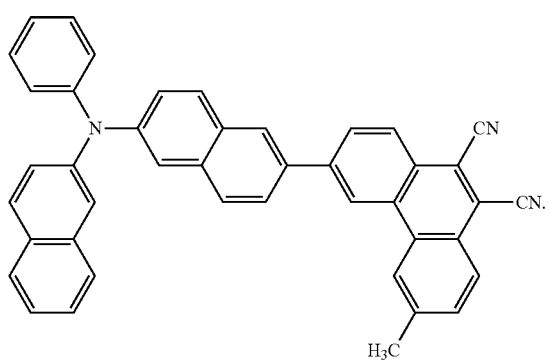

2. An organic electroluminescent element comprising:
an anode;
a cathode; and an organic layer disposed between the anode and the cathode,
wherein at least one layer constituting the organic layer is an amine-compound-containing layer including, as a dopant material, at least one aromatic amine compound represented by general formula [I]:

General formula [I]:

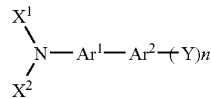

wherein $X^1$ is a phenyl group, $X^2$ is a 2-naphthyl group, $Ar^1$ is a 2,6-naphthylene group, and a group represented by general formula [a] is a 3-phenanthryl group having cyano groups at the 9-position and the 10-position and a methyl group at the 6-position, and
the aromatic amine compound is a tertiary amine compound represented by formula [Ia]

General formula [a]:

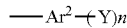

Formula [Ia]:

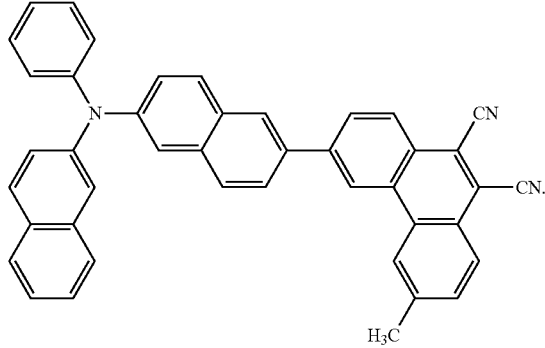

3. The organic electroluminescent element according to claim 2, wherein the organic layer has a structure in which a hole-transporting layer and an electron-transporting layer are stacked.

4. The organic electroluminescent element according to claim 3, wherein at least the hole-transporting layer is the amine-compound-containing layer.

5. The organic electroluminescent element according to claim 3, wherein at least the electron-transporting layer is the amine-compound-containing layer.

6. The organic electroluminescent element according to claim 2, wherein the organic layer has a structure in which a hole-transporting layer, a light-emitting layer, and an electron-transporting layer are stacked.

7. The organic electroluminescent element according to claim 6, wherein at least the light-emitting layer is the amine-compound-containing layer.

8. The organic electroluminescent element according to claim 6,
wherein the light-emitting layer is the amine-compound-containing layer containing the dopant material and a host material, and
the host material is a compound having an anthracene skeleton.

9. A display device comprising:
a pixel portion in which a plurality of pixels each including an organic electroluminescent element are arranged, the organic electroluminescent element including; and
an anode;
a cathode; and
an organic layer disposed between the anode and the cathode,
wherein at least one layer constituting the organic layer is an amine-compound-containing layer including, as a dopant material, at least one aromatic amine compound represented by general formula [I]:

General formula [I]:

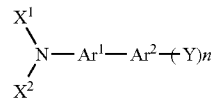

a control unit configured to control a voltage applied to each of the pixels of the pixel portion,
wherein $X^1$ is a phenyl group, $X^2$ is a 2-naphthyl group, $Ar^1$ is a 2,6-naphthylene group, and a group represented by general formula [a] is a 3-phenanthryl group having cyano groups at the 9-position and the 10-position and a methyl group at the 6-position, and
the aromatic amine compound is a tertiary amine compound represented by formula [Ia]

General formula [a]:

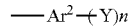

Formula [Ia]:

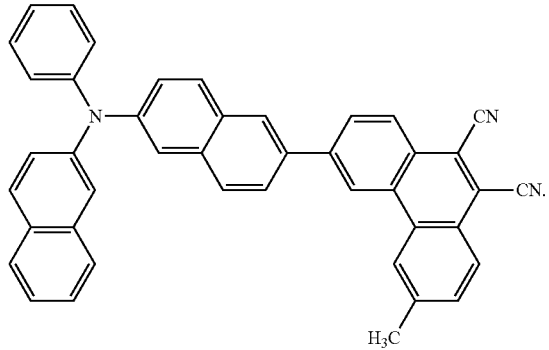

10. The display device according to claim 9, wherein the control unit includes a switching element.

* * * * *